(12) United States Patent
Koppitz et al.

(10) Patent No.: US 9,284,317 B2
(45) Date of Patent: Mar. 15, 2016

(54) SUBSTITUTED IMIDAZO[1,2-A]PYRAZINES AS MPS-1 INHIBITORS

(75) Inventors: Marcus Koppitz, Berlin (DE); Ulrich Klar, Berlin (DE); Rolf Jautelat, Haan (DE); Dirk Kosemund, Berlin (DE); Rolf Bohlmann, Berlin (DE); Benjamin Bader, Berlin (DE); Philip Lienau, Berlin (DE); Gerhard Siemeister, Berlin (DE)

(73) Assignee: Bayer Intellectual Property GmbH, Monheim (DE)

(*) Notice: Subject to any disclaimer, the term of this patent is extended or adjusted under 35 U.S.C. 154(b) by 0 days.

(21) Appl. No.: 13/994,335

(22) PCT Filed: Dec. 13, 2011

(86) PCT No.: PCT/EP2011/072589
§ 371 (c)(1),
(2), (4) Date: Jun. 26, 2013

(87) PCT Pub. No.: WO2012/080234
PCT Pub. Date: Jun. 21, 2012

(65) Prior Publication Data
US 2013/0267527 A1    Oct. 10, 2013

(30) Foreign Application Priority Data
Dec. 17, 2010   (EP) .................................... 10195692

(51) Int. Cl.
*A61K 31/4985*    (2006.01)
*C07D 241/36*    (2006.01)
*C07D 487/04*    (2006.01)
*C07D 403/02*    (2006.01)

(52) U.S. Cl.
CPC ............. *C07D 487/04* (2013.01); *C07D 403/02* (2013.01)

(58) Field of Classification Search
CPC .......................... A61K 31/4985; C07D 241/36

USPC .......... 514/249; 544/350; 546/268.1; 548/518
See application file for complete search history.

(56) References Cited

U.S. PATENT DOCUMENTS

2012/0059162 A1 *   3/2012   Kusakabe et al. .................. 544/3

FOREIGN PATENT DOCUMENTS

WO   WO 2011013729 A1 *   2/2011
WO   WO 2012/080234    *   6/2012

OTHER PUBLICATIONS

Jordan, V. C. Nature Reviews: Drug Discovery, 2, 2003, 205-213.*
Vippagunta, et al. Advanced Drug Delivery Reviews, 48, 2001, 18.*
Hackam, et al. JAMA, 296(14), 2006, 1731-1732.*

* cited by examiner

*Primary Examiner* — Douglas M Willis

(57) ABSTRACT

The present invention relates to substituted imidazopyrazine compounds of general formula (I):

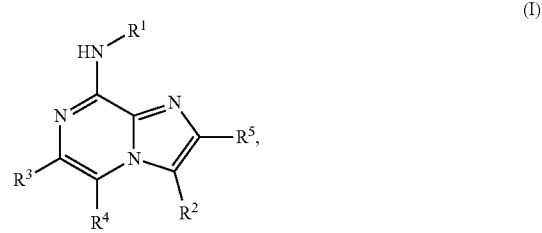

in which $R^1$, $R^2$, $R^3$, $R^4$ and $R^5$ are as defined in the claims, to methods of and intermediates for preparing said compounds, to pharmaceutical compositions and combinations comprising said compounds and to the use of said compounds for manufacturing a pharmaceutical composition for the treatment or prophylaxis of a disease, in particular of a hyperproliferative and/or angiogenesis disorder, as a sole agent or in combination with other active ingredients.

10 Claims, No Drawings

SUBSTITUTED IMIDAZO[1,2-A]PYRAZINES AS MPS-1 INHIBITORS

The present invention relates to substituted imidazopyrazine compounds of general formula (I) as described and defined herein, to methods of and intermediates for preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

BACKGROUND OF THE INVENTION

The present invention relates to chemical compounds that inhibit Mps-1 (Monopolar Spindle 1) kinase (also known as Tyrosine Threonine Kinase, UK). Mps-1 is a dual specificity Ser/Thr kinase which plays a key role in the activation of the mitotic checkpoint (also known as spindle checkpoint, spindle assembly checkpoint) thereby ensuring proper chromosome segregation during mitosis [Abrieu A et al., Cell, 2001, 106, 83-93]. Every dividing cell has to ensure equal separation of the replicated chromosomes into the two daughter cells. Upon entry into mitosis, chromosomes are attached at their kinetochores to the microtubules of the spindle apparatus. The mitotic checkpoint is a surveillance mechanism that is active as long as unattached kinetochores are present and prevents mitotic cells from entering anaphase and thereby completing cell division with unattached chromosomes [Suijkerbuijk S J and Kops G J, Biochemica et Biophysica Acta, 2008, 1786, 24-31; Musacchio A and Salmon E D, Nat Rev Mol Cell Biol., 2007, 8, 379-93]. Once all kinetochores are attached in a correct amphitelic, i.e. bipolar, fashion with the mitotic spindle, the checkpoint is satisfied and the cell enters anaphase and proceeds through mitosis. The mitotic checkpoint consists of complex network of a number of essential proteins, including members of the MAD (mitotic arrest deficient, MAD 1-3) and Bub (Budding uninhibited by benzimidazole, Bub 1-3) families, the motor protein CENP-E, Mps-1 kinase as well as other components, many of these being over-expressed in proliferating cells (e.g. cancer cells) and tissues [Yuan B et al., Clinical Cancer Research, 2006, 12, 405-10]. The essential role of Mps-1 kinase activity in mitotic checkpoint signalling has been shown by shRNA-silencing, chemical genetics as well as chemical inhibitors of Mps-1 kinase [Jelluma N et al., PLos ONE, 2008, 3, e2415; Jones M H et al., Current Biology, 2005, 15, 160-65; Dorer R K et al., Current Biology, 2005, 15, 1070-76; Schmidt M et al., EMBO Reports, 2005, 6, 866-72].

There is ample evidence linking reduced but incomplete mitotic checkpoint function with aneuploidy and tumourigenesis [Weaver B A and Cleveland D W, Cancer Research, 2007, 67, 10103-5; King R W, Biochimica et Biophysica Acta, 2008, 1786, 4-14]. In contrast, complete inhibition of the mitotic checkpoint has been recognised to result in severe chromosome missegregation and induction of apoptosis in tumour cells [Kops G J et al., Nature Reviews Cancer, 2005, 5, 773-85; Schmidt M and Medema R H, Cell Cycle, 2006, 5, 159-63; Schmidt M and Bastians H, Drug Resistance Updates, 2007, 10, 162-81]. Therefore, mitotic checkpoint abrogation through pharmacological inhibition of Mps-1 kinase or other components of the mitotic checkpoint represents a new approach for the treatment of proliferative disorders including solid tumours such as carcinomas and sarcomas and leukaemias and lymphoid malignancies or other disorders associated with uncontrolled cellular proliferation.

Established anti-mitotic drugs such as vinca alkaloids, taxanes or epothilones activate the spindle assembly checkpoint (SAC) inducing a mitotic arrest either by stabilising or destabilising microtubule dynamics. This arrest prevents separation of sister chromatids to form the two daughter cells. Prolonged arrest in mitosis forces a cell either into mitotic exit without cytokinesis or into mitotic catastrophe leading to cell death.

In contrast, inhibitors of Mps1 induce a SAC inactivation that accelerates progression of cells through mitosis resulting in severe chromosomal missegregation and finally in cell death.

These findings suggest that MPS1 inhibitors should be of therapeutic value for the treatment of disorders associated with enhanced uncontrolled proliferative cellular processes such as, for example, cancer, inflammation, arthritis, viral diseases, neurodegenerative diseases such as Alzheimer's disease, cardiovascular diseases, or fungal diseases in a warm-blooded animal such as man.

Therefore, inhibitors of MPS1 represent valuable compounds that should complement therapeutic options either as single agents or in combination with other drugs.

Different compounds have been disclosed in prior art which show an inhibitory effect on Mps-1 kinase. WO2010/124826A1 discloses substituted imidazoquinoxaline compounds as inhibitors of Mps-1 kinase or UK. WO2011/026579A1 discloses substituted aminoquinoxalines as Mps-1 inhibitors. WO2011/063908A1, WO2011/064328A1 as well as WO2011063907 A1 disclose triazolopyridine derivates as inhibitors of Mps-1 kinase.

Imidazopyridazine derivates have been disclosed for the treatment or prophylaxis of different diseases:

WO 2007/038314 A2 (Bristol-Myers Squibb Company) relates to fused heterocyclic compounds useful as kinase modulators, including MK2 modulation. In particular, WO 2007/038314 A2 relates to imidazo[1,2-b]pyridazines.

US patent application publication US 2008/0045536 A1 (Bristol-Myers Squibb Company) similarly relates to fused heterocyclic compounds useful as kinase modulators, including MK2 modulation. In particular, it relates to imidazo[1,2-b]pyridazines.

WO 2010/042699 A1 (Bristol-Myers Squibb Company) relates to fused heterocyclic compounds useful as kinase modulators, particularly CK2 modulation. In particular, WO 2010/042699 A1 relates to imidazo[1,2-b]pyridazines which are substituted with a nitrile group in position 3.

WO 2007/025090 A2 (Kalypsis, Inc.) relates to heterocyclic compounds useful as inhibitors of MEK kinase. In particular, WO 2007/025090 A2 relates inter alia to imidazo[1,2-b]pyridazines.

WO 1998/08847 A1 (Pfizer, Inc.) relates to heterocyclic compounds useful as corticotropin releasing factor (hormone) CRF (CRH) antagonists. In particular, WO 1998/08847 A1 relates inter alia to imidazo[1,2-b]pyridazines.

WO 2011/013729A1 discloses fused imidazole derivatives as Mps-1 inhibitors. Among the disclosed fused imidazole derivates there are also imidazo[1,2-b]pyridazines. For example, WO 2011/013729A1 discloses compounds of formula C1:

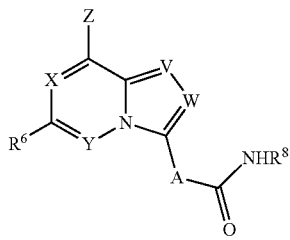

C1

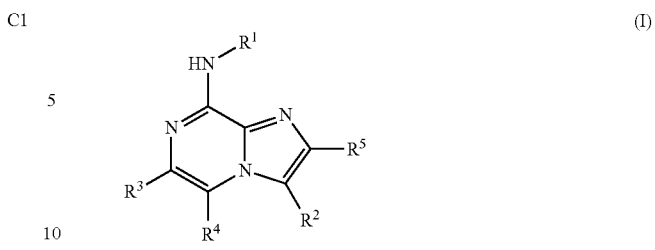

(I)

in which (X, Y, V, W) is (—N═, ═CR¹—, ═N—, —CR⁷═), (—CR²═, ═N—, ═N—, —CR⁷═), (—N═, ═CR¹—, ═N—, —N═) or (—N═, ═CR¹—, —O—, —N═);

R⁸ is substituted or unsubstituted cycloalkyl;

Z is a group represented by formula —NR³R⁴ or a group represented by formula —OR⁵;

A is substituted or unsubstituted aromatic hydrocarbon ring, substituted or unsubstituted aromatic heterocyclic ring, substituted or unsubstituted non-aromatic hydrocarbon ring or substituted or unsubstituted non-aromatic heterocyclic ring;

R¹, R³, R⁴, R⁵, and R⁶ represent a large variety of substituents (see WO 2011/013729A1, e.g. claim 1).

However, the state of the art described above does not describe the specifically substituted imidazopyrazine compounds of general formula (I) of the present invention, or a stereoisomer, a tautomer, an N-oxide, a hydrate, a solvate, or a salt thereof, or a mixture of same, as described and defined herein, and as hereinafter referred to as "compounds of the present invention", or their pharmacological activity. It has now been found, and this constitutes the basis of the present invention, that said compounds of the present invention have surprising and advantageous properties.

In particular, said compounds of the present invention have surprisingly been found to effectively inhibit Mps-1 kinase and may therefore be used for the treatment or prophylaxis of diseases of uncontrolled cell growth, hyperproliferation, an inappropriate cellular immune response, or an inappropriate cellular inflammatory response, particularly in which the uncontrolled cell growth, hyperproliferation, inappropriate cellular immune response, or inappropriate cellular inflammatory response is mediated directly or indirectly by the monopolar spindle 1 kinase (MPS-1), such as, for example, haemotological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

BRIEF SUMMARY OF THE INVENTION

In accordance with a first aspect, the present invention covers compounds of general formula (I):

in which:
R¹ represents a *CH₂—Z—Z moiety, * indicating the point of attachment with the rest of the molecule,
wherein Z is a hydrogen atom, or a $C_1$-$C_6$-alkyl-, —(CH₂)ₘ—$C_2$-$C_6$-alkenyl, —(CH₂)ₙ—$C_2$-$C_6$-alkynyl, —(CH₂)ₘ—$C_3$-$C_6$-cycloalkyl, —(CH₂)ₘ-(3- to 7-membered heterocycloalkyl), aryl-$C_1$-$C_6$-alkyl-, heteroaryl-$C_1$-$C_6$-alkyl-, halo-$C_1$-$C_6$-alkyl-, R'(R")N—$C_1$-$C_6$-alkyl-, HO—$C_1$-$C_6$-alkyl-, H₂N—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl- group;
said $C_1$-$C_6$-alkyl-, —(CH₂)ₘ—$C_2$-$C_6$-alkenyl, —(CH₂)ₙ—$C_2$-$C_6$-alkynyl, —(CH₂)ₘ—$C_3$-$C_6$-cycloalkyl, —(CH₂)ₘ-(3- to 7-membered heterocycloalkyl), aryl-$C_1$-$C_6$-alkyl-, heteroaryl-$C_1$-$C_6$-alkyl-, halo-$C_1$-$C_6$-alkyl-, R'(R")N—$C_1$-$C_6$-alkyl-, HO—$C_1$-$C_6$-alkyl-, H₂N—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl- group, is optionally substituted, identically or differently, with 1, 2, 3, or 4 R⁷ groups;
R² represents a

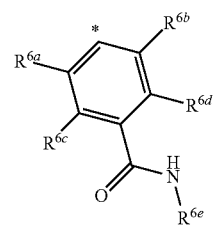

group,
in which * indicates the point of attachment with the rest of the molecule, and in which
$R^{6a}$, $R^{6b}$, $R^{6c}$, $R^{6d}$
represent, independently from each other, a hydrogen or halogen atom, or a —CN, $C_1$-$C_6$-alkyl-, $C_1$-$C_6$-alkoxy-, halo-$C_1$-$C_6$-alkyl-, R(R')N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —C(═O)R, —C(═O)N(H)R, —C(═O)N(R)R', —C(═O)O—R, —N(R)R', —NO₂, —N(H)C(═O)R, —N(R)C(═O)R', —N(H)C(═O)N(R)R', —N(R)C(═O)N(R')R", —N(H)C(═O)OR, —N(R)C(═O)OR', —N(H)S(═O)R', —N(R)S(═O)R', —N(H)S(═O)₂R, —N(R)S(═O)₂R', —N═S(═O)(R)R', —OR, —O(C═O)R, —O(C═O)N(R)R', —O(C=O)OR, —SR, —S(=O)R, —S(=O)N(H)R, —S(=O)N(R)R', —S(=O)₂R, —S(=O)₂N(H)R, —S(=O)₂N(R)R', S(=O)(=NR)R' group; and R⁶ᵉ represents a cyclopropyl-group being optionally substituted, identically or differently, with 1, 2, 3, or 4 groups selected from: hydrogen, halogen, —OH, —CN, C₁-C₆-alkyl-, —C₁-C₆-alkoxy, halo-C₁-C₆-alkyl-;

R³ represents a hydrogen atom or a halogen atom, or a —CN, C₁-C₆-alkyl-, —(CH₂)ₘ—C₂-C₆-alkenyl, —(CH₂)ₘ—C₄-C₈-cycloalkenyl —(CH₂)ₙ—C₂-C₆-alkynyl, —(CH₂)ₘ—C₃-C₆-cycloalkyl, —(CH₂)ₘ-(3- to 7-membered heterocycloalkyl), —(CH₂)ₘ-(4- to 8-membered heterocycloalkenyl), aryl-C₁-C₆-alkyl-, heteroaryl-C₁-C₆-alkyl-, halo-C₁-C₆-alkyl-, R(R') N—C₁-C₆-alkyl-, halo-C₁-C₆-alkoxy-C₁-C₆-alkyl-, C₃-C₆-cycloalkyl-, a 3- to 7-membered heterocycloalkyl, C₂-C₆-alkenyl-, C₄-C₈-cycloalkenyl-, C₂-C₆-alkynyl-, aryl-, —C1-C6-alkyl-aryl, —C1-C6-alkyl-heteroaryl, heteroaryl-, —C(=O)R, —C(=O)N(H)R, —C(=O)N(R)R', —C(=O)O—R, —N(R)R', —NO₂, —N(H)C(=O)R or a

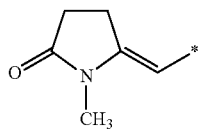 [SMILES: */C=C1\CCC(=O)N1C]

group, wherein
* indicates the point of attachment with the rest of the molecule;
said C₁-C₆-alkyl-, —(CH₂)ₘ—C₂-C₆-alkenyl, —(CH₂)ₘ—C₄-C₈-cycloalkenyl —(CH₂)ₙ—C₂-C₆-alkynyl, —(CH₂)ₘ—C₃-C₆-cycloalkyl, —(CH₂)ₘ-(3- to 7-membered heterocycloalkyl), —(CH₂)ₘ-(4- to 8-membered heterocycloalkenyl), aryl-C₁-C₆-alkyl-, heteroaryl-C₁-C₆-alkyl-, halo-C₁-C₆-alkyl-, R(R')N—C₁-C₆-alkyl-, halo-C₁-C₆-alkoxy-C₁-C₆-alkyl-, C₃-C₆-cycloalkyl-, a 3- to 7-membered heterocycloalkyl, C₂-C₆-alkenyl-, C₄-C₈-cycloalkenyl-, C₂-C₆-alkynyl-, aryl-, —C1-C6-alkyl-aryl, —C1-C6-alkyl-heteroaryl, heteroaryl-, —C(=O)R, —C(=O)N(H)R, —C(=O)N(R)R', —C(=O)O—R, —N(R)R', —NO₂, —N(H)C(=O)R or

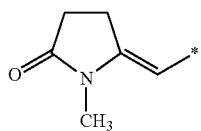 [SMILES: */C=C1\CCC(=O)N1C]

group, being optionally substituted, identically or differently, with 1, 2, 3, or 4 R⁸ groups;

R⁴ represents a hydrogen or halogen atom, or a —CN, C₁-C₆-alkyl- or aryl-group;

R⁵ represents a hydrogen atom;

R⁷ represents a hydrogen or halogen atom, or a —CN, HO—, C₁-C₆-alkoxy-, C₁-C₆-alkyl-, halo-C₁-C₆-alkyl-, halo-C₁-C₆-alkoxy- R(R')N—C₁-C₆-alkyl-, HO—C₁-C₆-alkyl, HO—C₁-C₆-alkoxy, C₁-C₆-alkoxy-C₁-C₆-alkyl-, halo-C₁-C₆-alkoxy-C₁-C₆-alkyl-, C₂-C₆-alkenyl, 3- to 7-membered heterocycloalkyl, aryl-, heteroaryl-, —C(=O)R, —C(=O)N(H)R, —C(=O)N(R)R', —C(=O)O—R, —N(R)R', —NO₂, —N(H)C(=O)R, —N(R)C(=O)R', —N(H)C(=O)N(R)R', —N(R)C(=O)N(R')R", —N(H)C(=O)OR, —N(R)C(=O)OR', —N(H)S(=O)R, —N(R)S(=O)R', —N(H)S(=O)₂R, —N(R)S(=O)₂R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)₂R, —S(=O)₂N(H)R, —S(=O)₂N(R)R', —S(=O)(=NR)R', —S(=O)₂-(3- to 7-membered heterocycloalkyl) group;

wherein said 3- to 7-membered heterocycloalkyl- or heteroaryl-, is optionally substituted, identically or differently, with 1, 2, 3, or 4 C₁-C₆-alkyl- groups R⁸ represents a hydrogen or halogen atom, or a —CN, HO—, C₁-C₆-alkoxy-, halo-C₁-C₆-alkoxy-, C₁-C₆-alkyl-, —C₁-C₆-alkyl-N(H)C(=O)R, —C₁-C₆-alkyl-C(=O)N(H)R, —C₁-C₆-alkyl-C(=O)OR, halo-C₁-C₆-alkyl-, R(R')N—C₁-C₆-alkyl-, HO—C₁-C₆-alkyl, HO—C₁-C₆-alkoxy, C₁-C₆-alkoxy-C₁-C₆-alkyl-, halo-C₁-C₆-alkoxy-C₁-C₆-alkyl-, —C₂-C₆-alkenyl, 3- to 7-membered heterocycloalkyl-, aryl-, heteroaryl-, —C(=O)R, —C(=O)N(H)R, —C(=O)N(R)R', —C(=O)O—R, —N(R)R', —NO₂, —N(H)C(=O)R, —N(R)C(=O)R', —N(H)C(=O)N(R)R', —N(R)C(=O)N(R')R", —N(H)C(=O)OR, N(R)C(=O)OR', —N(H)S(=O)R, —N(R)S(=O)R', —N(H)S(=O)₂R, —N(R)S(=O)₂R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)₂R, —S(=O)₂N(H)R, —S(=O)₂N(R)R', —S(=O)(=NR)R', —S(=O)₂-(3- to 7-membered heterocycloalkyl) group;

R, R' and R" are, independently from each other, a hydrogen atom or a C₁-C₆-alkyl-, —C₃-C₆-cycloalkyl, C₃-C₆-alkenyl-, aryl- or a heteroaryl- group;

m is an integer of 0, 1, 2, 3, 4, 5 or 6;

n is an integer of 1, 2, 3, 4 or 5;

or a stereoisomer, a tautomer, an N-oxide, a hydrate, a solvate, or a salt thereof, or a mixture of same.

In accordance with a second aspect, the present invention covers compounds of general formula (I), supra, in which:

R¹ represents a *CH₂—Z moiety, * indicating the point of attachment with the rest of the molecule, wherein Z is a hydrogen atom, or a C₁-C₆-alkyl-, —(CH₂)ₘ—C₂-C₆-alkenyl, —(CH₂)ₙ—C₂-C₆-alkynyl, —(CH₂)ₘ—C₃-C₆-cycloalkyl, —(CH₂)ₘ-(3- to 7-membered heterocycloalkyl), aryl-C₁-C₆-alkyl-, heteroaryl-C₁-C₆-alkyl-, halo-C₁-C₆-alkyl-, R'(R")N—C₁-C₆-alkyl-, HO—C₁-C₆-alkyl-, H₂N—C₁-C₆-alkyl-, —C₁-C₆-alkyl-CN, C₁-C₆-alkoxy-C₁-C₆-alkyl-, halo-C₁-C₆-alkoxy-C₁-C₆-alkyl-, C₃-C₆-cycloalkyl-, a 3- to 7-membered heterocycloalkyl-, C₂-C₆-alkenyl-, C₄-C₈-cycloalkenyl-, C₂-C₆-alkynyl-, aryl- or heteroaryl-group;

said C₁-C₆-alkyl-, —(CH₂)ₘ—C₂-C₆-alkenyl, —(CH₂)ₙ—C₂-C₆-alkynyl, —(CH₂)ₘ—C₃-C₆-cycloalkyl, —(CH₂)ₘ-(3- to 7-membered heterocycloalkyl), aryl-C₁-C₆-alkyl-, heteroaryl-C₁-C₆-alkyl-, halo-C₁-C₆-alkyl-, R'(R")N—C₁-C₆-alkyl-, HO—C₁-C₆-alkyl-, H₂N—C₁-C₆-alkyl-, —C₁-C₆-alkyl-CN, C₁-C₆-alkoxy-C₁-C₆-alkyl-, halo-C₁-C₆-alkoxy-C₁-C₆-alkyl-, C₃-C₆-cycloalkyl-, a 3- to 7-membered heterocycloalkyl-, C₂-C₆-alkenyl-, C₄-C₈-cycloalkenyl-, C₂-C₆-alkynyl-, aryl- or heteroaryl- group, is optionally substituted, identically or differently, with 1, 2, 3, or 4 R⁷ groups;

$R^2$ represents a

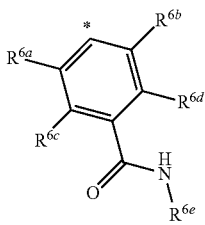

group,
in which * indicates the point of attachment with the rest of the molecule, and in which
$R^{6a}$, $R^{6b}$, $R^{6c}$, $R^{6d}$
represent, independently from each other, a hydrogen or halogen atom; and
$R^{6e}$ represents a cyclopropyl-group;
$R^3$ represents a hydrogen atom or a halogen atom, or a —CN, $C_1$-$C_6$-alkyl-, —$(CH_2)_m$—$C_2$-$C_6$-alkenyl, —$(CH_2)_m$—$C_4$-$C_8$-cycloalkenyl —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, R(R')N—$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl, $C_2$-$C_6$-alkenyl-, $C_4$-$C_8$-cycloalkenyl-, $C_2$-$C_6$-alkynyl-, aryl-, —C1-C6-alkyl-aryl, —C1-C6-alkyl-heteroaryl, heteroaryl-, —C(=O)R, —C(=O)N(H)R, —C(=O)N(R)R', —C(=O)O—R, —N(R)R',
—$NO_2$, —N(H)C(=O)R or a

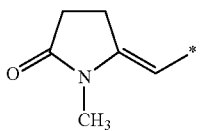 [SMILES: */C=C1\CCC(=O)N1C]

group, wherein
* indicates the point of attachment with the rest of the molecule;
said $C_1$-$C_6$-alkyl-, —$(CH_2)_m$—$C_2$-$C_6$-alkenyl, —$(CH_2)_m$—$C_4$-$C_8$-cycloalkenyl —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, R(R')N—$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl, $C_2$-$C_6$-alkenyl-, $C_4$-$C_8$-cycloalkenyl-, $C_2$-$C_6$-alkynyl-, aryl-, —C1-C6-alkyl-aryl, —C1-C6-alkyl-heteroaryl, heteroaryl-, —C(=O)R, —C(=O)N(H)R, —C(=O)N(R)R', —C(=O)O—R, —N(R)R', —$NO_2$, —N(H)C(=O)R or

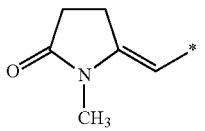

being optionally substituted, identically or differently, with 1, 2, 3, or 4 $R^8$ groups;
$R^4$ represents a hydrogen or halogen atom, or a —CN, $C_1$-$C_6$-alkyl- or aryl-group;
$R^5$ represents a hydrogen atom;
$R^7$ represents a hydrogen or halogen atom, or a —CN, HO—, $C_1$-$C_6$-alkoxy-, $C_1$-$C_6$-alkyl-, halo-$C_1$-$C_6$-alkyl-, halo-$C_1$-$C_6$-alkoxy- R(R')N—$C_1$-$C_6$-alkyl, HO—$C_1$-$C_6$-alkyl, HO—$C_1$-$C_6$-alkoxy, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)R, —C(=O)N(H)R, —C(=O)N(R)R', —C(=O)O—R, —N(R)R', —$NO_2$, —N(H)C(=O)R, —N(R)C(=O)R', —N(H)C(=O)N(R)R', —N(R)C(=O)N(R')R'', —N(H)C(=O)OR, —N(R)C(=O)OR', —N(H)S(=O)R, —N(R)S(=O)R', —N(H)S(=O)$_2$R, —N(R)S(=O)$_2$R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)$_2$R, —S(=O)$_2$N(H)R, —S(=O)$_2$N(R)R', —S(=O)(=NR)R', —S(=O)$_2$-(3- to 7-membered heterocycloalkyl) group;
$R^8$ represents a hydrogen or halogen atom, or a —CN, HO—, $C_1$-$C_6$-alkoxy-, halo-$C_1$-$C_6$-alkoxy-, $C_1$-$C_6$-alkyl-, —$C_1$-$C_6$-alkyl-N(H)C(=O)R, —$C_1$-$C_6$-alkyl-C(=O)N(H)R, —$C_1$-$C_6$-alkyl-C(=O)OR, halo-$C_1$-$C_6$-alkyl-, R(R')N—$C_1$-$C_6$-alkyl-, HO—$C_1$-$C_6$-alkyl, HO—$C_1$-$C_6$-alkoxy, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl-, aryl-, heteroaryl-, —C(=O)R, —C(=O)N(H)R, —C(=O)N(R)R', —C(=O)O—R, —N(R)R', —$NO_2$, —N(H)C(=O)R, —N(R)C(=O)R', —N(H)C(=O)N(R)R', —N(R)C(=O)N(R')R'', —N(H)C(=O)OR, N(R)C(=O)OR', —N(H)S(=O)R, —N(R)S(=O)R', —N(H)S(=O)$_2$R, —N(R)S(=O)$_2$R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)$_2$R, —S(=O)$_2$N(H)R, —S(=O)$_2$N(R)R', —S(=O)(=NR)R', —S(=O)$_2$-(3- to 7-membered heterocycloalkyl) group;
R, R' and R'' are, independently from each other, a hydrogen atom or a $C_1$-$C_6$-alkyl-, —$C_3$-$C_6$-cycloalkyl, $C_3$-$C_6$-alkenyl-, aryl- or a heteroaryl- group;
m is an integer of 0, 1, 2, 3, 4, 5 or 6;
n is an integer of 1, 2, 3, 4 or 5;
or a stereoisomer, a tautomer, an N-oxide, a hydrate, a solvate, or a salt thereof, or a mixture of same.

In accordance with a third aspect, the present invention covers compounds of general formula (I), supra, in which:
$R^1$ represents a *$CH_2$—Z moiety, * indicating the point of attachment with the rest of the molecule,
wherein Z is a hydrogen atom, or a $C_1$-$C_6$-alkyl-, —$(CH_2)_m$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, R'(R'')N—$C_1$-$C_6$-alkyl-, HO—$C_1$-$C_6$-alkyl-, $H_2$N—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl-group;
said $C_1$-$C_6$-alkyl-, —$(CH_2)_m$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, R'(R'')N—$C_1$-$C_6$-alkyl-, HO—$C_1$-$C_6$-alkyl-, $H_2$N—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl- group, is optionally substituted, identically or differently, with 1, 2, 3, or 4 $R^7$ groups;

$R^2$ represents a

[structure: benzamide with R^6a, R^6b, R^6c, R^6d on ring and C(=O)NH-R^6e]

group, in which * indicates the point of attachment with the rest of the molecule, and in which $R^{6a}$, $R^{6b}$, $R^{6c}$, $R^{6d}$ represent, independently from each other, a hydrogen or halogen atom; and $R^{6e}$ represents a cyclopropyl-group;

$R^3$ represents a hydrogen atom or a halogen atom, or a —CN, $C_1$-$C_6$-alkyl-, —$(CH_2)_m$—$C_2$-$C_6$-alkenyl, —$(CH_2)_m$—$C_4$-$C_8$-cycloalkenyl —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, R(R')N—$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl, $C_2$-$C_6$-alkenyl-, $C_4$-$C_8$-cycloalkenyl-, $C_2$-$C_6$-alkynyl-, aryl-, —C1-C6-alkyl-aryl, —C1-C6-alkyl-heteroaryl, heteroaryl-, —C(=O)R, —C(=O)N(H)R, —C(=O)N(R)R', —C(=O)O—R, —N(R)R', —$NO_2$, —N(H)C(=O)R or a

[structure: 5-(methylidene)-1-methylpyrrolidin-2-one with * on methylidene]

group, wherein

* indicates the point of attachment with the rest of the molecule;

said $C_1$-$C_6$-alkyl-, —$(CH_2)_m$—$C_2$-$C_6$-alkenyl, —$(CH_2)_m$—$C_4$-$C_8$-cycloalkenyl —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, R(R')N—$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl, $C_2$-$C_6$-alkenyl-, $C_4$-$C_8$-cycloalkenyl-, $C_2$-$C_6$-alkynyl-, aryl-, —C1-C6-alkyl-aryl, —C1-C6-alkyl-heteroaryl, heteroaryl-, —C(=O)R, —C(=O)N(H)R, —C(=O)N(R)R', —C(=O)O—R, —N(R)R', —$NO_2$, —N(H)C

[structure: 5-(methylidene)-1-methylpyrrolidin-2-one with * on methylidene]

group, being optionally substituted, identically or differently, with 1, 2, 3, or 4 $R^8$ groups;

$R^4$ represents a hydrogen atom;

$R^5$ represents a hydrogen atom;

$R^7$ represents a hydrogen or halogen atom, or a —CN, HO—, $C_1$-$C_6$-alkoxy-, $C_1$-$C_6$-alkyl-, halo-$C_1$-$C_6$-alkyl-, halo-$C_1$-$C_6$-alkoxy- R(R')N—$C_1$-$C_6$-alkyl-, HO—$C_1$-$C_6$-alkyl, HO—$C_1$-$C_6$-alkoxy, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)R, —C(=O)N(H)R, —C(=O)N(R)R', —C(=O)O—R, —N(R)R', —$NO_2$, —N(H)C(=O)R, —N(R)C(=O)R', —N(H)C(=O)N(R)R', —N(R)C(=O)N(R')R", —N(H)C(=O)OR, —N(R)C(=O)OR', —N(H)S(=O)R, —N(R)S(=O)R', —N(H)S(=O)$_2$R, —N(R)S(=O)$_2$R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)$_2$R, —S(=O)$_2$N(H)R, —S(=O)$_2$N(R)R', —S(=O)(=NR)R', —S(=O)$_2$-(3- to 7-membered heterocycloalkyl) group;

$R^8$ represents a hydrogen or halogen atom, or a —CN, HO—, $C_1$-$C_6$-alkoxy-, halo-$C_1$-$C_6$-alkoxy-, $C_1$-$C_6$-alkyl-, —$C_1$-$C_6$-alkyl-N(H)C(=O)R, —$C_1$-$C_6$-alkyl-C(=O)N(H)R, —$C_1$-$C_6$-alkyl-C(=O)OR, halo-$C_1$-$C_6$-alkyl-, R(R')N—$C_1$-$C_6$-alkyl-, HO—$C_1$-$C_6$-alkyl, HO—$C_1$-$C_6$-alkoxy, $C_1$-$C_6$-alkoxy-$C_1$-$C_6$-alkyl-, halo-$C_1$-$C_6$-alkoxy-$C_1$-$C_6$-alkyl-, —$C_2$-$C_6$-alkenyl, 3- to 7-membered heterocycloalkyl-, aryl-, heteroaryl-, —C(=O)R, —C(=O)N(H)R, —C(=O)N(R)R', —C(=O)O—R, —N(R)R', —$NO_2$, —N(H)C(=O)R, —N(R)C(=O)R', —N(H)C(=O)N(R)R', —N(R)C(=O)N(R')R", —N(H)C(=O)OR, N(R)C(=O)OR', —N(H)S(=O)R, —N(R)S(=O)R', —N(H)S(=O)$_2$R, —N(R)S(=O)$_2$R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)$_2$R, —S(=O)$_2$N(H)R, —S(=O)$_2$N(R)R', —S(=O)(=NR)R', —S(=O)$_2$-(3- to 7-membered heterocycloalkyl) group;

R, R' and R" are, independently from each other, a hydrogen atom or a $C_1$-$C_6$-alkyl-, —$C_3$-$C_6$-cycloalkyl, $C_3$-$C_6$-alkenyl-, aryl- or a heteroaryl- group;

m is an integer of 0, 1, 2, 3, 4, 5 or 6;

n is an integer of 1, 2, 3, 4 or 5;

or a stereoisomer, a tautomer, an N-oxide, a hydrate, a solvate, or a salt thereof, or a mixture of same.

In accordance with a fourth aspect, the present invention covers compounds of general formula (I), supra, in which:

$R^1$ represents a *$CH_2$—Z moiety, * indicating the point of attachment with the rest of the molecule, wherein Z is a hydrogen atom, or a $C_1$-$C_6$-alkyl-, —$(CH_2)_m$—$C_2$-$C_6$-alkenyl, —$(CH_2)_n$—$C_2$-$C_6$-alkynyl, —$(CH_2)_m$-(3- to 7-membered heterocycloalkyl), halo-$C_1$-$C_6$-alkyl-, HO—$C_1$-$C_6$-alkyl-, $C_2$-$C_6$-alkenyl-, $C_2$-$C_6$-alkynyl-, or heteroaryl-group;

said $C_1$-$C_6$-alkyl-, —$(CH_2)_m$—$C_2$-$C_6$-alkenyl, —$(CH_2)_n$—$C_2$-$C_6$-alkynyl, —$(CH_2)_m$-(3- to 7-membered heterocycloalkyl), halo-$C_1$-$C_6$-alkyl-, HO—$C_1$-$C_6$-alkyl-, $C_2$-$C_6$-alkenyl-, $C_2$-$C_6$-alkynyl-, or heteroaryl- group, is optionally substituted, identically or differently, with 1, 2, 3, or 4 $R^7$ groups;

$R^2$ represents a group

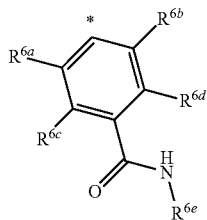

in which * indicates the point of attachment with the rest of the molecule, and in which $R^{6a}$, $R^{6b}$, $R^{6c}$, $R^{6d}$
represent, independently from each other, a hydrogen or halogen atom; and $R^{6e}$ represents a cyclopropyl-group;

$R^3$ represents a —$(CH_2)_m$—$C_2$-$C_6$-alkenyl, —$(CH_2)_m$—$C_4$-$C_8$-cycloalkenyl —$(CH_2)_m$—$C_3$-$C_6$-cycloalkyl, aryl-, heteroaryl-, —N(H)C(=O)R or a

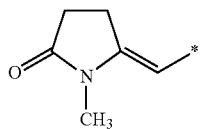

group, wherein
* indicates the point of attachment with the rest of the molecule;
said —$(CH_2)_m$—$C_2$-$C_6$-alkenyl, —$(CH_2)_m$—$C_4$-$C_8$-cycloalkenyl —$(CH_2)_m$—$C_3$-$C_6$-cycloalkyl, aryl-, heteroaryl-, —N(H)C(=O)R or a

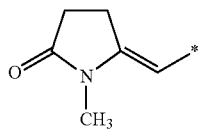

group,
being optionally substituted, identically or differently, with 1, 2, 3, or 4 $R^8$ groups;

$R^4$ represents a hydrogen atom;

$R^5$ represents a hydrogen atom;

$R^7$ represents a hydrogen atom or a —N(H)C(=O)OR, —N(R)C(=O)OR'-group;

$R^8$ represents a hydrogen atom or a $C_1$-$C_6$-alkoxy-$C_1$-$C_6$-alkyl-, —$C_2$-$C_6$-alkenyl, —S(=O)R group;

R, R' and R" are, independently from each other, a hydrogen atom or a —$C_3$-$C_6$-cycloalkyl or heteroaryl- group;

m is an integer of 0, 1;

n is an integer of 1;

or a stereoisomer, a tautomer, an N-oxide, a hydrate, a solvate, or a salt thereof, or a mixture of same.

DETAILED DESCRIPTION OF THE INVENTION

The terms as mentioned in the present text have the following meanings:

The term "halogen atom" or "halo-" is to be understood as meaning a fluorine, chlorine, bromine or iodine atom, preferably a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said halo-$C_1$-$C_6$-alkyl group is, for example, —$CF_3$, —$CHF_2$, —$CH_2F$, —$CF_2CF_3$, or —$CH_2CF_3$.

The term "$C_1$-$C_6$-alkoxy" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —$OCF_3$, —$OCHF_2$, —$OCH_2F$, —$OCF_2CF_3$, or —$OCH_2CF_3$.

The term "$C_1$-$C_6$-alkoxy-$C_1$-$C_6$-alkyl" is to be understood as preferably meaning a linear or branched, saturated, monovalent alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, in which the term "$C_1$-$C_6$-alkyl" is defined supra, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —$CH_2CH_2OCF_3$, —$CH_2CH_2OCHF_2$, —$CH_2CH_2OCH_2F$, —$CH_2CH_2OCF_2CF_3$, or —$CH_2CH_2OCH_2CF_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl) ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-inyl, hex-3-inyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-inyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-inyl.

The term "$C_3$-$C_6$-cycloalkyl" is to be understood as meaning a saturated, monovalent, mono-, or bicyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl, or cyclohexyl or a bicyclic hydrocarbon ring, e.g. a perhydropentalenylene or decalin ring.

The term "$C_4$-$C_8$-cycloalkenyl" is to be understood as preferably meaning a monovalent, mono-, or bicyclic hydrocarbon ring which contains 4, 5, 6, 7 or 8 carbon atoms and one, two, three or four double bonds, in conjugation or not, as the size of said cycloalkenyl ring allows. Said $C_4$-$C_8$-cycloalkenyl group is for example, a monocyclic hydrocarbon ring, e.g. a cyclobutenyl, cyclopentenyl, or cyclohexenyl or a bicyclic hydrocarbon ring, e.g. a cylooctadienyl ring.

The term "3- to 7-membered heterocycloalkyl", is to be understood as meaning a saturated, monovalent, mono- or bicyclic hydrocarbon ring which contains 2, 3, 4, 5, or 6 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl- or halo-$C_1$-$C_6$-alkyl- group; it being possible for said heterocycloalkyl group to be attached to the rest of the molecule via any one of the carbon atoms or, if present, the nitrogen atom.

Particularly, said 3- to 7-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, oxopyrrolidinyl, 2-oxoimidazolidin-1-yl, or a 6-membered ring, such as tetrahydropyranyl, piperidinyl, morpholinyl, dithianyl, thiomorpholinyl, piperazinyl, 1,1-dioxido-1,2-thiazinan-2-yl, or trithianyl, or a 7-membered ring, such as a diazepanyl ring, for example. Optionally, said heterocycloalkyl can be benzo fused.

Said heterocyclyl can be bicyclic, such as, without being limited thereto, a 5,5-membered ring, e.g. a hexahydrocyclopenta[c]pyrrol-2(1H)-yl) ring, or a 5,6-membered bicyclic ring, e.g. a hexahydropyrrolo[1,2-a]pyrazin-2(1H)-yl ring, or for example.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl, or 4H-[1,4]thiazinyl ring, for example, or, it may be benzo-fused, such as, without being limited thereto, a dihydroisoquinolinyl ring, for example.

The term "4- to 8-membered heterocycloalkenyl", is to be understood as meaning an unsaturated, monovalent, mono- or bicyclic hydrocarbon ring which contains 4, 5, 6, or 7 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl- or halo-$C_1$-$C_6$-alkyl- group; it being possible for said heterocycloalkenyl group to be attached to the rest of the molecule via any one of the carbon atoms or, if present, the nitrogen atom. Examples of said heterocycloalkenyl may contain one or more double bonds, e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group, tetrahydropyridinyl, dihydrothiopyranyl, 1-oxido-3,6-dihydro-2H-thiopyran-4-yl, dihydropyranyl, or, it may be benzo fused. The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group, or a 2,3-dihydro-1,4-benzodioxinyl- or 1,3-benzodioxolyl-group.

The term "heteroaryl" is understood as preferably meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

Further, as used herein, the term "$C_4$-$C_8$", as used throughout this text, e.g. in the context of the definition of "$C_4$-$C_8$-cycloalkenyl", is to be understood as meaning a cycloalkenyl group having a finite number of carbon atoms of 4 to 8, i.e. 4, 5, 6, 7 or 8 carbon atoms. It is to be understood further that said term "$C_4$-$C_8$" is to be interpreted as any sub-range comprised therein, e.g. $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$; particularly $C_4$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

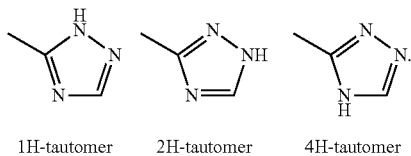

1H-tautomer    2H-tautomer    4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g.

1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In an embodiment of the above-mentioned aspects, the invention relates to compounds of formula (I), wherein:

$R^1$ represents a *$CH_2$—Z moiety, * indicating the point of attachment with the rest of the molecule, wherein Z is a hydrogen atom, or a $C_1$-$C_6$-alkyl-, —$(CH_2)_m$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, R'(R")N—$C_1$-$C_6$-alkyl-, HO—$C_1$-$C_6$-alkyl-, $H_2$N—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl- group;

said $C_1$-$C_6$-alkyl-, —$(CH_2)_m$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, R'(R")N—$C_1$-$C_6$-alkyl-, HO—$C_1$-$C_6$-alkyl-, $H_2$N—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl- group, is optionally substituted, identically or differently, with 1, 2, 3, or 4 $R^7$ groups;

In an embodiment of the above-mentioned aspects, the invention relates to compounds of formula (I), wherein:

$R^2$ represents a

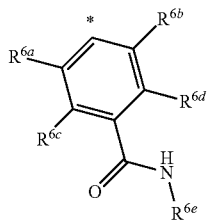

group, in which * indicates the point of attachment with the rest of the molecule, and in which $R^{6a}$, $R^{6b}$, $R^{6c}$, $R^{6d}$ represent, independently from each other, a hydrogen or halogen atom, or a —CN, $C_1$-$C_6$-alkyl-, $C_1$-$C_6$-alkoxy-, halo-$C_1$-$C_6$-alkyl-, R(R')N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —C(=O)R, —C(=O)N(H)R, —C(=O)N(R)R', —C(=O)O—R, —N(R)R', —$NO_2$, —N(H)C(=O)R, —N(R)C(=O)R', —N(H)C(=O)N(R)R', —N(R)C(=O)N(R')R", —N(H)C(=O)OR, —N(R)C(=O)OR', —N(H)S(=O)R', —N(R)S(=O)R', —N(H)S(=O)$_2$R, —N(R)S(=O)$_2$R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)$_2$R, —S(=O)$_2$N(H)R, —S(=O)$_2$N(R)R', S(=O)(=NR)R' group; and $R^{6e}$ represents a cyclopropyl-group being optionally substituted, identically or differently, with 1, 2, 3, or 4 groups selected from: hydrogen, halogen, —OH, —CN, $C_1$-$C_6$-alkyl-, —$C_1$-$C_6$-alkoxy, halo-$C_1$-$C_6$-alkyl-;

In an embodiment of the above-mentioned aspects, the invention relates to compounds of formula (I), wherein:

$R^3$ represents a hydrogen atom or a halogen atom, or a —CN, $C_1$-$C_6$-alkyl-, —$(CH_2)_m$—$C_2$-$C_6$-alkenyl, —$(CH_2)_m$—$C_4$-$C_8$-cycloalkenyl —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, R(R') N—$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl, $C_2$-$C_6$-alkenyl-, $C_4$-$C_8$-cycloalkenyl-, $C_2$-$C_6$-alkynyl-, aryl-, —C1-C6-alkyl-aryl, —C1-C6-alkyl-heteroaryl, heteroaryl-, —C(=O)R, —C(=O)N(H)R, —C(=O)N(R)R', —C(=O)O—R, —N(R)R', —$NO_2$, —N(H)C(=O)R or a

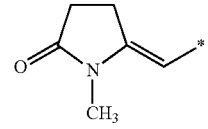

group, wherein

* indicates the point of attachment with the rest of the molecule;

said $C_1$-$C_6$-alkyl-, —$(CH_2)_m$—$C_2$-$C_6$-alkenyl, —$(CH_2)_m$—$C_4$-$C_8$-cycloalkenyl —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), —$(CH_2)_m$-(4- to 8-membered heterocycloalkenyl), aryl-$C_1$-$C_6$-alkyl-, heteroaryl-$C_1$-$C_6$-alkyl-, halo-$C_1$-$C_6$-alkyl-, R(R')N—$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl, $C_2$-$C_6$-alkenyl-, $C_4$-$C_8$-cycloalkenyl-, $C_2$-$C_6$-alkynyl-, aryl-, —C1-C6-alkyl-aryl, —C1-C6-alkyl-heteroaryl, heteroaryl-, —C(=O)R, —C(=O)N(H)R, —C(=O)N(R)R', —C(=O)O—R, —N(R)R', —$NO_2$, —N(H)C(=O)R or

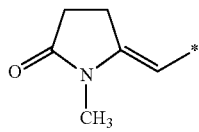 [SMILES: */C=C1\CCC(=O)N1C]

group,
being optionally substituted, identically or differently, with 1, 2, 3, or 4 $R^8$ groups;

In an embodiment of the above-mentioned aspects, the invention relates to compounds of formula (I), wherein:
$R^4$ represents a hydrogen or halogen atom, or a —CN, $C_1$-$C_6$-alkyl- or aryl-group;

In an embodiment of the above-mentioned aspects, the invention relates to compounds of formula (I), wherein:
$R^5$ represents a hydrogen atom;

In an embodiment of the above-mentioned aspects, the invention relates to compounds of formula (I), wherein:
$R^7$ represents a hydrogen or halogen atom, or a —CN, HO—, $C_1$-$C_6$-alkoxy-, $C_1$-$C_6$-alkyl-, halo-$C_1$-$C_6$-alkyl-, halo-$C_1$-$C_6$-alkoxy- R(R')N—$C_1$-$C_6$-alkyl-, HO—$C_1$-$C_6$-alkyl, HO—$C_1$-$C_6$-alkoxy, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)R, —C(=O)N(H)R, —C(=O)N(R)R', —C(=O)O—R, —N(R)R', —NO$_2$, —N(H)C(=O)R, —N(R)C(=O)R', —N(H)C(=O)N(R)R', —N(R)C(=O)N(R')R", —N(H)C(=O)OR, —N(R)C(=O)OR', —N(H)S(=O)R, —N(R)S(=O)R', —N(H)S(=O)$_2$R, —N(R)S(=O)$_2$R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)$_2$R, —S(=O)$_2$N(H)R, —S(=O)$_2$N(R)R', —S(=O)(=NR)R', —S(=O)$_2$-(3- to 7-membered heterocycloalkyl) group;
wherein said 3- to 7-membered heterocycloalkyl- or heteroaryl-, is optionally substituted, identically or differently, with 1, 2, 3, or 4 $C_1$-$C_6$-alkyl- groups In an embodiment of the above-mentioned aspects, the invention relates to compounds of formula (I), wherein:
$R^8$ represents a hydrogen or halogen atom, or a —CN, HO—, $C_1$-$C_6$-alkoxy-, halo-$C_1$-$C_6$-alkoxy-, $C_1$-$C_6$-alkyl-, —$C_1$-$C_6$-alkyl-N(H)C(=O)R, —$C_1$-$C_6$-alkyl-C(=O)N(H)R, —$C_1$-$C_6$-alkyl-C(=O)OR, halo-$C_1$-$C_6$-alkyl-, R(R')N—$C_1$-$C_6$-alkyl-, HO—$C_1$-$C_6$-alkyl, HO—$C_1$-$C_6$-alkoxy, $C_1$-$C_6$-alkoxy-$C_1$-$C_6$-alkyl-, halo-$C_1$-$C_6$-alkoxy-$C_1$-$C_6$-alkyl-, —$C_2$-$C_6$-alkenyl, 3- to 7-membered heterocycloalkyl-, aryl-, heteroaryl-, —C(=O)R, —C(=O)N(H)R, —C(=O)N(R)R', —C(=O)O—R, —N(R)R', —NO$_2$, —N(H)C(=O)R, —N(R)C(=O)R', —N(H)C(=O)N(R)R', —N(R)C(=O)N(R')R", —N(H)C(=O)OR, N(R)C(=O)OR', —N(H)S(=O)R, —N(R)S(=O)R', —N(H)S(=O)$_2$R, —N(R)S(=O)$_2$R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)$_2$R, —S(=O)$_2$N(H)R, —S(=O)$_2$N(R)R', —S(=O)(=NR)R', —S(=O)$_2$-(3- to 7-membered heterocycloalkyl) group;

In an embodiment of the above-mentioned aspects, the invention relates to compounds of formula (I), wherein:
R, R' and R" are, independently from each other, a hydrogen atom or a $C_1$-$C_6$-alkyl-, —$C_3$-$C_6$-cycloalkyl, $C_3$-$C_6$-alkenyl-, aryl- or a heteroaryl- group;

In an embodiment of the above-mentioned aspects, the invention relates to compounds of formula (I), wherein:
m is an integer of 0, 1, 2, 3, 4, 5 or 6;

In an embodiment of the above-mentioned aspects, the invention relates to compounds of formula (I), wherein:
n is an integer of 1, 2, 3, 4 or 5;

In an embodiment of the above-mentioned aspects, the invention relates to compounds of formula (I), wherein:
$R^2$ represents a

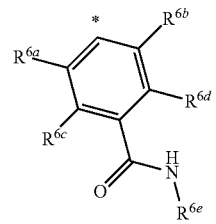

group,
in which * indicates the point of attachment with the rest of the molecule, and in which
$R^{6a}$, $R^{6b}$, $R^{6c}$, $R^{6d}$
represent, independently from each other, a hydrogen or halogen atom; and
$R^{6e}$ represents a cyclopropyl-group;

In an embodiment of the above-mentioned aspects, the invention relates to compounds of formula (I), wherein:
$R^4$ represents a hydrogen atom;

In an embodiment of the above-mentioned aspects, the invention relates to compounds of formula (I), wherein:
$R^1$ represents a *$CH_2$—Z moiety, * indicating the point of attachment with the rest of the molecule,
wherein Z is a hydrogen atom, or a $C_1$-$C_6$-alkyl-, —$(CH_2)_m$—$C_2$-$C_6$-alkenyl, —$(CH_2)_n$—$C_2$-$C_6$-alkynyl, —$(CH_2)_m$-(3- to 7-membered heterocycloalkyl), halo-$C_1$-$C_6$-alkyl-, HO—$C_1$-$C_6$-alkyl-, $C_2$-$C_6$-alkenyl-, $C_2$-$C_6$-alkynyl-, or heteroaryl-group;
said $C_1$-$C_6$-alkyl-, —$(CH_2)_m$—$C_2$-$C_6$-alkenyl, —$(CH_2)_n$—$C_2$-$C_6$-alkynyl, —$(CH_2)_m$-(3- to 7-membered heterocycloalkyl), halo-$C_1$-$C_6$-alkyl-, HO—$C_1$-$C_6$-alkyl-, $C_2$-$C_6$-alkenyl-, $C_2$-$C_6$-alkynyl-, or heteroaryl- group, is optionally substituted, identically or differently, with 1, 2, 3, or 4 $R^7$ groups;

In an embodiment of the above-mentioned aspects, the invention relates to compounds of formula (I), wherein:
$R^2$ represents a group

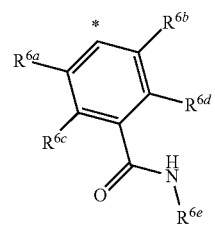

in which * indicates the point of attachment with the rest of the molecule, and in which
$R^{6a}$, $R^{6b}$, $R^{6c}$, $R^{6d}$
represent, independently from each other, a hydrogen or halogen atom; and
$R^{6e}$ represents a cyclopropyl-group;

In an embodiment of the above-mentioned aspects, the invention relates to compounds of formula (I), wherein:
R³ represents a —(CH₂)ₘ—C₂-C₆-alkenyl, —(CH₂)ₘ—C₄-C₈-cycloalkenyl —(CH₂)ₘ—C₃-C₆-cycloalkyl, aryl-, heteroaryl-, —N(H)C(=O)R or a

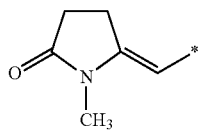

group, wherein
* indicates the point of attachment with the rest of the molecule;
said —(CH₂)ₘ—C₂-C₆-alkenyl, —(CH₂)ₘ—C₄-C₈-cycloalkenyl —(CH₂)ₘ—C₃-C₆-cycloalkyl, aryl-, heteroaryl-, —N(H)C(=O)R or a

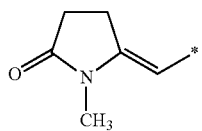

group,
being optionally substituted, identically or differently, with 1, 2, 3, or 4 R⁸ groups;
In an embodiment of the above-mentioned aspects, the invention relates to compounds of formula (I), wherein:
R⁵ represents a hydrogen atom;
In an embodiment of the above-mentioned aspects, the invention relates to compounds of formula (I), wherein:
R⁷ represents a hydrogen atom or a —N(H)C(=O)OR, —N(R)C(=O)OR'-group;
In an embodiment of the above-mentioned aspects, the invention relates to compounds of formula (I), wherein:
R⁸ represents a hydrogen atom or a C₁-C₆-alkoxy-C₁-C₆-alkyl-, —C₂-C₆-alkenyl, —S(=O)R group;
In an embodiment of the above-mentioned aspects, the invention relates to compounds of formula (I), wherein:
R, R' and R" are, independently from each other, a hydrogen atom or a —C₃-C₆-cycloalkyl or heteroaryl- group;
In an embodiment of the above-mentioned aspects, the invention relates to compounds of formula (I), wherein:
m is an integer of 0, 1;
In an embodiment of the above-mentioned aspects, the invention relates to compounds of formula (I), wherein:
n is an integer of 1;
or a stereoisomer, a tautomer, an N-oxide, a hydrate, a solvate, or a salt thereof, or a mixture of same.
In an embodiment of the above-mentioned aspects, the invention relates to compounds of formula (I), according to any of the above-mentioned embodiments, in the form of or a stereoisomer, a tautomer, an N-oxide, a hydrate, a solvate, or a salt thereof, or a mixture of same.
It is to be understood that the present invention relates to any sub-combination within any embodiment of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

In accordance with a further aspect, the present invention covers intermediate compounds which are useful in the preparation of compounds of the present invention of general formula (I), particularly in the method described herein. In particular, the present invention covers:

compounds of general formula (13):

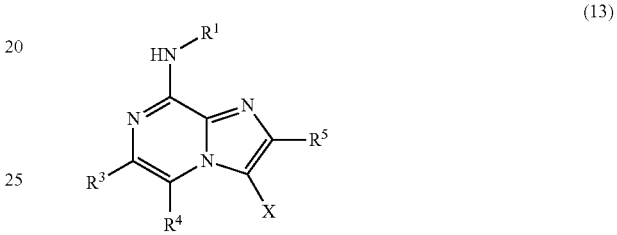

in which R¹, R³, R⁴ and R⁵ are as defined for general formula (I) supra, and Q is a leaving group, such as a chlorine, bromine, or iodine atom;

compounds of general formula (9):

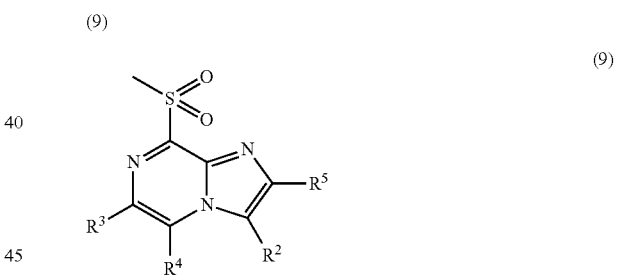

in which R², R³, R⁴ and R⁵ are as defined for general formula (I) supra;
and
compounds of general formula (6):

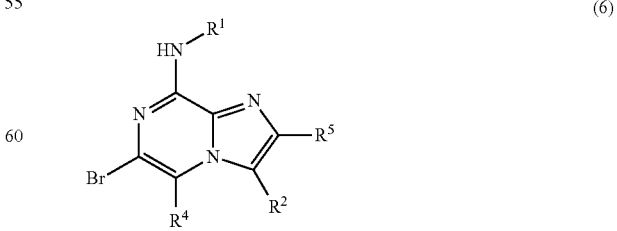

in which R¹, R², R⁴ and R⁵ are as defined for general formula (I) supra.

In accordance with yet another aspect, the present invention covers the use:
- of the intermediate compounds of general formula (13) as defined supra; or
- of the intermediate compounds of general formula (9) as defined supra; or
- of the intermediate compounds of general formula (4) as defined supra; for the preparation of a compound of general formula (I) as defined supra.

EXAMPLES

As mentioned supra, another aspect of the present invention is a method which may be used for preparing the compounds according to the present invention.

The following Table lists the abbreviations used in this paragraph, and in the Examples section. NMR peak forms are stated as they appear in the spectra, possible higher order effects have not been considered.

| Abbreviation | Meaning |
|---|---|
| Ac | acetyl |
| br | broad |
| c- | cyclo- |
| d | doublet |
| dd | doublet of doublets |
| DCM | dichloromethane |
| DIPEA | N,N-diisopropylethylamine |
| DMF | N,N-dimethylformamide |
| DMSO | dimethyl sulfoxide |
| dppf | 1,1'-bis(di-phenylphosphino)ferrocene |
| EDC | N-[3-(dimethylamino)propyl]-N'-ethylcarbodiimide |
| eq | equivalent |
| ESI | electrospray ionisation |
| M | multiplet |
| MS | mass spectrometry |
| MW | molecular weight |
| NBS | N-bromosuccinimide |
| NMP | N-methylpyrrolidinone |
| NMR | nuclear magnetic resonance spectroscopy: chemical shifts (δ) are given in ppm. |
| Pd(dppf)Cl$_2$ | 1,1'-bis(diphenylphosphino)ferrocenedichloropalladium(II) |
| Pd(OAc)$_2$ | palladium(II) acetate |
| POCl$_3$ | phosphoroxychloride |
| P(oTol)$_3$ | tri-o-tolylphosphine |
| q | quartet |
| rt | room temperature |
| RT | retention time in minutes |
| s | singlet |
| sept | septet |
| t | triplet |
| TEA | triethylamine |
| TFA | trifluoroacetic acid |
| THF | tetrahydrofuran |
| UPLC | ultra performance liquid chromatography |

The schemes and procedures described below illustrate general synthetic routes to the compounds of general formula (I) of the invention and are not intended to be limiting. It is obvious to the person skilled in the art that the order of transformations as exemplified in the Schemes can be modified in various ways. The order of transformations exemplified in the Schemes is therefore not intended to be limiting. In addition, interconversion of any of the substituents, $R^1$, $R^2$, $R^3$, $R^4$, or $R^5$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3$^{rd}$ edition, Wiley 1999). Specific examples are described in the subsequent paragraphs. Further, it is possible that two or more successive steps may be performed without work-up being performed between said steps, e.g. a "one-pot" reaction, as is well-known to the person skilled in the art.

A first reaction scheme is outlined infra:
Synthesis of Compounds of General Formula (I)

Scheme 1

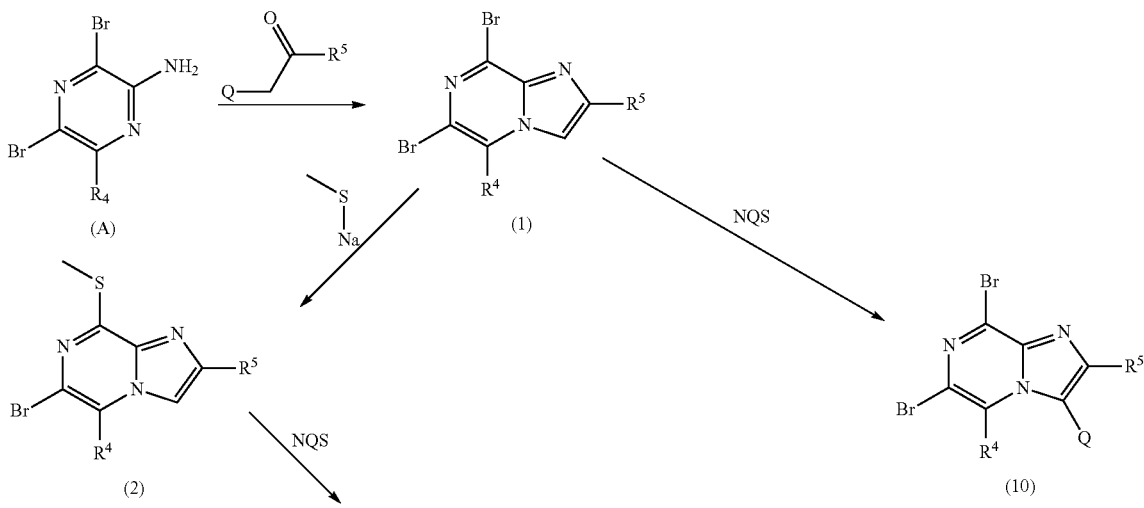

-continued

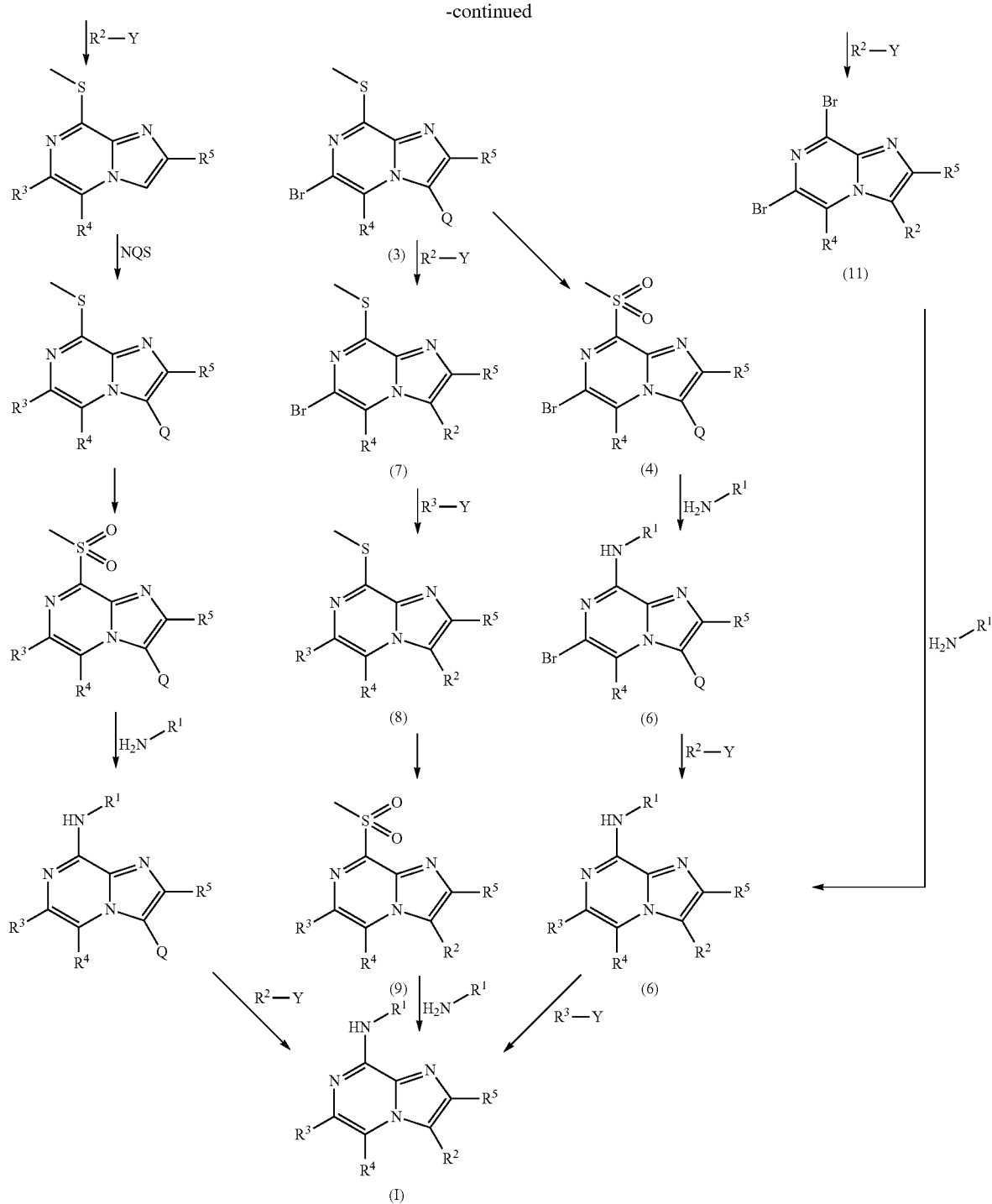

wherein $R^1$, $R^2$, $R^3$, $R^4$, and $R^5$ have the meaning as given for general formula (I), supra, and Y represents a "suitable functional group" via which the $R^2$ of the $R^2$—Y compound can be coupled, by a coupling reaction, onto the Q-bearing carbon atom of a compound, thereby replacing said Q with said $R^2$ moiety.

Compounds of general formula (I) can be synthesised according to the procedures depicted in Scheme 1. The scheme exemplifies the main routes that allow variations in position NH—$R^1$, $R^2$ and $R^3$ as last step of the synthesis.

Here, mainly variations in position NH—$R^1$ and $R^3$ were made. Moreover, also other routes were used for synthesis of the target compounds.

Key reaction for introduction of NH—$R^1$ are nucleophilic substitutions of 8-halo or 8-sulfonyl precursors, i. e. by reaction with suitable amines in the presence of a suitable base, such as, for example DIPEA in a suitable solvent such as DMF, or NMP, at temperatures ranging from room temperature to the boiling point (i. e. reactions (4) to (5), (11) to (6), (9) to (I).

Introduction of $R^2$ moieties in position 3 is achieved from suitable 3-halo precursors by a coupling reaction, for example, particularly a metal-catalysed coupling reaction, with a compound of formula $R^2$—Y, in which $R^2$ is as defined as for compounds of general formula (I) supra, and Y represents a "suitable functional group" via which the $R^2$ of the $R^2$—Y compound can be coupled onto the Q-bearing carbon atom of a compound, thereby replacing said Q with said $R^2$ moiety (i. e. reactions (3) to (7), (5) to (6), (10) to (11)). Examples of such "suitable functional groups", Y in $R^2$—Y include boronic acids, $R^2$—B(OH)$_2$, or boronic esters, $R^2$—B(OC$_1$-C$_6$-alkyl)$_2$. Examples of "such suitable groups Q" include chlorine, bromine and iodine. Examples of such coupling reactions may be found in the textbook entitled "Metal-Catalyzed Cross-Coupling Reactions", Armin de Meijere (Editor), François Diederich (Editor) September 2004, Wiley Interscience ISBN: 978-3-527-30518-6. Said coupling reactions take place optionally in the presence of a suitable catalyst, such as Pd(OAc)$_2$ and P(oTol)$_3$ for example, and optionally with a suitable base, such as potassium carbonate for example, optionally in a suitable solvent, such as THF for example.

Introduction of $R^3$ moieties can be achieved by various reactions of $R^3$—Y including the coupling reactions used for $R^2$ moieties.

Further examples of such "suitable functional groups" Y include:
  a hydrogen atom which can be activated in a coupling reaction, for example an olefinic hydrogen atom, e.g. —C(H)=C(H)—H, or,
  a hydrogen atom which may be abstracted, for example with a base: an example of such a compound is aryl-O—H, where aryl-O is an example of an $R^3$.

The corresponding reactions include other palladium catalyzed coupling reactions like Sonogashira coupling reactions with alkynes for alkyne introduction, Heck coupling reactions with alkenes for alkene introduction, Hartwig Buchwald coupling reactions with amines for amine introduction. Ethers and thioethers can be introduced by reaction with suitable alcohols or thiols in presence of a base, for example sodium hydride, in a suitable solvent, such as DMSO, at temperatures ranging from rt to the boiling point.

The starting material, 6-substituted 3,5-dibromo-pyrazin-2-ylamine intermediates of general formula (A) may be commercially available or can be synthesized according procedures known to persons skilled in the art. Alternatively, $R^4$ substituents in position 6 can also be incorporated at a later stage of the synthesis route to the target compounds.

Intermediates of formula (A) can be converted to the corresponding 6,8-dibromo-imidazo[1,2-a]pyrazine intermediate of general formula (1) by reaction with an alpha-halo-keto derivative, for example 2-bromo-1,1-diethoxy-ethane in a suitable solvent system, such as, for example, THF and water, at temperatures ranging from room temperature to the boiling point of the solvent.

8-thiomethylimidazo[1,2-a]pyrazine intermediates can be obtained by conversion of 8-halo precursors with sodium thiomethylate in the presence of a suitable solvent, such as DMF at temperatures ranging from −20° C. to the boiling point of the solvent (reaction (1) to (2)).

8-methanesulfonyl-imidazo[1,2-a]pyrazine intermediates can be obtained from 8-thiomethyl imidazopyrazine precursors by reaction with an oxidizing agent such as, for example, meta-chloro perbenzoic acid in a suitable solvent such as DCM, at temperatures ranging from room temperature to the boiling point (reactions (3) to (4), (8) to (9)).

3-halo-imidazo[1,2-a]pyrazine intermediates can be obtained from suitable 3-hydrogen precursors by reaction with a suitable halogenation agent NQS, such as NIS for example, in the presence of a suitable solvent, such as DMF at temperatures ranging from room temperature to the boiling point of the solvent (reactions (1) to (10), (2) to (3)).

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be removed by stirring using a suitable solvent. In some cases, the compounds may be purified by chromatography, particularly flash chromatography, using for example pre-packed silica gel cartridges, e.g. from Separtis such as Isolute® Flash silica gel or Isolute® Flash NH$_2$ silica gel in combination with a suitable chromatographic system such as a Flashmaster II (Separtis) or an Isolera system (Biotage) and eluents such as, for example, gradients of hexane/EtOAc or DCM/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluants such as, for example, gradients of water and acetonitrile which may contain additives such as trifluoroacetic acid, formic acid or aqueous ammonia.

Analytical UPLC-MS was performed as follows:

Method A: System: UPLC Acquity (Waters) with PDA Detector and Waters ZQ mass spectrometer; Column: Acquity BEH C18 1.7 μm 2.1×50 mm; Temperature: 60° C.; Solvent A: Water+0.1% formic acid; Solvent B: acetonitrile; Gradient: 99% A→1% A (1.6 min)→1% A (0.4 min); Flow: 0.8 mL/min; Injection Volume: 1.0 μl (0.1 mg-1 mg/mL sample concentration); Detection: PDA scan range 210-400 nm—Fixed and ESI (+), scan range 170-800 m/z Names of compounds were generated using the Autonom 2000 add-in of ISIS/Draw [MDL Information Systems Inc. (Elsevier MDL)] or the ICS naming tool of ACD labs.

Numbering of intermediates in Scheme 1 and Scheme 2 matches the numbers of the following intermediate examples.

Intermediate Example 1-1

Preparation of 6,8-dibromo-imidazo[1,2-a]pyrazine

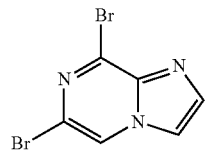 [SMILES: Brc1cn2ccnc2c(Br)n1]

To a stirred suspension of 2-amino-3,5-dibrompyrazine (427 g, 1688 mmol) in water (6.4 L)/THF (482 mL), at rt was added bromacetaldehyde-diethylacetal (998 g, 5065 mmol) in one portion. After stirring under reflux for 4 h, the clear orange solution was stirred for an additional 15 h at rt. The suspension was filtered, and the remaining solid was washed with MeOH (2 L) and dried in vaccuo at 60° C. to yield 6,8-dibromo-imidazo[1,2-a]pyrazine as an off-white solid (500 g, 107% with residual MeOH): $^1$H-NMR (300 MHz, d$_6$-DMSO): δ=9.02 (s, 1H), 8.23 (d, 1H), 7.89 (d, 1H) ppm. UPLC-MS: RT=0.80 min; m/z 277.9 [MH$^+$]; required MW=276.9.

Intermediate Example 1-2

Preparation of (6,8-dibromoimidazo[1,2-a]pyrazin-2-yl)methanol

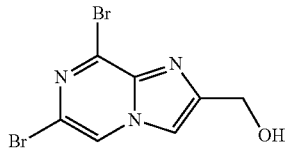 [SMILES: OCc1cn2cc(Br)nc(Br)c2n1]

Step A: Preparation of ethyl 6,8-dibromoimidazo[1,2-a]pyrazine-2-carboxylate

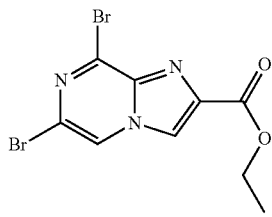

To a stirred solution of 2-amino-3,5-dibrompyrazine (20 g, 79 mmol) in dimethylcarbonate (133 mL) at rt was added ethyl 3-bromo-2-oxopropanoate (17.14 g, 79 mmol) in one portion. After stirring at 110° C. for 3 h, the solution was stirred at rt overnight. Water and DCM were added and the aqueous phase was extracted with DCM. After washing of the organic phase with water, drying over $Na_2(SO_4)$ and filtration the organic phase was evaporated. Flash chromatography yielded 13.95 g (50.6%) ethyl 6,8-dibromoimidazo[1,2-a]pyrazine-2-carboxylate: $^1$H-NMR (300 MHz, $CDCl_3$): δ=8.30 (s, 1H), 8.27 (s, 1H), 4.48 (q, 2H), 1.43 (tr, 3H) ppm.

Step B: Preparation of (6,8-dibromoimidazo[1,2-a]pyrazin-2-yl)methanol

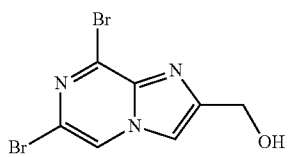

To a stirred solution of ethyl 6,8-dibromoimidazo[1,2-a]pyrazine-2-carboxylate (13.95 g, 40 mmol) in toluene (558 mL) at 0° C. was added 80 mL DIBAH (120 mmol, 3 eq, 1.5M in toluene) dropwise. After stirring overnight at rt, the solution was poured on 1M HCl, extracted with ethyl acetate and the organic phase was washed with water, sole, dried over sodium sulphate and filtered. Removal of the solvent and recrystallyzation from DCM yielded 5.55 g (45.2%) (6,8-dibromoimidazo[1,2-a]pyrazin-2-yl)methanol: $^1$H-NMR (300 MHz, $d_6$-DMSO): δ=8.93 (s, 1H), 8.05 (s, 1H), 5.46 (bs, 1H), 4.63 (s, 2H) ppm. UPLC-MS: RT=0.73 min; m/z 308.0 [MH$^+$]; required MW=307.0.

Intermediate Example 2-1

Preparation of 6-bromo-8-methylsulfanyl-imidazo[1,2-a]pyrazine

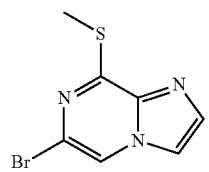

To a stirred suspension of intermediate example 1-1 6,8-dibromo-imidazo[1,2-a]pyrazine (489 g, 1766 mmol) in MeOH (2900 mL) at −20° C. was dropwise added a solution of sodium urethan thiolate (225 g, 3214 mmol, 1.8 eq) in 800 mL water. After stirring overnight, the clear solution was poured on 30 L water and the yellowish precipitate was filtered, washed with 3 L water and dried in vaccuo to yield 301 g 6-bromo-8-methylsulfanyl-imidazo[1,2-a]pyrazine (69.8%). $^1$H-NMR (300 MHz, $d_6$-DMSO): δ=8.64 (1H, s), 8.00 (1H, d), 7.66 (1H, d 2.54 (3H, s) ppm.

Intermediate Example 3-1

Preparation of 6-bromo-3-iodo-8-methylsulfanyl-imidazo[1,2-a]pyrazine

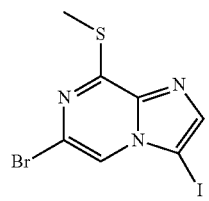

To a stirred solution of 6-bromo-8-methylsulfanyl-imidazo[1,2-a]pyrazine (210.0 g, 860.3 mmol) in DMF (4200 mL) was added NIS (212.9 g, 946.3 mmol, 1.1 eq) in one portion at rt. After 18 h stirring at 60° C. the dark solution was evaporated and the brown residue was dissolved in DCM (7 L), washed with water (2×5 L) and sole (2×5 L) and dried over sodium sulphate. Crystallization by careful removal of solvent yielded 255 g (80.1%) 6-bromo-3-iodo-8-methylsulfanyl-imidazo[1,2-a]pyrazine: $^1$H-NMR (300 MHz, $d_6$-DMSO): δ=8.24 (1H, s), 7.79 (1H, s), 2.46 (3H, s) ppm.

Intermediate Example 4-1

Preparation of 6-bromo-3-iodo-8-methanesulfonyl-imidazo[1,2-a]pyrazine

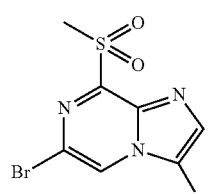

To a stirred solution of 6-bromo-3-iodo-8-methylsulfanyl-imidazo[1,2-a]pyrazine (100.0 g, 270.3 mmol) in DCM (2000 mL) was added meta-chloro perbenzoic acid (116.6 g, 675.6 mmol, 2.5 eq) in several portions at 0° C. After stirring for 1 h at rt, another equivalent of meta-chloro perbenzoic acid (46.64 g, 270.3 mmol) was added and the mixture was stirred overnight. The suspension was filtered and the organic phase was washed with water (2 L), saturated NaHCO3 solution (2 L), sole (2 L), dried over sodium sulphate, filtered and evaporated to yield 197 g of an orange solid. The solid was refluxed in ethanole (300 mL) for 15 min, filtered and dried at 50° C. in vaccuo to yield 104.5 g (96.2%) 6-bromo-3-iodo-8-methanesulfonyl-imidazo[1,2-a]pyrazine as a yellowish solid: $^1$H-NMR (300 MHz, CDCl$_3$): δ=8.45 (1H, s), 8.07 (1H, s), 3.54 (3H, s) ppm.

Intermediate Example 5-1

Preparation of (6-bromo-3-iodo-imidazo[1,2-a]pyrazin-8-yl)-isobutyl-amine

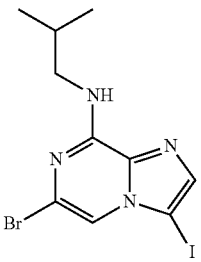 [SMILES: CC(C)CNc1nc(Br)cn2c(I)cnc12]

To a stirred solution of 6-bromo-3-iodo-8-methanesulfonyl-imidazo[1,2-a]pyrazine (5.08 g, 12.64 mmol) in NMP (100 mL) was added 3.77 mL isobutylamine (2.77 g, 37.90 mmol, 3 eq) in one portion at rt. After stirring for 2 h at rt, 500 mL water was added and the mixture was extracted with ethyl acetate (3×200 mL). The organic phase was filtered, evaporated and the residue was recrystallized from MeOH/water to yield 3.87 g (77.52%) (6-bromo-3-iodo-imidazo[1,2-a]pyrazin-8-yl)-isobutyl-amine: $^1$H-NMR (300 MHz, d$_6$-DMSO): δ=8.09 (1H, tr), 7.60 (1H, s), 7.54 (1H, s), 3.19 (2H, dd), 1.95 (1H, m), 0.85 (6H, d) ppm.

Intermediate Example 6-1

Preparation of 4-(6-bromo-8-isobutylamino-imidazo[1,2-a]pyrazin-3-yl)-N-cyclopropyl-benzamide

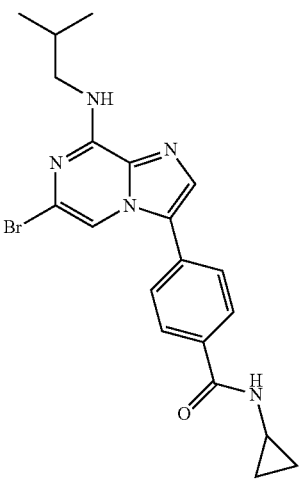 [SMILES: CC(C)CNc1nc(Br)cn2c(-c3ccc(C(=O)NC4CC4)cc3)cnc12]

To a stirred solution of (6-bromo-3-iodo-imidazo[1,2-a]pyrazin-8-yl)-isobutyl-amine (74.20 g, 188 mmol) in dioxane (1300 mL) was subsequently added 130 mL water, 119 g tripotassium phosphate (563 mmol, 3 eq), 50.06 g [4-[(cyclopropylamino)carbonyl]phenyl]-boronic acid (244 mmol, 1.3 eq) and 7.42 g Pd(dppf)Cl$_2$ (9 mmol, 0.05 eq) in one portion at rt under argon atmosphere. After stirring for 72 h at 40° C., the mixture was poured on 5 L water and the precipitate was filtered off and washed with water. The precipitate was taken up in DCM, washed with sat. sodium chloride solution, dried over sodium sulphate and after filtration the solvent was evaporated. Purification by flash chromatography (DCM/acetone 95:5) yielded 45.2 g (56.20%) 4-(6-bromo-8-isobutylamino-imidazo[1,2-a]pyrazin-3-yl)-N-cyclopropyl-benzamide: $^1$H-NMR (300 MHz, CDCl$_3$): δ=7.90 (2H, d), 7.65 (1H, s), 7.58 (2H, d), 7.56 (1H, s), 6.32 (1H, s), 6.20 (1H, tr), 3.46 (2H, dd), 2.95 (1H, m), 2.01 (1H, m), 1.04 (6H, d), 0.92 (2H, m), 0.66 (2H, m) ppm.

Intermediate Example 6-2

Preparation of 4-[6-Bromo-2-(hydroxymethyl)-8-(isobutylamino)imidazo[1,2-a]pyrazin-3-yl]-N-cyclopropylbenzamide

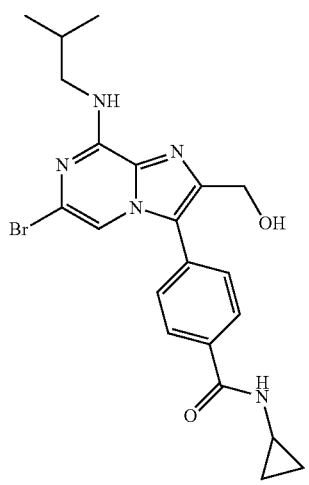 [SMILES: CC(C)CNc1nc(Br)cn2c(-c3ccc(C(=O)NC4CC4)cc3)c(CO)nc12]

To a solution of 50 mg (107 μmol) N-cyclopropyl-4-[6,8-dibromo-2-(hydroxymethyl)imidazo[1,2-a]pyrazin-3-yl]benzamide in 0.71 mL N,N-dimethylformamide were added 32 μL 2-methylpropan-1-amine and the mixture was stirred at 23° C. for 3 hours. Toluene was added and the solvents removed. The residue was purified by chromatography to give 40.7 mg (83%) of the title compound. $^1$H-NMR (300 MHz d$_6$-DMSO): δ=8.52 (1H, d), 8.12 (1H, t), 7.95 (2H, d), 7.68 (2H, d), 7.50 (1H, s), 5.18 (1H, t), 4.46 (2H, d), 3.23 (2H, m), 2.85 (1H, m), 2.00 (1H, m), 0.87 (6H, m), 0.68 (2H, m), 0.55 (2H, m) ppm. UPLC-MS: RT=1.18 min; m/z 459.4 [MH$^+$]; required MW=458.4.

The following intermediates were prepared analogously to the procedure described above using the appropriate intermediate example 11 and the appropriate amine [LC-MS data such as retention time (RT in min) or observed mass peak were collected using LC-MS Method A unless explicitly stated]:

| Intermediate Example | Structure | Name | Supporting Data |
|---|---|---|---|
| 6-3 | 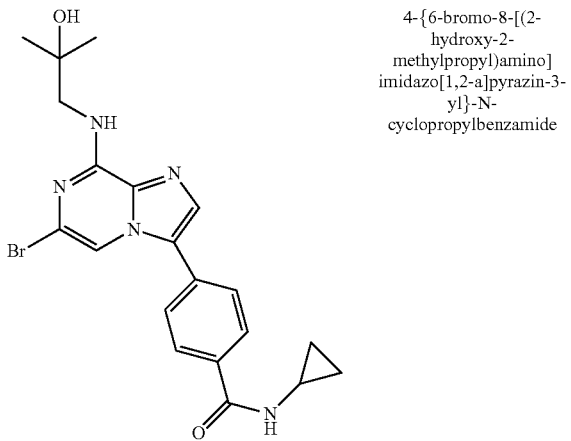 | 4-{6-bromo-8-[(2-hydroxy-2-methylpropyl)amino]imidazo[1,2-a]pyrazin-3-yl}-N-cyclopropylbenzamide | Yield: 527 mg (74%) |
| 6-4 | 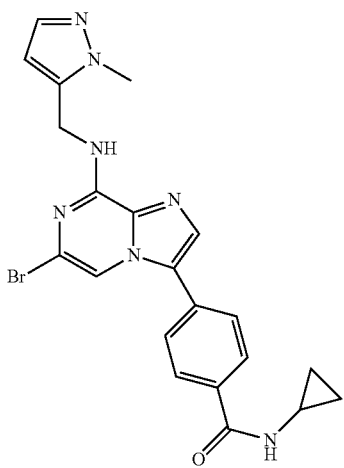 [SMILES: Cn1nccc1CNc1nc(Br)cn2c(-c3ccc(C(=O)NC4CC4)cc3)cnc12] | 4-(6-Bromo-8-{[(1-methyl-1H-pyrazol-5-yl)methyl]amino}imidazo[1,2-a]pyrazin-3-yl)-N-cyclopropylbenzamide | Yield: 68 mg (63%) |

| Intermediate Example | Structure | Name | Supporting Data |
|---|---|---|---|
| 6-5 | 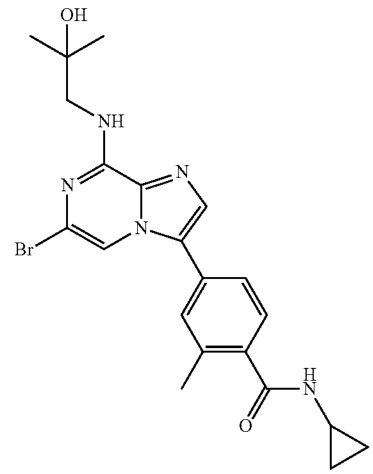 [SMILES: Cc1cc(-c2cnc3c(NCC(C)(C)O)nc(Br)cn23)ccc1C(=O)NC1CC1] | -{6-bromo-8-[(2-hydroxy-2-methylpropyl)amino]imidazo[1,2-a]pyrazin-3-yl}-N-cyclopropyl-2-methylbenzamide | Yield: 415 mg (85%) |
| 6-6 | 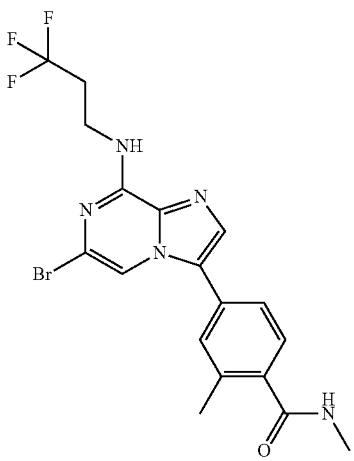 [SMILES: CNC(=O)c1ccc(-c2cnc3c(NCCC(F)(F)F)nc(Br)cn23)cc1C] | 4-{6-bromo-8-[(3,3,3-trifluoropropyl)amino]imidazo[1,2-a]pyrazin-3-yl}-N-cyclopropyl-2-methylbenzamide | Yield: 464 mg (90%) |

Intermediate Example 6-7

Preparation of 4-{6-bromo-8-[(2-methylpropyl)amino]imidazo[1,2-a]pyrazin-3-yl}-2-chloro-N-cyclopropylbenzamide

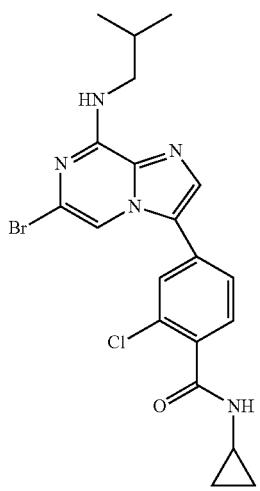 [SMILES: CC(C)CNc1nc(Br)cn2c(-c3ccc(C(=O)NC4CC4)c(Cl)c3)cnc12]

To a stirred solution of 6-bromo-3-iodo-8-methanesulfonyl-imidazo[1,2-a]pyrazine (4.02 g, 10 mmol) in THF (50 mL) was added 1.47 g isobutylamine (20 mmol, 2 eq) in one portion at rt. After stirring overnight, 30 mL 1M potassium carbonate solution (30 mmol, 3 eq), 3.72 g [3-chloro-4-(cyclopropylcarbamoyl)phenyl]boronic acid (15 mmol, 1.5 eq) and 0.81 g Pd(dppf)Cl$_2$ (1 mmol, 0.1 eq) were subsequently added at rt. After stirring for 96 h at 65° C., the mixture was concentrated in vaccuo, taken up in ethyl acetate and washed with water. After drying over sodium sulphate and filtration, the solvent was evaporated. Purification by flash chromatography (ethyl acetate/hexane) yielded 1.88 g (62.20%) 4-{6-bromo-8-[(2-methylpropyl)amino]imidazo[1,2-a]pyrazin-3-yl}-2-chloro-N-cyclopropylbenzamide. $^1$H-NMR (300 MHz, d$_6$-DMSO): δ=8.51 (1H, d), 8.11 (1H, t), 7.77 (1H, s), 7.74 (1H, s), 7.71 (1H, s), 7.64 (1H, d), 7.51 (1H, d), 3.23 (2H, t), 2.80 (1H, m), 1.99 (1H, m), 0.87 (6H, d), 0.67 (2H, m), 0.50 (2H, m) ppm. UPLC-MS: RT=1.33 min; m/z 463.8 [MH$^+$]; required MW=462.8.

The following intermediates were prepared analogously to the procedure described above using the appropriate amine and the appropriate boronic acid derivative [LC-MS data such as retention time (RT in min) or observed mass peak were collected using LC-MS Method A unless explicitly stated]:

| Intermediate Example | Structure | Name | Supporting Data |
|---|---|---|---|
| 6-8 | 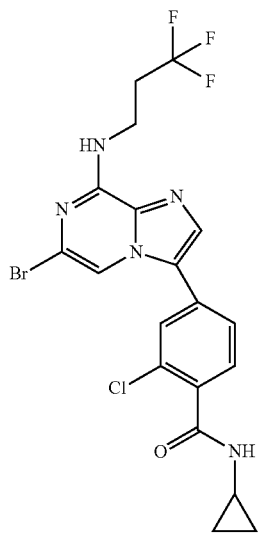 [SMILES: O=C(NC1CC1)c1ccc(-c2cnc3c(NCCC(F)(F)F)nc(Br)cn23)cc1Cl] | 4-{6-bromo-8-[(3,3,3-trifluoropropyl)amino]imidazo[1,2-a]pyrazin-3-yl}-2-chloro-N-cyclopropylbenzamide | Yield: 1.16 g (23%) |
| 6-9 | 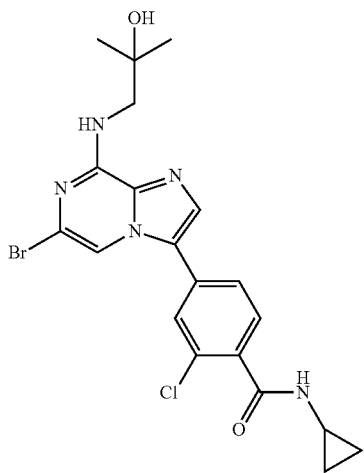 [SMILES: CC(C)(O)CNc1nc(Br)cn2c(-c3ccc(C(=O)NC4CC4)c(Cl)c3)cnc12] | 4-{6-bromo-8-[(2-hydroxy-2-methylpropyl)amino]imidazo[1,2-a]pyrazin-3-yl}-2-chloro-N-cyclopropylbenzamide | Yield: 3.21 g (67%) |
| 6-10 | 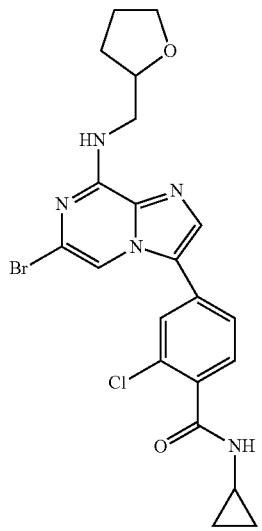 [SMILES: O=C(NC1CC1)c1ccc(-c2cnc3c(NCC4CCCO4)nc(Br)cn23)cc1Cl] | 4-{6-bromo-8-[(tetrahydrofuran-2-ylmethyl)amino]imidazo[1,2-a]pyrazin-3-yl}-2-chloro-N-cyclopropylbenzamide | Yield: 2.00 g (41%) |

| Intermediate Example | Structure | Name | Supporting Data |
|---|---|---|---|
| 6-11 | 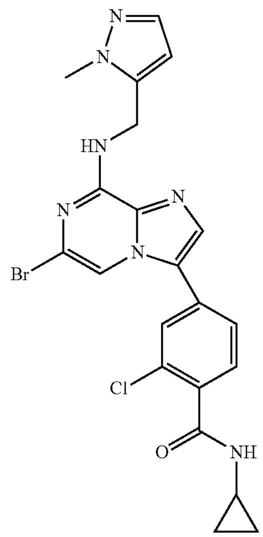 [SMILES: Cn1nccc1CNc1nc(Br)cn2c(-c3ccc(C(=O)NC4CC4)c(Cl)c3)cnc12] | 4-(6-bromo-8-{[(1-methyl-1H-pyrazol-5-yl)methyl]amino}imidazo[1,2-a]pyrazin-3-yl)-2-chloro-N-cyclopropylbenzamide | Yield: 889 mg (18%) |
| 6-12 | 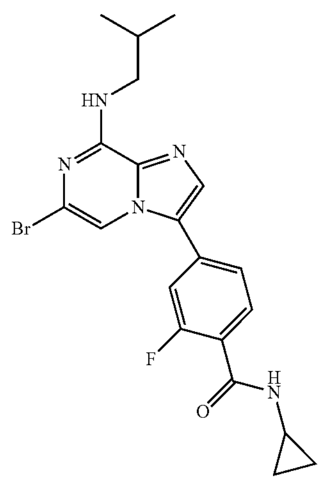 [SMILES: CC(C)CNc1nc(Br)cn2c(-c3ccc(C(=O)NC4CC4)c(F)c3)cnc12] | 4-{6-bromo-8-[(2-methylpropyl)amino]imidazo[1,2-a]pyrazin-3-yl}-N-cyclopropyl-2-fluorobenzamide | Yield: 2.48 g (56%) |
| 6-13 | 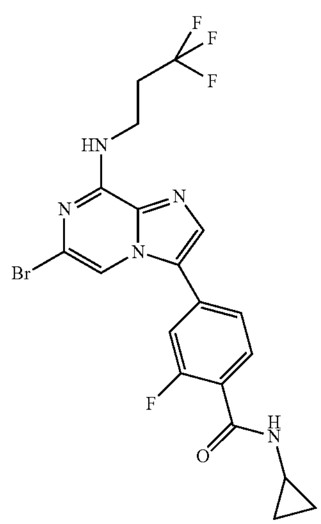 [SMILES: O=C(NC1CC1)c1ccc(-c2cnc3c(NCCC(F)(F)F)nc(Br)cn23)cc1F] | 4-{6-bromo-8-[(3,3,3-trifluoropropyl)amino]imidazo[1,2-a]pyrazin-3-yl}-N-cyclopropyl-2-fluorobenzamide | Yield: 2.00 g (41%) |

| Intermediate Example | Structure | Name | Supporting Data |
|---|---|---|---|
| 6-14 | 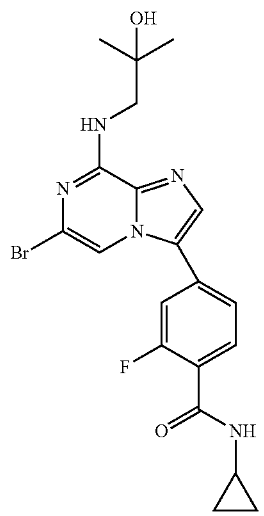 [SMILES: CC(C)(O)CNc1nc(Br)cn2c(-c3ccc(C(=O)NC4CC4)c(F)c3)cnc12] | 4-{6-bromo-8-[(2-hydroxy-2-methylpropyl)amino]imidazo[1,2-a]pyrazin-3-yl}-N-cyclopropyl-2-fluorobenzamide | Yield: 2.53 g (55%) |
| 6-15 | 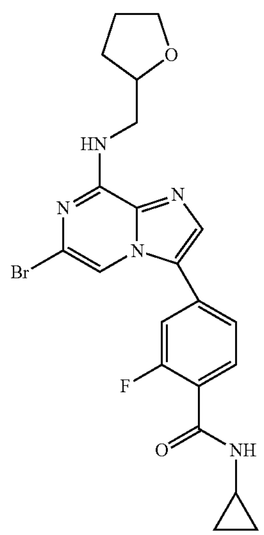 | 4-{6-bromo-8-[(tetrahydrofuran-2-ylmethyl)amino]imidazo[1,2-a]pyrazin-3-yl}-N-cyclopropyl-2-fluorobenzamide | Yield: 2.33 g (49%) |
| 6-16 | 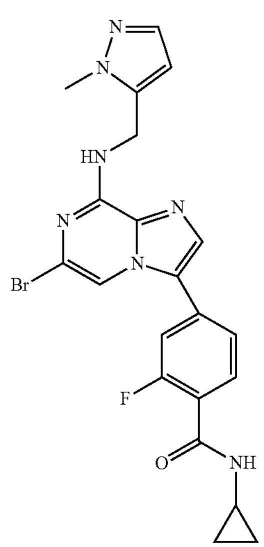 | 4-(6-bromo-8-{[(1-methyl-1H-pyrazol-5-yl)methyl]amino}imidazo[1,2-a]pyrazin-3-yl)-N-cyclopropyl-2-fluorobenzamide | Yield: 3.51 g (72%) |

Intermediate Example 7-1

Preparation of 4-(6-bromo-8-methylsulfanyl-imidazo[1,2-a]pyrazin-3-yl)-N-cyclopropyl-benzamide

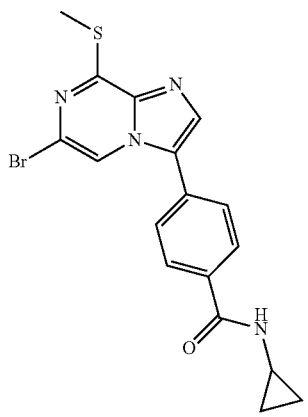 [SMILES: CSc1nc(Br)cn2c(-c3ccc(C(=O)NC4CC4)cc3)cnc12]

To a stirred solution of intermediate example 3-1 6-bromo-3-iodo-8-methylsulfanyl-imidazo[1,2-a]pyrazine (25.00 g, 67.6 mmol) in THF (214 mL) and water (100 mL) was subsequently added 43 g tripotassium phosphate (203 mmol, 3 eq), 18.01 g [4-[(cyclopropylamino)carbonyl]phenyl]-boronic acid (87.8 mmol, 1.3 eq) and 5.52 g Pd(dppf)Cl$_2$ (6.8 mmol, 0.1 eq) in one portion at rt under argon atmosphere. After stirring overnight at 45° C., ethyl acetate was added and the organic phase was washed with sat. sodium chloride solution, dried over sodium sulphate and filtered. After removal of the solvent, purification by flash chromatography (n-hexane/ethyl acetate 85:15) yielded 15.33 g (56.26%) 4-(6-bromo-8-methylsulfanyl-imidazo[1,2-a]pyrazin-3-yl)-N-cyclopropyl-benzamide: $^1$H-NMR (300 MHz, CDCl$_3$): δ =8.07 (1H, s), 7.92 (2H, d), 7.77 (1H, s), 7.60 (2H, d), 6.32 (1H, bs), 2.95 (1H, m), 2.70 (3H, s), 0.92 (2H, m), 0.67 (2H, m) ppm. UPLC-MS: RT=1.12 min; m/z 404.3 [MH$^+$]; required MW=403.3.

Intermediate Example 8-1

Preparation of N-cyclopropyl-4-(8-methylsulfanyl-6-phenyl-imidazo[1,2-a]pyrazin-3-yl)-benzamide

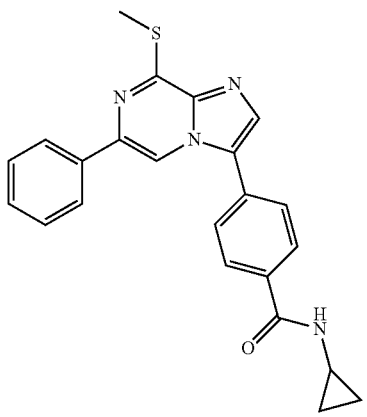 [SMILES: CSc1nc(-c2ccccc2)cn2c(-c3ccc(C(=O)NC4CC4)cc3)cnc12]

To a stirred solution of 4-(6-bromo-8-methylsulfanyl-imidazo[1,2-a]pyrazin-3-yl)-N-cyclopropyl-benzamide (7.34 g, 18.2 mmol) in n-propanol (270 mL) and NMP (15 mL) was subsequently added 27.3 mL 2M potassium carbonate solution, 4.44 g phenylboronic acid (36.4 mmol, 2 eq), triphenylphosphine (238.7 mg, 0.91 mmol, 0.05 eq), 1.28 g bis(triphenylphosphin)palladium(II)chloride (1.82 mmol, 0.1 eq) in one portion at rt under argon atmosphere. After stirring for 2 h at 120° C., the mixture was concentrated in vaccuo (50% v/v), triturated with water and extracted with DCM. The organic phase was dried over sodium sulphate, filtered and the solvent was evaporated. Purification by flash chromatography (ethyl acetate/n-hexane) followed by crystallization from ethyl acetate yielded 5.87 g (80.5%)N-Cyclopropyl-4-(8-methylsulfanyl-6-phenyl-imidazo[1,2-a]pyrazin-3-yl)-benzamide: $^1$H-NMR (300 MHz, CDCl$_3$): δ=8.30 (1H, s), 7.94 (4H, d), 7.77 (1H, s), 7.65 (2H, d), 7.50-7.37 (3H, m), 6.38 (1H, bs), 2.95 (1H, m), 2.80 (3H, s), 1.04 (6H, d), 0.92 (2H, m), 0.67 (2H, m) ppm.

Intermediate Example 8-2

Preparation of N-cyclopropyl-4-(8-methanesulfanyl-6-pyridin-4-yl-imidazo[1,2-a]pyrazin-3-yl)-benzamide

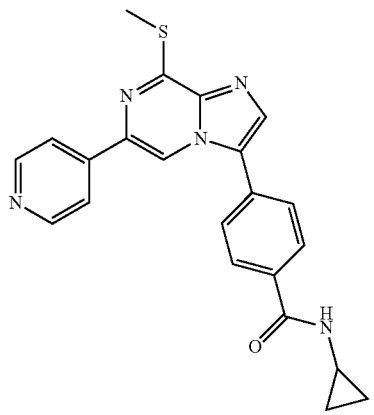 [SMILES: CSc1nc(-c2ccncc2)cn2c(-c3ccc(C(=O)NC4CC4)cc3)cnc12]

To a stirred solution of 4-(6-bromo-8-methylsulfanyl-imidazo[1,2-a]pyrazin-3-yl)-N-cyclopropyl-benzamide (12.1 g, 30 mmol) in THF (120 mL) was subsequently added 90 mL 1M potassium carbonate solution (90 mmol, 3 eq), 18.4 g 4-pyridylboronic acid (150 mmol, 5 eq) and 2.45 g Pd(dppf)Cl$_2$ (3 mmol, 0.1 eq) in one portion at rt under argon atmosphere. After heating for 90 min at 140° C. in a microwave oven, the organic phase was removed in vaccuo and the remaining aqueous extracted with ethyl acetate. The organic phase was filtered and the solvent was evaporated. Purification by flash chromatography (methanol/DCM) yielded 6.9 g (56.7%)N-cyclopropyl-4-(8-methanesulfanyl-6-pyridin-4-yl-imidazo[1,2-a]pyrazin-3-yl)-benzamide: $^1$H-NMR (300 MHz, d$_6$-DMSO): δ=8.84 (1H, s), 8.64 (2H, d), 8.57 (1H, d), 8.08 (2H, d), 8.00 (2H, d), 7.98 (1H, s), 7.86 (2H, d), 2.87 (1H, m), 2.72 (3H, s), 0.69 (2H, m), 0.57 (2H, m) ppm.

Intermediate Example 9-1

Preparation of N-cyclopropyl-4-(8-methylsulfonyl-6-phenyl-imidazo[1,2-a]pyrazin-3-yl)-benzamide

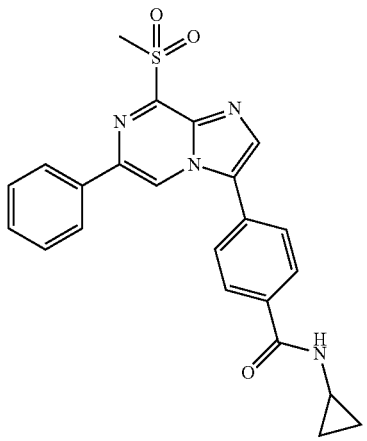 [SMILES: CS(=O)(=O)c1nc(-c2ccccc2)cn2c(-c3ccc(C(=O)NC4CC4)cc3)cnc12]

To a stirred suspension of N-cyclopropyl-4-(8-methylsulfanyl-6-phenyl-imidazo[1,2-a]pyrazin-3-yl)-benzamide (2.95 g, 5.89 mmol) in DCM (60 mL) was added 3-chloroperbenzoic acid (3.91 g, 14.73 mmol, 2.5 eq) in several portions at rt. After stirring for 4 h, the solvent was removed in vaccuo, the residue was taken up in ethyl acetate, washed with sat. NaHCO$_3$ solution, semi-saturated sodium thiosulfate solution and sat. sodium chloride solution. After drying over sodium sulphate and filtration, the product was isolated by careful evaporation and crystallization to yield 1390 mg (93.81%)N-cyclopropyl-4-(8-methylsulfonyl-6-phenyl-imidazo[1,2-a]pyrazin-3-yl)-benzamide: $^1$H-NMR (300 MHz, CDCl$_3$): δ=8.69 (1H, s), 8.07 (1H, s), 7.99 (2H, d), 7.88 (2H, d), 7.66 (2H, d), 7.47 (3H, m), 6.43 (1H, bs), 3.63 (3H, s), 2.96 (1H, m), 0.93 (2H, m), 0.69 (2H, m) ppm. UPLC-MS: RT=1.07 min; m/z 433.5 [MH$^+$]; required MW=432.5.

Intermediate Example 9-2

Preparation of N-cyclopropyl-4-(8-methanesulfonyl-6-pyridin-4-yl-imidazo[1,2-a]pyrazin-3-yl)-benzamide

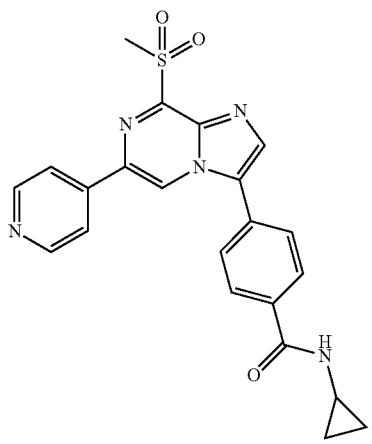 [SMILES: CS(=O)(=O)c1nc(-c2ccncc2)cn2c(-c3ccc(C(=O)NC4CC4)cc3)cnc12]

N-cyclopropyl-4-(8-methanesulfonyl-6-pyridin-4-yl-imidazo[1,2-a]pyrazin-3-yl)-benzamide was prepared analogously to example 9.1 using N-cyclopropyl-4-(8-methanesulfanyl-6-pyridin-4-yl-imidazo[1,2-a]pyrazin-3-yl)-benzamide to yield 74 mg (57.4%)N-cyclopropyl-4-(8-methanesulfonyl-6-pyridin-4-yl-imidazo[1,2-a]pyrazin-3-yl)-benzamide: UPLC-MS: RT=0.66 min; m/z 434.5 [MH$^+$]; required MW=433.5.

Intermediate Example 10-1

Preparation of 6,8-dibromo-3-iodo-imidazo[1,2-a]pyrazine

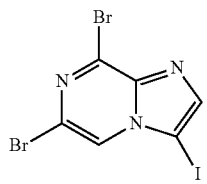 [SMILES: Brc1cn2c(I)cnc2c(Br)n1]

To a stirred solution of intermediate example 1-1 (8.7 g g, 31.4 mmol) in DMF (210 mL) was added NIS (7.42 g, 33 mmol, 1.05 eq) in one portion at rt. After 18 h stirring at 60° C., the solvent was removed in vaccuo and the residue was taken up in DCM and washed with water and saturated sodium thiosulfate solution. The organic phase was dried over sodium sulphate, filtered and the solvent was evaporated to yield 9.46 g (74.8%) 6,8-Dibromo-3-iodo-imidazo[1,2-a]pyrazine: $^1$H-NMR (300 MHz, CDCl$_3$): δ=8.22 (1H, s), 7.91 (1H, s) ppm.

Intermediate Example 10-2

Preparation of (6,8-dibromo-3-iodoimidazo[1,2-a]pyrazin-2-yl)methanol

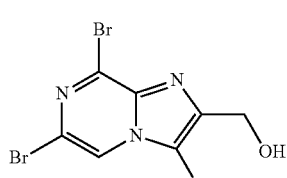

(6,8-dibromo-3-iodoimidazo[1,2-a]pyrazin-2-yl)methanol was prepared analogously to 6,8-dibromo-3-iodo-imidazo[1,2-a]pyrazine to yield 5.53 g (70.66%) of (6,8-dibromo-3-iodoimidazo[1,2-a]pyrazin-2-yl)methanol: $^1$H-NMR (300 MHz, d$_6$-DMSO): δ =8.57 (1H, s), 5.41 (1H, t), 4.55 (2H, d) ppm. UPLC-MS: RT=0.91 min; m/z 433.9 [MH$^+$]; required MW=432.9.

Intermediate Example 11-1

Preparation of N-cyclopropyl-4-[6,8-dibromo-2-(hydroxymethyl)imidazo[1,2-a]pyrazin-3-yl]benzamide

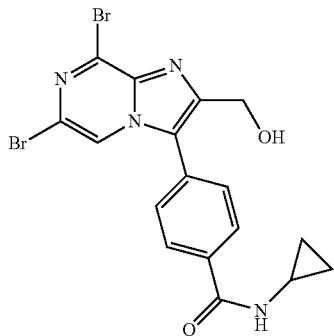 [SMILES: O=C(NC1CC1)c1ccc(-c2c(CO)nc3c(Br)nc(Br)cn23)cc1]

A mixture comprising 5.53 g (12.78 mmol) (6,8-dibromo-3-iodoimidazo[1,2-a]pyrazin-2-yl)methanol which was prepared according to intermediate example 15-2, 3.78 g 4-(cyclopropylaminocarbonyl)phenylboronic acid, 0.93 g (1,1,-bis (diphenylphosphino)ferrocene)-dichloropalladium (II), 19 mL aqueous 2M tribasic potassium phosphate solution and 55 mL tetrahydrofuran was subjected to microwave radiation for 30 minutes at 100° C. Water was added and the mixture was extracted with ethyl acetate. The organic layer was washed with brine and dried over sodium sulfate. After filtration and removal of the solvent the residue was purified by chromatography to give 1.83 g (31%) of the title compound. $^1$H-NMR (300 MHz, d$_6$-DMSO): δ=8.56 (1H, d), 8.53 (1H, s), 7.98 (2H, d), 7.74 (2H, d), 5.48 (1H, t), 4.53 (2H, d), 2.85 (1H, m), 0.69 (2H, m), 0.56 (2H, m) ppm. UPLC-MS: RT=0.94 min; m/z 467.1 [MH$^+$]; required MW=466.1

The following intermediates were prepared analogously using the appropriate boronic acid building block and appropriate di-bromo-iodo precursor:

| Intermediate Example | Structure | Name | Supporting Data |
|---|---|---|---|
| 11-2 | 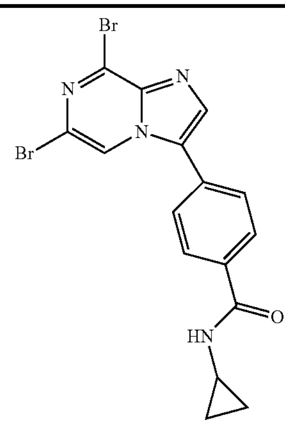 | N-cyclopropyl-4-(6,8-dibromo-imidazo[1,2-a]pyrazin-3-yl)-benzamide | $^1$H-NMR (300 MHz, CDCl$_3$): □ = 8.34 (1H, s), 7.98-7.93 (3H, m), 7.61 (2H, d), 6.34 (1H, bs), 2.95 (1H, m), 0.92 (2H, m), 0.66 (2H, m) ppm. RT = 1.02 MW$_{found}$ = 437.1 MW$_{calc}$ = 436.1 |
| 11-3 | 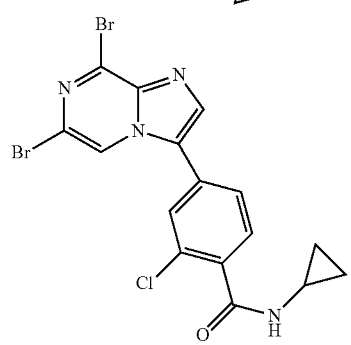 | 2-chloro-N-cyclopropyl-4-(6,8-dibromoimidazo[1,2-a]pyrazin-3-yl)benzamide | Yield: 1.39 g (40%) |
| 11-4 | 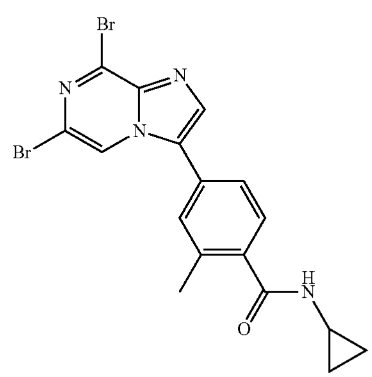 [SMILES: Cc1cc(-c2cnc3c(Br)nc(Br)cn23)ccc1C(=O)NC1CC1] | N-cyclopropyl-4-(6,8-dibromoimidazo[1,2-a]pyrazin-3-yl)-2-methylbenzamide | Yield: 968 mg (48%) |

Intermediate Example 12

Preparation of N-cyclopropyl-2-methyl-4-(4,4,5,5-tetramethyl-1,3,2-dioxaborolan-2-yl)benzamide

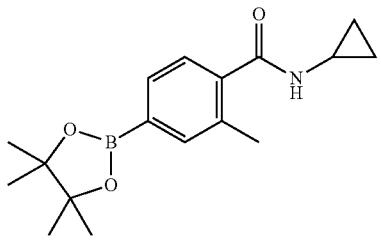

Step A: Preparation of 4-bromo-N-cyclopropyl-2-methylbenzamide

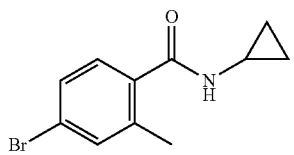

To a stirred solution of 4-bromo-2-methylbenzoic acid (300 g, 1.4 mol) in DCM (8.4 L) at rt was added cyclopropanamine (79.64 g, 1.4 mol) and EDC (320.9 g, 1.67 mol) in one portion. After stirring overnight, the solution was washed with water and the aqueous phase was reextracted with DCM. The combined organic phases were dried over $Na_2SO_4$, filtered and evaporated. The remaining solid was triturated with diisopropyl ether, filtered, washed and dried in vaccuo to yield 260 g (73.4%) 4-bromo-N-cyclopropyl-2-methylbenzamide: $^1$H-NMR (300 MHz, $CDCl_3$): δ =7.34 (s, 1H), 7.27 (d, 1H), 7.14 (d, 1H), 5.96 (bs, 1H), 2.85 (m, 1H), 2.38 (s, 3H), 0.85 (m, 2H), 0.59 (m, 2H) ppm.

Step B: Preparation of N-cyclopropyl-2-methyl-4-(4,4,5,5-tetramethyl-1,3,2-dioxaborolan-2-yl)benzamide

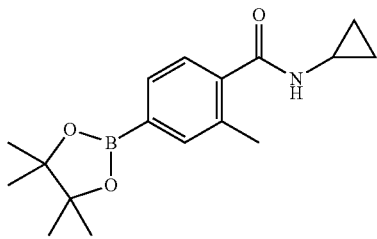 [SMILES: Cc1cc(B2OC(C)(C)C(C)(C)O2)ccc1C(=O)NC1CC1]

To a solution of 4-bromo-N-cyclopropyl-2-methylbenzamide (260 g, 1.02 mol) in dioxane (2 L) at rt was added bis-(pinacolato)-diboron (390 g, 1.53 mol), 2-dicyclohexylphosphino-2',4',6'-triisopropylbiphenyl (19.5 g, 40.9 mmol), potassium acetate (150.6 g, 1.53 mol) and tris-(dibenzylidenaceton)-dipalladium(0) (9.37 g, 10.2 mmol) and the mixture was refluxed for 6 h, After cooling to rt, water (3 L) and ethyl acetate (5 L) was added and the mixture stirred for 15 min. The organic phase was washed with water, dried over $Na_2(SO_4)$, filtered and evaporated. Flash chromatography (ethyl acetate/hexane) yielded 308 g (56.3%)N-cyclopropyl-2-methyl-4-(4,4,5,5-tetramethyl-1,3,2-dioxaborolan-2-yl)benzamide: $^1$H-NMR (300 MHz, $CDCl_3$): δ=7.63 (s, 1H), 7.60 (d, 1H), 7.28 (d, 1H), 5.94 (bs, 1H), 2.87 (m, 1H), 2.41 (s, 3H), 1.33 (s, 6H), 0.85 (m, 2H), 0.59 (m, 2H) ppm.

Example 1-1

Preparation of N-cyclopropyl-4-{8-[(2-methylpropyl)amino]-6-[(1E)-prop-1-en-1-yl]imidazo[1,2-a]pyrazin-3-yl}benzamide

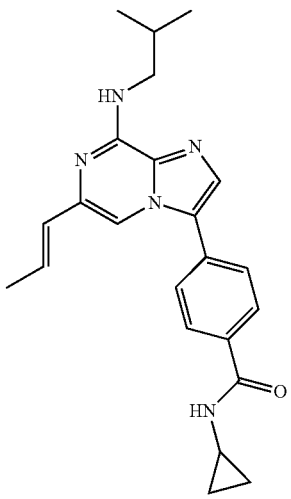 [SMILES: C/C=C/c1cn2c(-c3ccc(C(=O)NC4CC4)cc3)cnc2c(NCC(C)C)n1]

0.4 mmol intermediate example 6-1 (171 mg) in 2 mL NMP were combined with 0.8 mmol (1E)-prop-1-en-1-ylboronic acid (69 mg), 0.04 mmol Pd(dppf)$Cl_2$ (32 mg) and 1.2 mmol $K_2CO_3$ (1.2 mL, 1M in water, 3 eq) in a sealed vial and heated at 140° C. under microwave irradiation for 40 min. After cooling, the solution was filtered and subjected to preparative HPLC to give 26.7 mg (16.7%)N-cyclopropyl-4-{8-[(2-methylpropyl)amino]-6-[(1E)-prop-1-en-1-yl]imidazo[1,2-a]pyrazin-3-yl}benzamide: $^1$H-NMR (300 MHz, $CDCl_3$): δ=7.88 (2H, d), 7.60 (2H, d), 7.54 (1H, s), 7.36 (1H, s), 6.76 (1H, m), 6.27 (1H, bs), 6.21 (1H, d), 6.02 (1H, t), 3.50 (2H, dd), 2.95 (1H, m), 2.05 (1H, m), 1.91 (3H, d), 1004 (6H, d), 0.92 (2H, m), 0.66 (2H, m) ppm; UPLC-MS: RT=1.35 min; m/z (ES+) 390.5 [MH$^+$]; required MW=389.5.

The following compound examples were prepared analogously to the procedure described above using the appropriate intermediate example 6 and the appropriate boronic acid building block [LC-MS data such as retention time (RT in min) or observed mass peak were collected using LC-MS Method A unless explicitly stated]:

| Example | Structure | Name | Analytical Data |
|---|---|---|---|
| 1-2 | 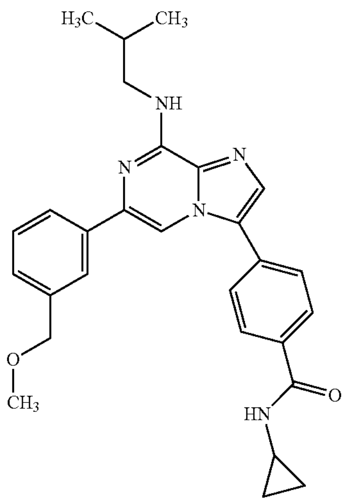 [SMILES: COCc1cccc(-c2cn3c(-c4ccc(C(=O)NC5CC5)cc4)cnc3c(NCC(C)C)n2)c1] | N-cyclopropyl-4-{6-[3-(methoxymethyl)phenyl]-8-[(2-methylpropyl)amino]imidazo[1,2-a]pyrazin-3-yl}benzamide | RT = 1.38<br>$MW_{found}$ = 470.6<br>$MW_{calc}$ = 469.6 |
| 1-3 | 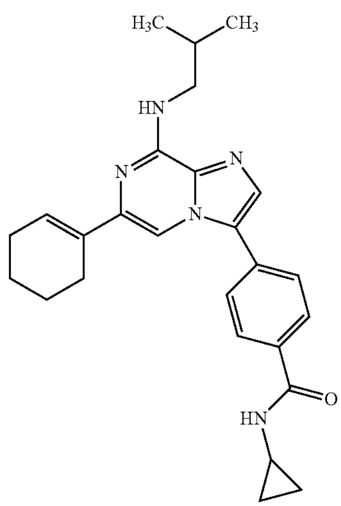 [SMILES: CC(C)CNc1nc(C2=CCCCC2)cn2c(-c3ccc(C(=O)NC4CC4)cc3)cnc12] | 4-{6-(cyclohex-1-en-1-yl)-8-[(2-methylpropyl)amino]imidazo[1,2-a]pyrazin-3-yl}-N-cyclopropylbenzamide | RT = 1.49<br>$MW_{found}$ = 430.6<br>$MW_{calc}$ = 429.6 |
| 1-4 | 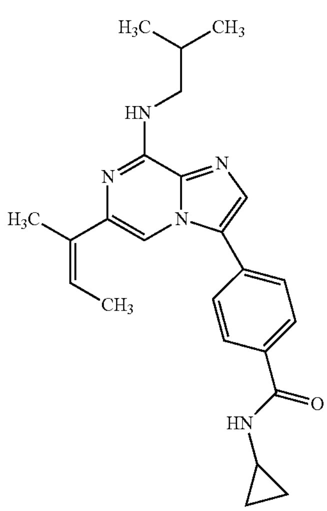 [SMILES: C/C=C(/C)c1cn2c(-c3ccc(C(=O)NC4CC4)cc3)cnc2c(NCC(C)C)n1] | 4-{6-[(2Z)-but-2-en-2-yl]-8-[(2-methylpropyl)amino]imidazo[1,2-a]pyrazin-3-yl}-N-cyclopropylbenzamide | RT = 1.27<br>$MW_{found}$ = 404.5<br>$MW_{calc}$ = 403.5 |

-continued

| Example | Structure | Name | Analytical Data |
|---|---|---|---|
| 1-5 | 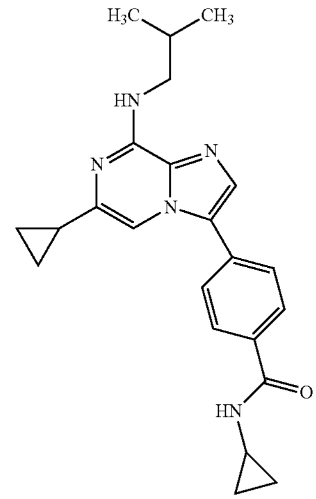 [SMILES: CC(C)CNc1nc(C2CC2)cn2c(-c3ccc(C(=O)NC4CC4)cc3)cnc12] | N-cyclopropyl-4-{6-cyclopropyl-8-[(2-methylpropyl)amino]imidazo[1,2-a]pyrazin-3-yl}benzamide | RT = 1.26<br>$MW_{found}$ = 390.5<br>$MW_{calc}$ = 389.5 |
| 1-6 | 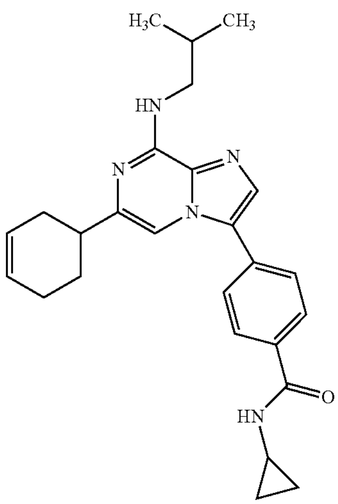 [SMILES: CC(C)CNc1nc(C2CC=CCC2)cn2c(-c3ccc(C(=O)NC4CC4)cc3)cnc12] | 4-{6-(cyclohex-3-en-1-yl)-8-[(2-methylpropyl)amino]imidazo[1,2-a]pyrazin-3-yl}-N-cyclopropylbenzamide[1] | RT = 1.36<br>$MW_{found}$ = 430.6<br>$MW_{calc}$ = 429.6 |
| 1-7 | 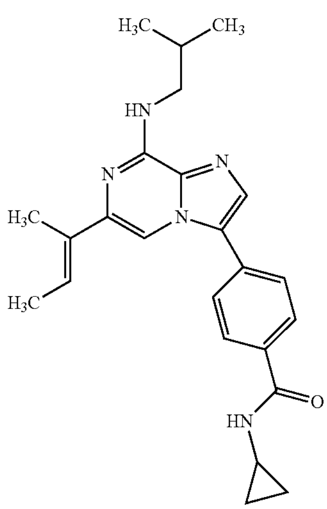 [SMILES: C/C=C(\C)c1cn2c(-c3ccc(C(=O)NC4CC4)cc3)cnc2c(NCC(C)C)n1] | 4-{6-[(2E)-but-2-en-2-yl]-8-[(2-methylpropyl)amino]imidazo[1,2-a]pyrazin-3-yl}-N-cyclopropylbenzamide | RT = 1.32<br>$MW_{found}$ = 404.5<br>$MW_{calc}$ = 403.5 |

-continued

| Example | Structure | Name | Analytical Data |
|---|---|---|---|
| 1-8 | 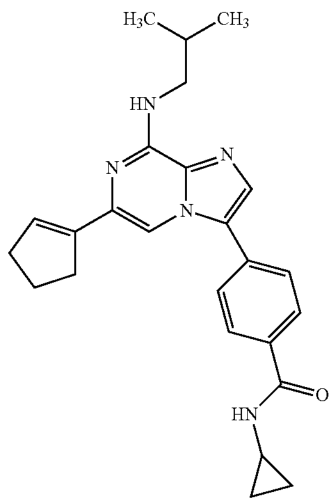 [SMILES: CC(C)CNc1nc(C2=CCCC2)cn2c(-c3ccc(C(=O)NC4CC4)cc3)cnc12] | 4-{6-(cyclopent-1-en-1-yl)-8-[(2-methylpropyl)amino]imidazo[1,2-a]pyrazin-3-yl}-N-cyclopropylbenzamide | RT = 1.48<br>$MW_{found}$ = 416.5<br>$MW_{calc}$ = 415.5 |
| 1-9 | 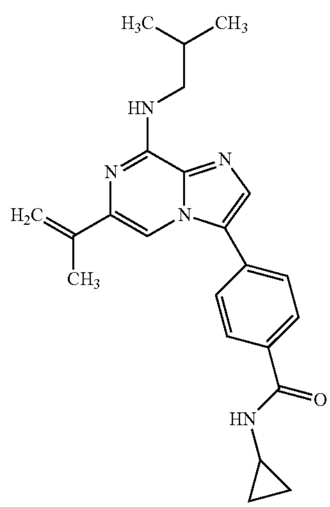 [SMILES: C=C(C)c1cn2c(-c3ccc(C(=O)NC4CC4)cc3)cnc2c(NCC(C)C)n1] | N-cyclopropyl-4-{8-[(2-methylpropyl)amino]-6-(prop-1-en-2-yl)imidazo[1,2-a]pyrazin-3-yl}benzamide | RT = 1.39<br>$MW_{found}$ = 390.5<br>$MW_{calc}$ = 389.5 |
| 1-10 | 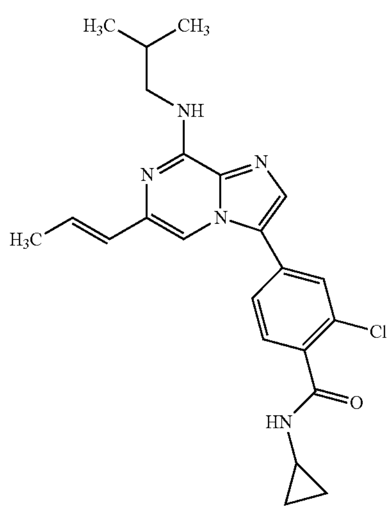 [SMILES: C/C=C/c1cn2c(-c3ccc(C(=O)NC4CC4)c(Cl)c3)cnc2c(NCC(C)C)n1] | 2-chloro-N-cyclopropyl-4-{8-[(2-methylpropyl)amino]-6-[(1E)-prop-1-en-1-yl]imidazo[1,2-a]pyrazin-3-yl}benzamide | RT = 1.35<br>$MW_{found}$ = 424.9<br>$MW_{calc}$ = 423.9 |

-continued

| Example | Structure | Name | Analytical Data |
|---|---|---|---|
| 1-11 | 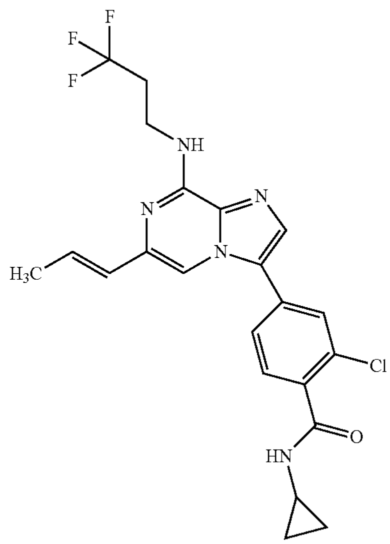 [SMILES: C/C=C/c1cn2c(-c3ccc(C(=O)NC4CC4)c(Cl)c3)cnc2c(NCCC(F)(F)F)n1] | 2-chloro-N-cyclopropyl-4-{6-[(1E)-prop-1-en-1-yl]-8-[(3,3,3-trifluoropropyl)amino]imidazo[1,2-a]pyrazin-3-yl}benzamide | RT = 1.32<br>$MW_{found}$ = 464.9<br>$MW_{calc}$ = 463.9 |
| 1-12 | 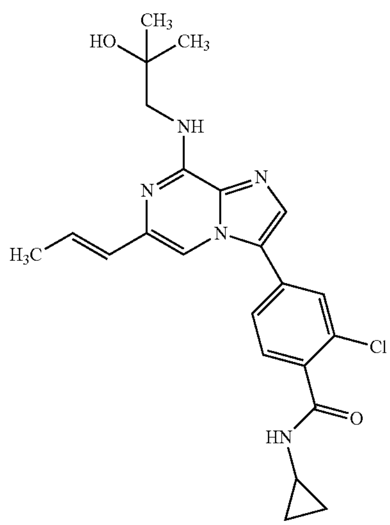 [SMILES: C/C=C/c1cn2c(-c3ccc(C(=O)NC4CC4)c(Cl)c3)cnc2c(NCC(C)(C)O)n1] | 2-chloro-N-cyclopropyl-4-{8-[(2-hydroxy-2-methylpropyl)amino]-6-[(1E)-prop-1-en-1-yl]imidazo[1,2-a]pyrazin-3-yl}benzamide | RT = 1.02<br>$MW_{found}$ = 440.9<br>$MW_{calc}$ = 439.9 |
| 1-13 | 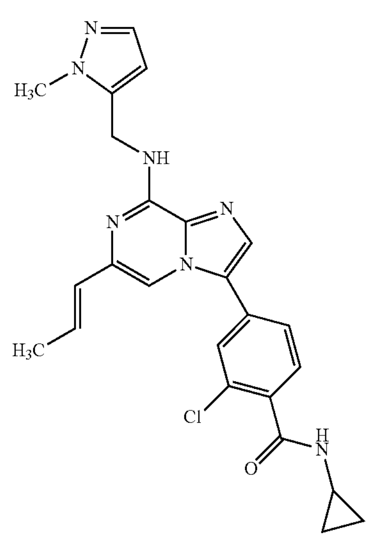 [SMILES: C/C=C/c1cn2c(-c3ccc(C(=O)NC4CC4)c(Cl)c3)cnc2c(NCc2ccnn2C)n1] | 2-chloro-N-cyclopropyl-4-(8-{[(1-methyl-1H-pyrazol-5-yl)methyl]amino}-6-[(1E)-prop-1-en-1-yl]imidazo[1,2-a]pyrazin-3-yl)benzamide | RT = 1.08<br>$MW_{found}$ = 462.9<br>$MW_{calc}$ = 461.9 |

-continued

| Example | Structure | Name | Analytical Data |
|---|---|---|---|
| 1-14 | 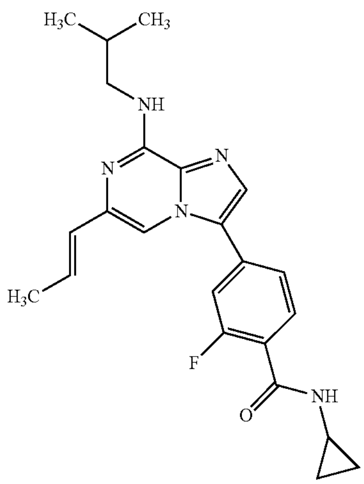 [SMILES: C/C=C/c1cn2c(-c3ccc(C(=O)NC4CC4)c(F)c3)cnc2c(NCC(C)C)n1] | N-cyclopropyl-2-fluoro-4-{8-[(2-methylpropyl)amino]-6-[(1E)-prop-1-en-1-yl]imidazo[1,2-a]pyrazin-3-yl}benzamide | RT = 1.37<br>MW$_{found}$ = 408.5<br>MW$_{calc}$ = 407.5 |
| 1-15 | 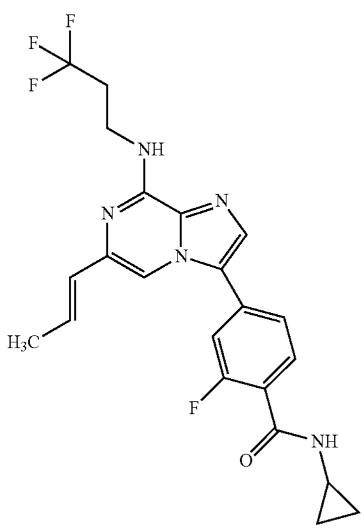 [SMILES: C/C=C/c1cn2c(-c3ccc(C(=O)NC4CC4)c(F)c3)cnc2c(NCCC(F)(F)F)n1] | N-cyclopropyl-2-fluoro-4-{6-[(1E)-prop-1-en-1-yl]-8-[(3,3,3-trifluoropropyl)amino]imidazo[1,2-a]pyrazin-3-yl}benzamide | RT = 1.32<br>MW$_{found}$ = 448.4<br>MW$_{calc}$ = 447.4 |
| 1-16 | 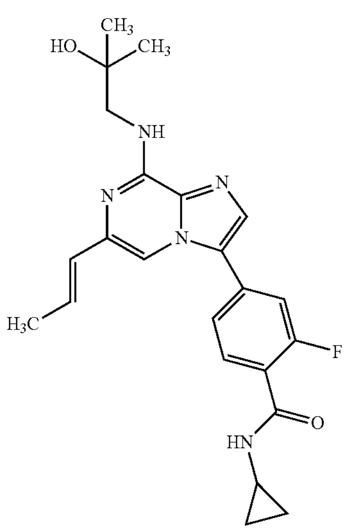 [SMILES: C/C=C/c1cn2c(-c3ccc(C(=O)NC4CC4)c(F)c3)cnc2c(NCC(C)(C)O)n1] | N-cyclopropyl-2-fluoro-4-{8-[(2-hydroxy-2-methylpropyl)amino]-6-[(1E)-prop-1-en-1-yl]imidazo[1,2-a]pyrazin-3-yl}benzamide | RT = 1.03<br>MW$_{found}$ = 424.5<br>MW$_{calc}$ = 423.5 |

-continued

| Example | Structure | Name | Analytical Data |
|---------|-----------|------|-----------------|
| 1-17 | 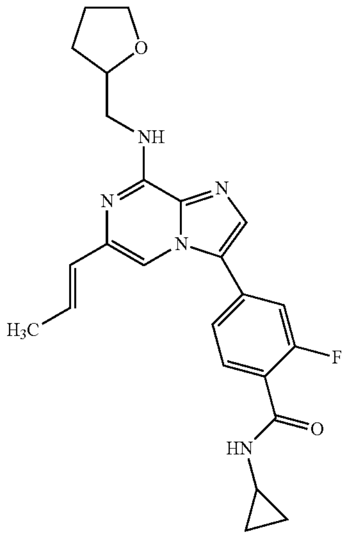 [SMILES: C/C=C/c1cn2c(-c3ccc(C(=O)NC4CC4)c(F)c3)cnc2c(NCC2CCCO2)n1] | N-cyclopropyl-2-fluoro-4-{6-[(1E)-prop-1-en-1-yl]-8-[(tetrahydrofuran-2-ylmethyl)amino]imidazo[1,2-a]pyrazin-3-yl}benzamide | RT = 1.15<br>$MW_{found}$ = 436.5<br>$MW_{calc}$ = 435.5 |
| 1-18 | 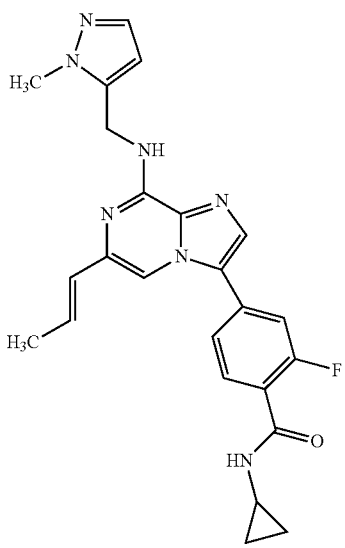 [SMILES: C/C=C/c1cn2c(-c3ccc(C(=O)NC4CC4)c(F)c3)cnc2c(NCc2ccnn2C)n1] | N-cyclopropyl-2-fluoro-4-(8-{[(1-methyl-1H-pyrazol-5-yl)methyl]amino}-6-[(1E)-prop-1-en-1-yl]imidazo[1,2-a]pyrazin-3-yl)benzamide | RT = 1.09<br>$MW_{found}$ = 446.5<br>$MW_{calc}$ = 445.5 |
| 1-19 | 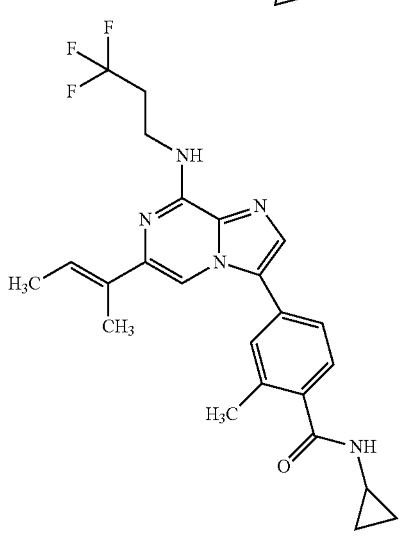 | 4-{6-[(2E)-but-2-en-2-yl]-8-[(3,3,3-trifluoropropyl)amino]imidazo[1,2-a]pyrazin-3-yl}-N-cyclopropyl-2-methylbenzamide | RT = 1.32<br>$MW_{found}$ = 458.5<br>$MW_{calc}$ = 457.5 |

[1]) Byproduct from 4-{6-(cyclohex-1-en-1-yl)-8-[(2-methylpropyl)amino]imidazo[1,2-a]pyrazin-3-yl}-N-cyclopropylbenzamide

Example 1-20

Preparation of N-cyclopropyl-4-{6-(4-ethenylphenyl)-8-[(2-methylpropyl)amino]imidazo[1,2-a]pyrazin-3-yl}benzamide

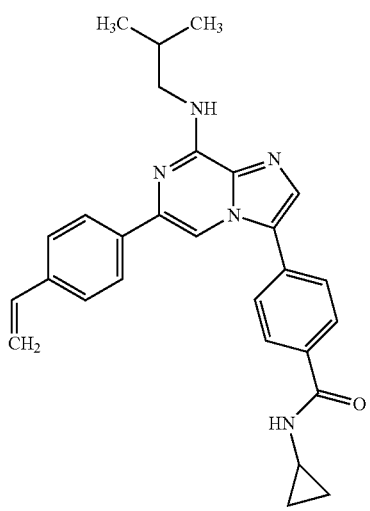 [SMILES: C=Cc1ccc(-c2cn3c(-c4ccc(C(=O)NC5CC5)cc4)cnc3c(NCC(C)C)n2)cc1]

A mixture of 0.5 g (1.17 mmol) 4-{6-bromo-8-[(2-methylpropyl)amino]imidazo[1,2-a]pyrazin-3-yl}-N-cyclopropylbenzamide (intermediate example 6-1), 345 mg (4-ethenylphenyl)boronic acid, 17 mL n-propanol, 1.75 mL of an aqueous 2M potassium carbonate solution, 15 mg triphenylphosphine, and 82 mg bis(triphenylphosphine)palladium was stirred at 120° C. for 2 hours. The solution was cooled, water added and extracted with dichloromethane. The organic phase was dried over sodium sulfate. After filtration and removal of solvent the residue was subjected to a column chromatography on silica gel to give 509 mg (97%) of the title compound. $^1$H-NMR (CDCl$_3$): δ=0.67 (2H), 0.92 (2H), 1.06 (3H), 1.08 (3H), 2.09 (1H), 2.95 (1H), 3.58 (2H), 5.28 (1H), 5.80 (1H), 6.13 (1H), 6.34 (1H), 6.75 (1H), 7.47 (2H), 7.59 (1H), 7.65 (2H), 7.87 (2H), 7.92 (2H), 7.95 (1H) ppm.

Example 2-1

Preparation of tert-butyl [3-({3-[4-(cyclopropylcarbamoyl)phenyl]-6-(pyridin-4-yl)imidazo[1,2-a]pyrazin-8-yl}amino)propyl]carbamate

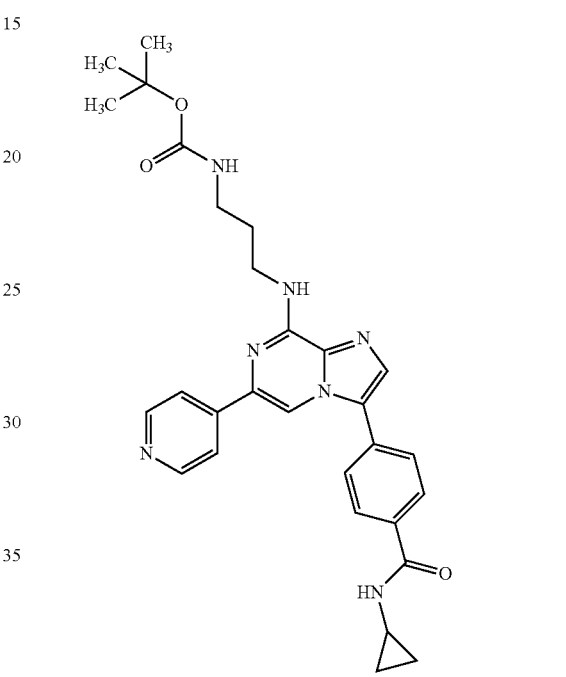

0.1 mmol N-cyclopropyl-4-[8-(methylsulfonyl)-6-(pyridin-4-yl)imidazo[1,2-a]pyrazin-3-yl]benzamide (intermediate example 9-2) (1 mL, 0.1 M in NMP), 0.2 mmol tert-butyl (3-aminopropyl)carbamate (0.4 mL, 0.5 M in NMP, 2 eq) and 0.3 mmol DIPEA (41 µL, 3 eq) were combined in a sealed vial and heated at 170° C. under microwave irradiation for 60 min. After cooling, the solution was filtered and subjected to preparative HPLC to give 8.9 mg tert-butyl [3-({3-[4-(cyclopropylcarbamoyl)phenyl]-6-(pyridin-4-yl)imidazo[1,2-a]pyrazin-8-yl}amino)propyl]carbamate (11%): $^1$H-NMR (300 MHz, d$_6$-DMSO): δ=8.58 (2H, d), 8.54 (1H, d), 8.32 (1H, s), 8.02-7.93 (3H, m), 7.87-7.76 (4H, m), 6.83 (1H, tr), 3.58 (2H, m), 3.01 (2H, m), 2.86 (1H, m), 1.77 (2H, m), 1.32 (9H, s), 0.68 (2H, m), 0.55 (2H, m) ppm; UPLC-MS: RT=0.90 min; m/z (ES+) 528.6 [MH$^+$]; required MW=527.6.

Example 2-2

Preparation of tert-Butyl [5-({3-[4-(cyclopropylcarbamoyl)phenyl]-6-phenylimidazo[1,2-a]pyrazin-8-yl}amino)pent-2-yn-1-yl]carbamate

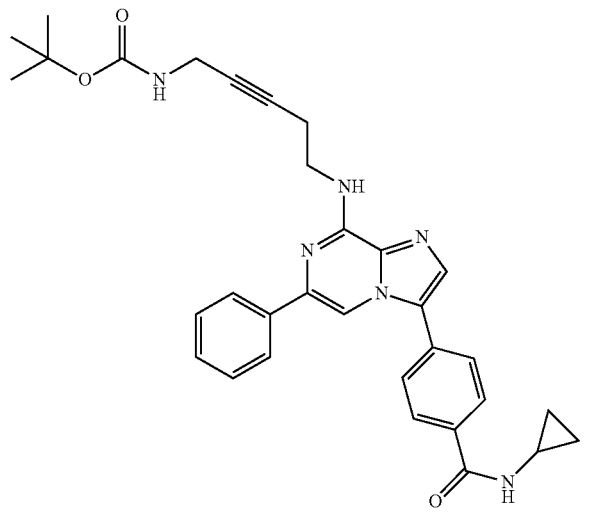 [SMILES: CC(C)(C)OC(=O)NCC#CCCNc1nc(-c2ccccc2)cn2c(-c3ccc(C(=O)NC4CC4)cc3)cnc12]

To a solution of 75 mg (173 μmol) N-cyclopropyl-4-[8-(methylsulfonyl)-6-phenylimidazo[1,2-a]pyrazin-3-yl]benzamide which was prepared according to intermediate example 9-1 in 0.3 mL N,N-dimethylformamide were added 60 μL tert-butyl (5-aminopent-2-yn-1-yl)carbamate and the mixture was stirred at 50° C. overnight. Toluene was added and the mixture was evaporated. The residue was purified by chromatography to give 23.6 mg (25%) of the title compound $^1$H-NMR (CDCl$_3$): δ=0.67 (2H), 0.92 (2H), 1.45 (9H), 2.67 (2H), 2.95 (1H), 3.87 (2H), 3.93 (2H), 4.82 (1H), 6.32 (2H), 7.32-7.49 (3H), 7.62 (1H), 7.65 (2H), 7.88 (2H), 7.92 (2H), 7.98 (1H) ppm.

Example 2-3

Preparation of tert-Butyl [(2E)-5-({3-[4-(cyclopropylcarbamoyl)phenyl]-6-phenylimidazo[1,2-a]pyrazin-8-yl}amino)pent-2-en-1-yl]carbamate

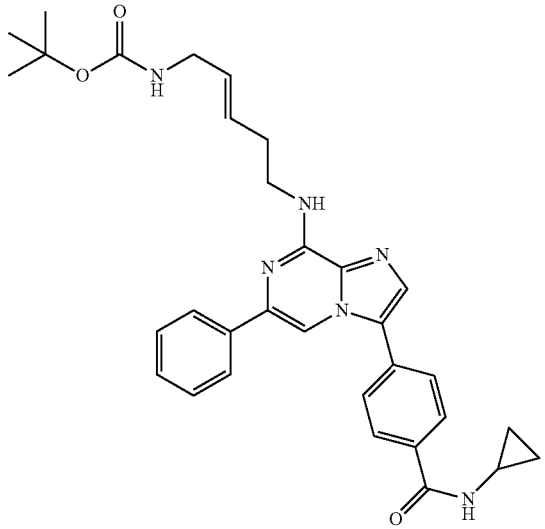 [SMILES: CC(C)(C)OC(=O)NC/C=C/CCNc1nc(-c2ccccc2)cn2c(-c3ccc(C(=O)NC4CC4)cc3)cnc12]

100 mg (231 μmol) N-cyclopropyl-4-[8-(methylsulfonyl)-6-phenylimidazo[1,2-a]pyrazin-3-yl]benzamide which was prepared according to intermediate example 9-1 were transformed in analogy to example 2-1 using tert-butyl [(2E)-5-aminopent-2-en-1-yl]carbamate to give after working up and purification 28.5 mg (21%) of the title compound.

$^1$H-NMR (CDCl$_3$): δ=0.67 (2H), 0.92 (2H), 1.44 (9H), 2.51 (2H), 2.95 (1H), 3.74 (2H), 3.79 (2H), 4.67 (1H), 5.62 (1H), 5.71 (1H), 6.09 (1H), 6.34 (1H), 7.36 (1H), 7.44 (2H), 7.60 (1H), 7.65 (2H), 7.90 (2H), 7.92 (2H), 7.96 (1H) ppm.

Example 2-4

Preparation of tert-Butyl [(2Z)-5-({3-[4-(cyclopropylcarbamoyl)phenyl]-6-phenylimidazo[1,2-a]pyrazin-8-yl}amino)pent-2-en-1-yl]carbamate

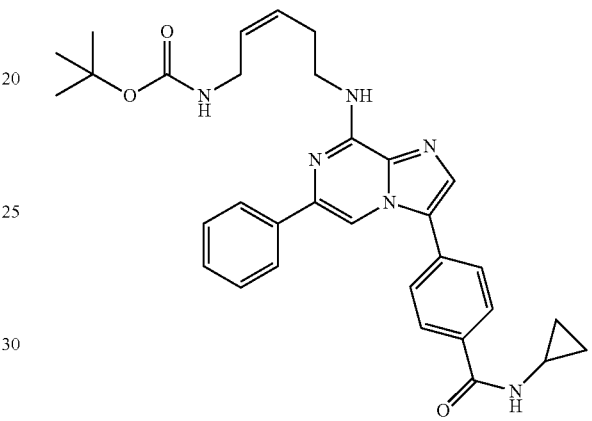

100 mg (231 μmol) N-cyclopropyl-4-[8-(methylsulfonyl)-6-phenylimidazo[1,2-a]pyrazin-3-yl]benzamide which was prepared according to intermediate example 9-1 were transformed in analogy to example 2-1 using tert-butyl [(2Z)-5-aminopent-2-en-1-yl]carbamate to give after working up and purification 37.7 mg (28%) of the title compound.

$^1$H-NMR (CDCl$_3$): δ=0.67 (2H), 0.92 (2H), 1.45 (9H), 2.56 (2H), 2.95 (1H), 3.75-3.86 (4H), 5.21 (1H), 5.60-5.70 (2H), 6.10 (1H), 6.33 (1H), 7.36 (1H), 7.44 (2H), 7.60 (1H), 7.65 (2H), 7.89 (2H), 7.92 (2H), 7.96 (1H) ppm.

Example 3-1

Preparation of (RS) N-cyclopropyl-4-{6-[4-(cyclopropylsulfinyl)phenyl]-8-(isobutylamino)imidazo[1,2-a]pyrazin-3-yl}benzamide

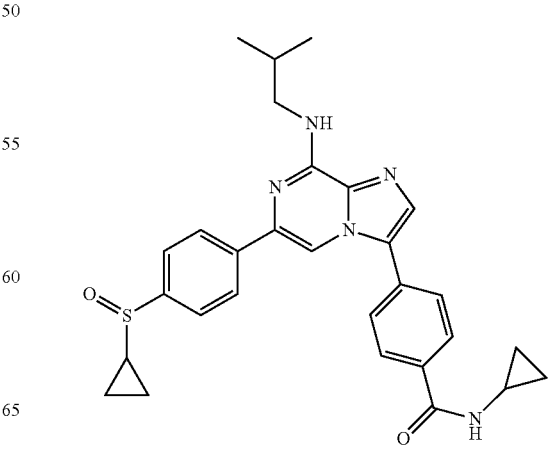

Step A: Preparation of N-cyclopropyl-4-{6-[4-(cyclopropylsulfanyl)phenyl]-8-[(2-methylpropyl)amino]imidazo[1,2-a]pyrazin-3-yl}benzamide

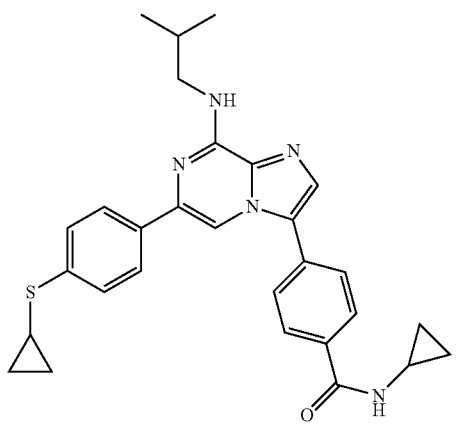 [SMILES: CC(C)CNc1nc(-c2ccc(SC3CC3)cc2)cn2c(-c3ccc(C(=O)NC4CC4)cc3)cnc12]

500 mg (1.17 mmol) 4-{6-bromo-8-[(2-methylpropyl)amino]imidazo[1,2-a]pyrazin-3-yl}-N-cyclopropylbenzamide which was prepared according to intermediate example 6-1 were transformed in analogy to example 1 using [4-(cyclopropylsulfanyl)phenyl]boronic acid to give after working up and purification 512 mg (88%) of the title compound.

Step B: Preparation of (RS) N-cyclopropyl-4-{6-[4-(cyclopropylsulfinyl)phenyl]-8-(isobutylamino)imidazo[1,2-a]pyrazin-3-yl}benzamide

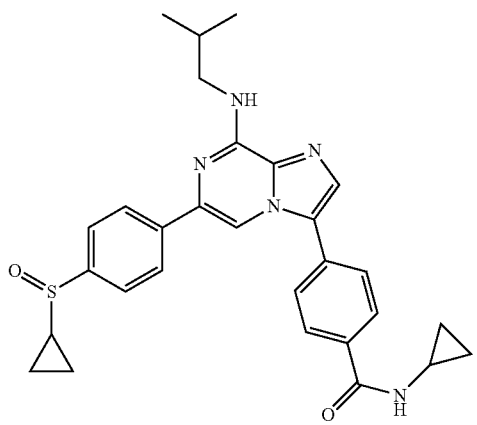 [SMILES: CC(C)CNc1nc(-c2ccc(S(=O)C3CC3)cc2)cn2c(-c3ccc(C(=O)NC4CC4)cc3)cnc12]

A solution of 50 mg (100 μmol) N-cyclopropyl-4-{6-[4-(cyclopropylsulfanyl)phenyl]-8-(isobutylamino)imidazo[1,2-a]pyrazin-3-yl}benzamide in 5.0 mL dichloromethane was cooled to −30° C. and 1.16 mL of a 0.15 molar dioxirane solution in acetone were added. After 15 minutes of stirring the mixture was warmed to 23° C., the solvent removed and the residue was purified by chromatography to give 33.3 mg (59%) of the title compound. $^1$H-NMR (CDCl$_3$): δ=0.67 (2H), 0.86-1.05 (5H), 1.06 (3H), 1.07 (3H), 1.25 (1H), 2.09 (1H), 2.28 (1H), 2.95 (1H), 3.56 (2H), 6.36 (1H), 6.54 (1H), 7.60 (1H), 7.63 (2H), 7.70 (2H), 7.94 (2H), 7.96 (1H), 8.02 (2H) ppm.

Example 4-1

Preparation of 4-{6-cyclohexyl-8-[(2-methylpropyl)amino]imidazo[1,2-a]pyrazin-3-yl}-N-cyclopropyl-benzamide

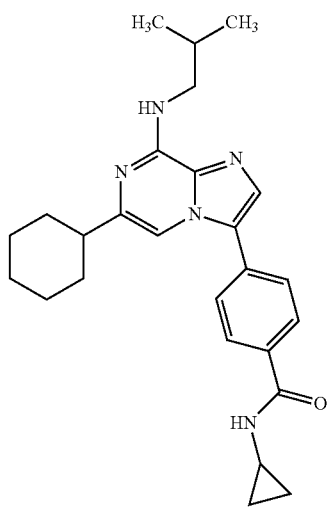 [SMILES: CC(C)CNc1nc(C2CCCCC2)cn2c(-c3ccc(C(=O)NC4CC4)cc3)cnc12]

To a solution of 52 mg (0.12 mmol) 4-{6-(cyclohex-1-en-1-yl)-8-[(2-methylpropyl)amino]imidazo[1,2-a]pyrazin-3-yl}-N-cyclopropylbenzamide (example 1-3) in 8 mL ethanol was added 5 mg 10% Pd/C and the mixture was stirred at rt and normal pressure overnight under hydrogen atmosphere. The mixture was filtered and purified by HPLC to yield 20.8 mg (40%) of the title compound. UPLC-MS: RT=1.39 min; m/z (ES+) 432.6 [MH$^+$]; required MW=431.6. $^1$H-NMR (CDCl$_3$): δ=0.65 (2H), 0.89 (2H), 1.02 (6H), 1.17-1.54 (5H), 1.67-2.07 (6H), 2.42 (1H), 2.94 (1H), 3.47 (2H), 6.06 (1H), 6.39 (1H), 7.34 (1H), 7.53 (1H), 7.59 (2H), 7.89 (2H) ppm.

The following compound examples were prepared analogously to the procedure described above [LC-MS data such as retention time (RT in min) or observed mass peak were collected using LC-MS Method A unless explicitly stated]:

| Example | Structure | Name | Analytical Data |
|---|---|---|---|
| 4-2 | 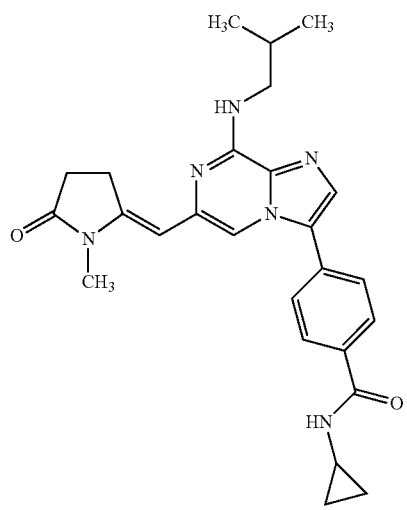 [SMILES: CC(C)CNc1nc(/C=C2\CCC(=O)N2C)cn2c(-c3ccc(C(=O)NC4CC4)cc3)cnc12] | 4-{6-cyclopentyl-8-[(2-methylpropyl)amino]imidazo[1,2-a]pyrazin-3-yl}-N-cyclopropylbenzamide | RT = 1.35<br>$MW_{found}$ = 418.5<br>$MW_{calc}$ = 417.5 |

*) Alkene precursors were synthesized in analogy to procedure example 1-1

Example 5-1

Preparation of N-cyclopropyl-4-{6-[(E)-(1-methyl-5-oxopyrrolidin-2-ylidene)methyl]-8-[(2-methylpropyl)amino]imidazo[1,2-a]pyrazin-3-yl}benzamide Step A: Preparation of N-cyclopropyl-4-{6-[5-(methylamino)-5-oxopent-1-yn-1-yl]-8-[(2-methylpropyl)amino]imidazo[1,2-a]pyrazin-3-yl}benzamide

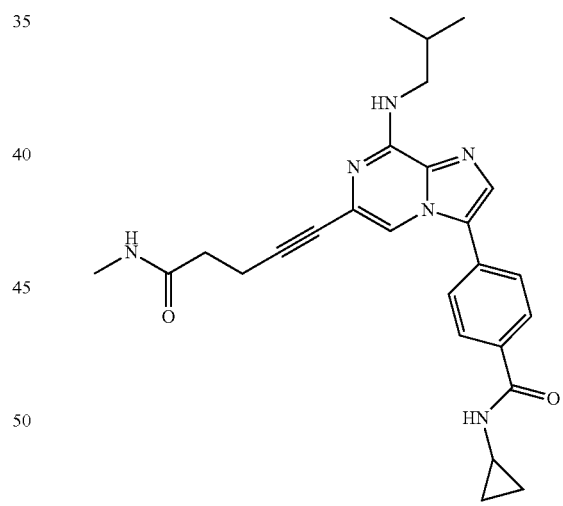

To a solution of 128 mg (0.3 mmol) 4-{6-bromo-8-[(2-methylpropyl)amino]imidazo[1,2-a]pyrazin-3-yl}-N-cyclopropylbenzamide in 1 mL THF were added 133 mg (1.2 mmol) N-methylpent-4-ynamide, 42 mg (0.06 mmol dichloropalladium-triphenylphosphane (1:2) and 363 mg (1.5 mmol) tetrabutylammoniumfluoride and the mixture was heated at 80° C. for 180 min in a microwave tube. The mixture was evaporated, redissolved in 2 mL DMSO, filtered and purified by HPLC to yield 60 mg (44%) of the title compound. UPLC-MS: RT=1.01 min; m/z (ES+) 459.6 [MH$^+$]; required MW=458.6.

Step B: Preparation of N-cyclopropyl-4-{6-[(E)-(1-methyl-5-oxopyrrolidin-2-ylidene)methyl]-8-[(2-methylpropyl)amino]imidazo[1,2-a]pyrazin-3-yl}benzamide

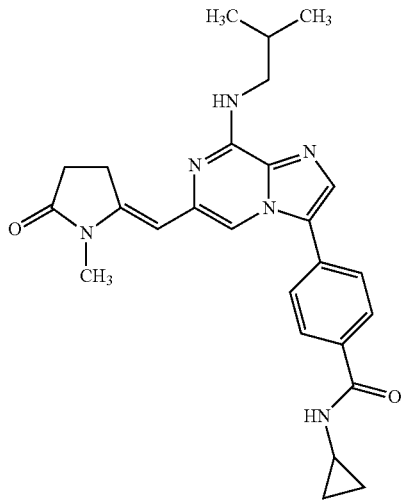 [SMILES: CC(C)CNc1nc(/C=C2\CCC(=O)N2C)cn2c(-c3ccc(C(=O)NC4CC4)cc3)cnc12]

To a solution of 23 mg (0.05 mmol) N-cyclopropyl-4-{6-[5-(methylamino)-5-oxopent-1-yn-1-yl]-8-[(2-methylpropyl)amino]imidazo[1,2-a]pyrazin-3-yl}benzamide in 1.00 mL NMP were added 6.5 mg (0.1 mmol) sodium azide and 0.5 mg (0.003 mmol) copper(I)iodide and the mixture was heated at 160° C. for 30 min in a microwave tube. The mixture was filtered and purified by HPLC to yield 4.3 mg (19%) of the title compound. UPLC-MS: RT=1.08 min; m/z (ES+) 459.6 [MH$^+$]; required MW=458.6. $^1$H-NMR (300 MHz, CDCl$_3$): δ=7.91 (2H, d), 7.59 (4H, m), 7.39 (1H, s), 6.31 (1H, tr), 6.28 (1H, s), 3.45 (1H, m), 3.40 (2H, t), 2.95 (1H, m), 2.82 (3H, s), 2.56 (1H, m), 2.33 (1H, s), 2.05 (1H, m), 1.95 (1H, m), 1.05 (6H, d), 0.92 (2H, m), 0.66 (2H, m) ppm.

Example 6-1

Preparation of N-{3-[4-(cyclopropylcarbamoyl)phenyl]-8-[(2-methylpropyl)amino]imidazo[1,2-a]pyrazin-6-yl}pyridine-2-carboxamide

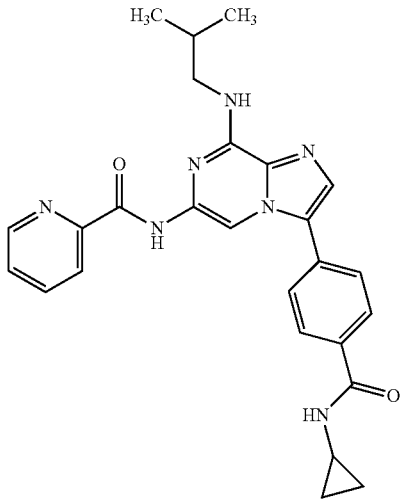 [SMILES: CC(C)CNc1nc(NC(=O)c2ccccn2)cn2c(-c3ccc(C(=O)NC4CC4)cc3)cnc12]

To a solution of 100 mg (0.23 mmol) 4-{6-bromo-8-[(2-methylpropyl)amino]imidazo[1,2-a]pyrazin-3-yl}-N-cyclopropylbenzamide in 2 mL toluene were added 88 mg (0.7 mmol) pyridine-2-carboxamide, 76 mg (0.23 mmol) caesium carbonate, 8.4 mg (0.01 mmol) 1E,4E)-1,5-diphenylpenta-1,4-dien-3-one-palladium (3:2) and 10.8 mg (0.02 mmol) (9,9-dimethyl-9H-xanthene-4,5-diyl)bis(diphenylphosphane) and the mixture was heated at 140° C. for 2 h in a microwave tube. The mixture was filtered and purified by HPLC to yield 32 mg (28%) of the title compound. UPLC-MS: RT=1.32 min; m/z (ES+) 470.5 [MH$^+$]; required MW=469.5. $^1$H-NMR (300 MHz, d6-DMSO): δ=9.88 (1H, s), 8.76 (1H, s), 8.73 (1H, d), 8.56 (1H, d), 8.13-8.04 (2H, m), 7.99 (2H, d), 7.88 (1H, t), 7.76 (1H, s), 7.72 (1H, d), 7.69 (1H, m), 3.31 (2H, t), 2.87 (1H, m), 2.06 (1H, m), 0.92 (2H, d), 0.69 (2H, m), 0.55 (2H, m) ppm.

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as *acacia*, corn starch or gelatine, disintegrating agents intended to assist the break-up and dissolution of the tablet following administration such as potato starch, alginic acid, corn starch, and guar gum, gum tragacanth, *acacia*, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum *acacia* and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethylcellulose, sodium alginate, polyvinylpyrrolidone, gum tragacanth and gum *acacia*; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:
acidifying agents (examples include but are not limited to acetic acid, citric acid, fumaric acid, hydrochloric acid, nitric acid);
alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);
adsorbents (examples include but are not limited to powdered cellulose and activated charcoal);
aerosol propellants (examples include but are not limited to carbon dioxide, $CCl_2F_2$, $F_2ClC-CClF_2$ and $CClF_3$)
air displacement agents (examples include but are not limited to nitrogen and argon);
antifungal preservatives (examples include but are not limited to benzoic acid, butylparaben, ethylparaben, methylparaben, propylparaben, sodium benzoate);
antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);
antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);
binding materials (examples include but are not limited to block polymers, natural and synthetic rubber, polyacrylates, polyurethanes, silicones, polysiloxanes and styrene-butadiene copolymers);
buffering agents (examples include but are not limited to potassium metaphosphate, dipotassium phosphate, sodium acetate, sodium citrate anhydrous and sodium citrate dihydrate)
carrying agents (examples include but are not limited to *acacia* syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)
chelating agents (examples include but are not limited to edetate disodium and edetic acid)
colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);
clarifying agents (examples include but are not limited to bentonite);
emulsifying agents (examples include but are not limited to *acacia*, cetomacrogol, cetyl alcohol, glyceryl monostearate, lecithin, sorbitan monooleate, polyoxyethylene 50 monostearate);
encapsulating agents (examples include but are not limited to gelatin and cellulose acetate phthalate)
flavourants (examples include but are not limited to anise oil, cinnamon oil, cocoa, menthol, orange oil, peppermint oil and vanillin);
humectants (examples include but are not limited to glycerol, propylene glycol and sorbitol);
levigating agents (examples include but are not limited to mineral oil and glycerin);
oils (examples include but are not limited to *arachis* oil, mineral oil, olive oil, peanut oil, sesame oil and vegetable oil);
ointment bases (examples include but are not limited to lanolin, hydrophilic ointment, polyethylene glycol ointment, petrolatum, hydrophilic petrolatum, white ointment, yellow ointment, and rose water ointment);
penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)
plasticizers (examples include but are not limited to diethyl phthalate and glycerol);
solvents (examples include but are not limited to ethanol, corn oil, cottonseed oil, glycerol, isopropanol, mineral oil, oleic acid, peanut oil, purified water, water for injection, sterile water for injection and sterile water for irrigation);
stiffening agents (examples include but are not limited to cetyl alcohol, cetyl esters wax, microcrystalline wax, paraffin, stearyl alcohol, white wax and yellow wax);
suppository bases (examples include but are not limited to cocoa butter and polyethylene glycols (mixtures));
surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to *acacia*, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:
50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The additional pharmaceutical agent can be afinitor, aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BAY 80-6946, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulfate, letrozole, leucovorin, leuprolide, leuprolide acetate, lapatinib, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, RDEA 119, rebif, rhenium-186 etidronate, rituximab, roferon-A, romurtide, salagen, sandostatin, sargramostim, semustine, sizofiran, sobuzoxane, solu-medrol, sparfosic acid, stem-cell therapy, streptozocin, strontium-89 chloride, sunitinib, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, sorafenib (BAY 43-9006), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyper-proliferative agents which can be added to the composition include but are not limited to compounds listed on the cancer chemotherapy drug regimens in the 11th Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, epothilone, an epothilone derivative, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon.alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-linked lintuzumab, EM-1421, HyperAcute vaccine, tucotuzumab celmoleukin, galiximab, HPV-16-E7, Javelin—prostate cancer, Javelin—melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

The compounds of the invention may also be combined with biological therapeutic agents, such as antibodies (e.g. avastin, rituxan, erbitux, herceptin), or recombinant proteins.

The compounds of the invention may also be in combination with antiangiogenesis agents, such as, for example, with avastin, axitinib, DAST, recentin, sorafenib or sunitinib. Combinations with inhibitors of proteasomes or mTOR inhibitors, or anti-hormones or steroidal metabolic enzyme inhibitors are also possible.

Generally, the use of cytotoxic and/or cytostatic agents in combination with a compound or composition of the present invention will serve to:
(1) yield better efficacy in reducing the growth of a tumour or even eliminate the tumour as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumour progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit Mps-1 and may therefore be used for the treatment or prophylaxis of diseases of uncontrolled cell growth, hyperproliferation, inappropriate cellular immune responses, or inappropriate cellular inflammatory responses, or diseases which are accompanied with uncontrolled cell growth, hyperproliferation, inappropriate cellular immune responses, or inappropriate cellular inflammatory responses, particularly in which the uncontrolled cell growth, hyperproliferation, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, hyperproliferation, inappropriate cellular immune responses, or inappropriate cellular inflammatory responses, or diseases which are accompanied with uncontrolled cell growth, hyperproliferation, inappropriate cellular immune responses, or inappropriate cellular inflammatory responses, particularly in which the uncontrolled cell growth, hyperproliferation, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Disorders Mediated by Kinases

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab.

Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assay: Proliferation Assay

Cultivated tumour cells (MCF7, hormone dependent human mammary carcinoma cells, ATCC HTB22; NCI-H460, human non-small cell lung carcinoma cells, ATCC HTB-177; DU 145, hormone-independent human prostate carcinoma cells, ATCC HTB-81; HeLa-MaTu, human cervical carcinoma cells, EPO-GmbH, Berlin; HeLa-MaTu-ADR, multidrug-resistant human cervical carcinoma cells, EPO-GmbH, Berlin; HeLa human cervical tumour cells, ATCC CCL-2; B16F10 mouse melanoma cells, ATCC CRL-6475) were plated at a density of 5000 cells/well (MCF7, DU145, HeLa-MaTu-ADR), 3000 cells/well (NCI-H460, HeLa-MaTu, HeLa), or 1000 cells/well (B16F10) in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.01-30 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The IC50 values were determined by means of a 4 parameter fit using the company's own software.

Mps-1 Kinase Assay

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity.

N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence PWDPDDADITEILG (C-terminus in amide form, purchased from Biosynthan GmbH, Berlin) was used.

For the assay 50 nL of a 100-fold concentrated solution of the test compound in DMSO was pipetted into a black low volume 384 well microtiter plate (Greiner Bio-One, Frickenhausen, Germany), 2 µl of a solution of Mps-1 in assay buffer [0.1 mM sodium-ortho-vanadate, 10 mM $MgCl_2$, 2 mM DTT, 25 mM Hepes pH 7.7, 0.05% BSA, 0.001% Pluronic F-127] were added and the mixture was incubated for 15 min at 22° C. to allow pre-binding of the test compounds to Mps-1 before the start of the kinase reaction. Then the kinase reaction was started by the addition of 3 µl of a solution of 16.7 adenosine-tri-phosphate (ATP, 16.7 µM=>final conc. in the 5 µl assay volume is 10 µM) and peptide substrate (1.67 µM=>final conc. in the 5 µl assay volume is 1 µM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 1 nM (final conc. in the 5 µl assay volume). The reaction was stopped by the addition of 3 µl of a solution of HTRF detection reagents (100 mM Hepes pH 7.4, 0.1% BSA, 40 mM EDTA, 140 nM Streptavidin-XLent [#61GSTXLB, Fa. Cis Biointernational, Marcoule, France], 1.5 nM anti-phospho (Ser/Thr)-Europium-antibody [#AD0180, PerkinElmer LAS, Rodgau-Jügesheim, Germany].

The resulting mixture was incubated 1 h at 22° C. to allow the binding of the phosphorylated peptide to the anti-phospho (Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Jügesheim, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Test compounds were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an in-house software.

$IC_{50}$ values for compounds described in the experimental section are given in the Table.

TABLE

| Example | Mps1 IC50 [nM] |
| --- | --- |
| 1-1 | 6.2 |
| 1-2 | 7.1 |
| 1-3 | 4.2 |
| 1-4 | 1.9 |
| 1-5 | 6.2 |
| 1-6 | 2.8 |
| 1-7 | 4.1 |
| 1-8 | 3.9 |
| 1-9 | 5.8 |
| 1-10 | 72.3 |
| 1-11 | 34.3 |
| 1-12 | 132.0 |
| 1-13 | 70.6 |
| 1-14 | 38.7 |
| 1-15 | 15.4 |
| 1-16 | 46.5 |
| 1-17 | 99.2 |
| 1-18 | 31.9 |
| 1-19 | 4.2 |
| 1-20 | 21.4 |
| 2-1 | 8.3 |
| 2-2 | 94.6 |
| 2-3 | 64.0 |
| 2-4 | 12.3 |
| 3-1 | 1.0 |
| 4-1 | 12.6 |
| 4-2 | 6.1 |
| 5-1 | 1.9 |
| 6-1 | 10.4 |

Spindle Assembly Checkpoint Assay

The spindle assembly checkpoint assures the proper segregation of chromosomes during mitosis. Upon entry into mitosis, chromosomes begin to condensate which is accompanied by the phosphorylation of histone H3 on serine 10. Dephosphorylation of histone H3 on serine 10 begins in anaphase and ends at early telophase. Accordingly, phosphorylation of histone H3 on serine 10 can be utilized as a marker of cells in mitosis. Nocodazole is a microtubule destabilizing substance. Thus, nocodazole interferes with microtubule dynamics and mobilises the spindle assembly checkpoint. The cells arrest in mitosis at G2/M transition and exhibit phosphorylated histone H3 on serine 10. An inhibition of the spindle assembly checkpoint by Mps-1 inhibitors overrides the mitotic blockage in the presence of nocodazole, and the cells complete mitosis prematurely. This alteration is detected by the decrease of cells with phosphorylation of histone H3 on serine 10. This decline is used as a marker to determine the capability of compounds of the present invention to induce a mitotic breakthrough.

Cultivated cells of the human cervical tumour cell line HeLa (ATCC CCL-2) were plated at a density of 2500 cells/well in a 384-well microtiter plate in 20 µl Dulbeco's Medium (w/o phenol red, w/o sodium pyruvate, w 1000 mg/ml glucose, w pyridoxine) supplemented with 1% (v/v) glutamine, 1% (v/v) penicillin, 1% (v/v) streptomycin and 10% (v/v) fetal calf serum. After incubation overnight at 37° C., 10 µl/well nocodazole at a final concentration of 0.1 µg/ml were added to cells. After 24 h incubation, cells were arrested at G2/M phase of the cell cycle progression. Test compounds solubilised in dimethyl sulfoxide (DMSO) were added at various concentrations (0 µM, as well as in the range of 0.005 µM-10 µM; the final concentration of the solvent DMSO was 0.5% (v/v)). Cells were incubated for 4 h at 37° C. in the presence of test compounds. Thereafter, cells were fixed in 4% (v/v) paraformaldehyde in phosphate buffered saline (PBS) at 4° C. overnight then permeabilised in 0.1% (v/v) Triton X™ 100 in PBS at room temperature for 20 min and blocked in 0.5% (v/v) bovine serum albumin (BSA) in PBS at room temperature for 15 min. After washing with PBS, 20 µl/well antibody solution (anti-phospho-histone H3 clone 3H10, FITC; Upstate, Cat#16-222; 1:200 dilution) was added to cells, which were incubated for 2 h at room temperature. Afterwards, cells were washed with PBS and 20 µl/well HOECHST 33342 dye solution (5 µg/ml) was added to cells and cells were incubated 12 min at room temperature in the dark. Cells were washed twice with PBS then covered with PBS and stored at 4° C. until analysis. Images were acquired with a Perkin Elmer OPERA™ High-Content Analysis reader. Images were analyzed with image analysis software MetaXpress™ from Molecular devices utilizing the Cell Cycle application module. In this assay both labels HOECHST 33342 and phosphorylated Histone H3 on serine 10 were measured. HOECHST 33342 labels DNA and is used to count cell number. The staining of phosphorylated Histone H3 on serine 10 determines the number of mitotic cells. Inhibition of Mps-1 decreases the number of mitotic cells in the presence of nocodazole indicating an inappropriate mitotic progression. The raw assay data were further analysed by four parameter logistic regression analysis to determine the $IC_{50}$ value for each tested compound.

It will be apparent to persons skilled in the art that assays for other Mps kinases may be performed in analogy using the appropriate reagents.

Thus the compounds of the present invention effectively inhibit one or more Mps-1 kinases and are therefore suitable for the treatment or prophylaxis of diseases of uncontrolled cell growth, hyperproliferation, inappropriate cellular immune responses, or inappropriate cellular inflammatory responses, particularly in which the uncontrolled cell growth, hyperproliferation, inappropriate cellular immune responses, or inappropriate cellular inflammatory responses is mediated by Mps-1, more particularly in which the diseases of uncontrolled cell growth, hyperproliferation, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The invention claimed is:
1. A compound of formula (I):

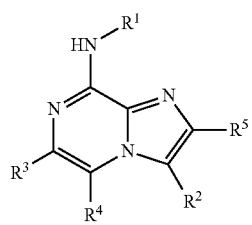

in which:
$R^1$ represents a *$CH_2$—Z moiety, * indicating the point of attachment with the rest of the molecule,
wherein Z is a hydrogen atom, or a $C_1$-$C_6$-alkyl-, —$(CH_2)_m$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl, heteroaryl-$C_1$-$C_6$-alkyl-, halo-$C_1$-$C_6$-alkyl-, R'(R")N—$C_1$-$C_6$-alkyl, HO—$C_1$-$C_6$-alkyl-, $H_2$N—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl- group;

said $C_1$-$C_6$-alkyl-, —$(CH_2)_m$—$C_2$-$C_6$-alkenyl, —$(CH_2)_n$—$C_2$-$C_6$-alkynyl, —$(CH_2)_m$—$C_3$-$C_6$-cycloalkyl, —$(CH_2)_m$-(3- to 7-membered heterocycloalkyl), aryl-$C_1$-$C_6$-alkyl-, heteroaryl-$C_1$-$C_6$-alkyl-, halo-$C_1$-$C_6$-alkyl-, R'(R")N—$C_1$-$C_6$-alkyl-, HO—$C_1$-$C_6$-alkyl-, $H_2$N—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl- group, is optionally substituted, identically or differently, with 1, 2, 3, or 4 $R^7$ groups;

$R^2$ represents a

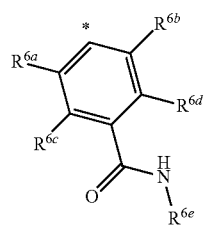

group,
in which * indicates the point of attachment with the rest of the molecule, and in which
$R^{6a}$, $R^{6b}$, $R^{6c}$, and $R^{6d}$
represent, independently from each other, a hydrogen or halogen atom, or a —CN, $C_1$-$C_6$-alkyl-, $C_1$-$C_6$-alkoxy-, halo-$C_1$-$C_6$-alkyl-, R(R')N—$C_1$-$C_6$-alkyl-, HO—$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —C(=O)R, —C(=O)N(H)R, —C(=O)N(R)R', —C(=O)O—R, —N(R)R', —$NO_2$, —N(H)C (=O)R, —N(R)C(=O)R', —N(H)C(=O)N(R) R', —N(R)C(=O)N(R')R", —N(H)C(=O)OR, —N(R)C(=O)OR', —N(H)S(=O)R', —N(R)S (=O)R', —N(H)S(=O)$_2$R, —N(R)S(=O)$_2$R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)$_2$R, —S(=O)$_2$N(H)R, —S(=O)$_2$N(R) R', —S(=O)(=NR)R' group; and
$R^{6e}$ represents a cyclopropyl-group being optionally substituted, identically or differently, with 1, 2, 3, or 4 groups selected from:
hydrogen, halogen, —OH, —CN, $C_1$-$C_6$-alkyl-, —$C_1$-$C_6$-alkoxy, halo-$C_1$-$C_6$-alkyl-;
$R^3$ represents a —N(H)C(=O)R or a

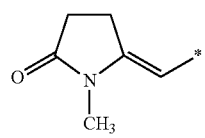

group, wherein
* indicates the point of attachment with the rest of the molecule;

said —N(H)C(=O)R or

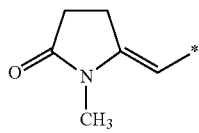 [SMILES: */C=C1\CCC(=O)N1C]

group,
being optionally substituted, identically or differently, with 1, 2, 3, or 4 R$^8$ groups;

R$^4$ represents a hydrogen or halogen atom, or a —CN, C$_1$-C$_6$-alkyl- or aryl-group;

R$^5$ represents a hydrogen atom;

R$^7$ represents a hydrogen or halogen atom, or a —CN, HO—, C$_1$-C$_6$-alkoxy-, C$_1$-C$_6$-alkyl-, halo-C$_1$-C$_6$-alkyl-, halo-C$_1$-C$_6$-alkoxy- R(R')N—C$_1$-C$_6$-alkyl-, HO—C$_1$-C$_6$-alkyl, HO—C$_1$-C$_6$-alkoxy, C$_1$-C$_6$-alkoxy-C$_1$-C$_6$-alkyl-, halo-C$_1$-C$_6$-alkoxy-C$_1$-C$_6$-alkyl-, C$_2$-C$_6$-alkenyl, 3- to 7-membered heterocycloalkyl, aryl-, heteroaryl-, —C(=O)R, —C(=O)N(H)R, —C(=O)N(R)R', —C(=O)O—R, —N(R)R', —NO$_2$, —N(H)C(=O)R, —N(R)C(=O)R', —N(H)C(=O)N(R)R', —N(R)C(=O)N(R')R", —N(H)C(=O)OR, —N(R)C(=O)OR', —N(H)S(=O)R, —N(R)S(=O)R', —N(H)S(=O)$_2$R, —N(R)S(=O)$_2$R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)$_2$R, —S(=O)$_2$N(H)R, —S(=O)$_2$N(R)R', —S(=O)(=NR)R', —S(=O)$_2$-(3- to 7-membered heterocycloalkyl) group;
wherein said 3- to 7-membered heterocycloalkyl- or heteroaryl-, is optionally substituted, identically or differently, with 1, 2, 3, or 4 C$_1$-C$_6$-alkyl- groups R$^8$ represents a hydrogen or halogen atom, or a —CN, HO—, C$_1$-C$_6$-alkoxy-, halo-C$_1$-C$_6$-alkoxy-, C$_1$-C$_6$-alkyl-, —C$_1$-C$_6$-alkyl-N(H)C(=O)R, —C$_1$-C$_6$-alkyl-C(=O)N(H)R, —C$_1$-C$_6$-alkyl-C(=O)OR, halo-C$_1$-C$_6$-alkyl-, R(R')N—C$_1$-C$_6$-alkyl-, HO—C$_1$-C$_6$-alkyl, HO—C$_1$-C$_6$-alkoxy, C$_1$-C$_6$-alkoxy-C$_1$-C$_6$-alkyl-, halo-C$_1$-C$_6$-alkoxy-C$_1$-C$_6$-alkyl-, —C$_2$-C$_6$-alkenyl, 3- to 7-membered heterocycloalkyl-, aryl-, heteroaryl-, —C(=O)R, —C(=O)N(H)R, —C(=O)N(R)R', —C(=O)O—R, —N(R)R', —NO$_2$, —N(H)C(=O)R, —N(R)C(=O)R', —N(H)C(=O)N(R)R', —N(R)C(=O)N(R')R", —N(H)C(=O)OR, N(R)C(=O)OR', —N(H)S(=O)R, —N(R)S(=O)R', —N(H)S(=O)$_2$R, —N(R)S(=O)$_2$R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)$_2$R, —S(=O)$_2$N(H)R, —S(=O)$_2$N(R)R', —S(=O)(=NR)R', —S(=O)$_2$-(3- to 7-membered heterocycloalkyl) group;

R, R' and R" are, independently from each other, a hydrogen atom or a C$_1$-C$_6$-alkyl-, —C$_3$-C$_6$-cycloalkyl, C$_3$-C$_6$-alkenyl-, aryl- or a heteroaryl- group;

m is 0, 1, 2, 3, 4, 5 or 6; and n is 1, 2, 3, 4 or 5;

or a stereoisomer, a tautomer, an N-oxide, or a pharmaceutically acceptable salt thereof, or a mixture of same.

2. The compound according to claim 1, wherein:

R$^1$ represents a *CH$_2$—Z moiety, * indicating the point of attachment with the rest of the molecule, wherein Z is a hydrogen atom, or a C$_1$-C$_6$-alkyl-, —(CH$_2$)$_m$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R'(R")N—C$_1$-C$_6$-alkyl-, HO—C$_1$-C$_6$-alkyl-, H$_2$N—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl, a 3- to 7-membered heterocycloalkyl-, C$_2$-C$_6$-alkenyl-, C$_4$-C$_8$-cycloalkenyl-, C$_2$-C$_6$-alkynyl-, aryl- or heteroaryl- group;

said C$_1$-C$_6$-alkyl-, —(CH$_2$)$_m$—C$_2$-C$_6$-alkenyl, —(CH$_2$)$_n$—C$_2$-C$_6$-alkynyl, —(CH$_2$)$_m$—C$_3$-C$_6$-cycloalkyl, —(CH$_2$)$_m$-(3- to 7-membered heterocycloalkyl), aryl-C$_1$-C$_6$-alkyl-, heteroaryl-C$_1$-C$_6$-alkyl-, halo-C$_1$-C$_6$-alkyl-, R'(R")N—C$_1$-C$_6$-alkyl-, HO—C$_1$-C$_6$-alkyl-, H$_2$N—C$_1$-C$_6$-alkyl-, —C$_1$-C$_6$-alkyl-CN, C$_1$-C$_6$-alkoxy-C$_1$-C$_6$-alkyl-, halo-C$_1$-C$_6$-alkoxy-C$_1$-C$_6$-alkyl-, C$_3$-C$_6$-cycloalkyl-, a 3- to 7-membered heterocycloalkyl-, C$_2$-C$_6$-alkenyl-, C$_4$-C$_8$-cycloalkenyl-, C$_2$-C$_6$-alkynyl-, aryl- or heteroaryl- group, is optionally substituted, identically or differently, with 1, 2, 3, or 4 R$^7$ groups;

R$^2$ represents a

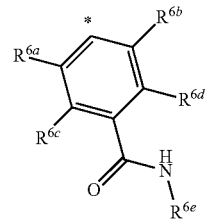

group,
in which * indicates the point of attachment with the rest of the molecule, and in which R$^{6a}$, R$^{6b}$, R$^{6c}$, and R$^{6d}$ represent, independently from each other, a hydrogen or halogen atom; and R$^{6e}$ represents a cyclopropyl-group;

R$^3$ represents a —N(H)C(=O)R or a

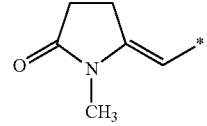 [SMILES: */C=C1\CCC(=O)N1C]

group, wherein
* indicates the point of attachment with the rest of the molecule;

said —N(H)C(=O)R or

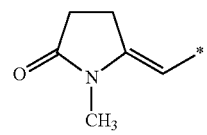

group,
being optionally substituted, identically or differently, with 1, 2, 3, or 4 R$^8$ groups;

R⁴ represents a hydrogen or halogen atom, or a —CN, $C_1$-$C_6$-alkyl- or aryl-group;

R⁵ represents a hydrogen atom;

R⁷ represents a hydrogen or halogen atom, or a —CN, HO—, $C_1$-$C_6$-alkoxy-, $C_1$-$C_6$-alkyl-, halo-$C_1$-$C_6$-alkyl-, halo-$C_1$-$C_6$-alkoxy- R(R')N—$C_1$-$C_6$-alkyl-, HO—$C_1$-$C_6$-alkyl, HO—$C_1$-$C_6$-alkoxy, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)R, —C(=O)N(H)R, —C(=O)N(R)R', —C(=O)O—R, —N(R)R', —NO₂, —N(H)C(=O)R, —N(R)C(=O)R', —N(H)C(=O)N(R)R', —N(R)C(=O)N(R')R", —N(H)C(=O)OR, —N(R)C(=O)OR', —N(H)S(=O)R, —N(R)S(=O)R', —N(H)S(=O)₂R, —N(R)S(=O)₂R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)₂R, —S(=O)₂N(H)R, —S(=O)₂N(R)R', —S(=O)(=NR)R', —S(=O)₂-(3- to 7-membered heterocycloalkyl) group;

R⁸ represents a hydrogen or halogen atom, or a —CN, HO—, $C_1$-$C_6$-alkoxy-, halo-$C_1$-$C_6$-alkoxy-, $C_1$-$C_6$-alkyl-, —$C_1$-$C_6$-alkyl-N(H)C(=O)R, —$C_1$-$C_6$-alkyl-C(=O)N(H)R, —$C_1$-$C_6$-alkyl-C(=O)OR, halo-$C_1$-$C_6$-alkyl-, R(R')N—$C_1$-$C_6$-alkyl-, HO—$C_1$-$C_6$-alkyl, HO—$C_1$-$C_6$-alkoxy, $C_1$-$C_6$-alkoxy-$C_1$-$C_6$-alkyl-, halo-$C_1$-$C_6$-alkoxy-$C_1$-$C_6$-alkyl-, —$C_2$-$C_6$-alkenyl, 3- to 7-membered heterocycloalkyl-, aryl-, heteroaryl-, —C(=O)R, —C(=O)N(H)R, —C(=O)N(R)R', —C(=O)O—R, —N(R)R', —NO₂, —N(H)C(=O)R, —N(R)C(=O)R', —N(H)C(=O)N(R)R', —N(R)C(=O)N(R')R", —N(H)C(=O)OR, N(R)C(=O)OR', —N(H)S(=O)R, —N(R)S(=O)R', —N(H)S(=O)₂R, —N(R)S(=O)₂R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O₂)R, —S(=O)₂N(H)R, —S(=O)₂N(R)R', —S(=O)(=NR)R', —S(=O)₂-(3- to 7-membered heterocycloalkyl) group;

R, R' and R" are, independently from each other, a hydrogen atom or a $C_1$-$C_6$-alkyl-, —$C_3$-$C_6$-cycloalkyl, $C_3$-$C_6$-alkenyl-, aryl- or a heteroaryl- group;

m is 0, 1, 2, 3, 4, 5 or 6; and n is 1, 2, 3, 4 or 5;

or a stereoisomer, a tautomer, an N-oxide, or a pharmaceutically acceptable salt thereof, or a mixture of same.

3. The compound according to claim 1, wherein:

R¹ represents a *CH₂—Z moiety, * indicating the point of attachment with the rest of the molecule, wherein Z is a hydrogen atom, or a $C_1$-$C_6$-alkyl-, —(CH₂)ₘ—$C_2$-$C_6$-alkenyl, —(CH₂)ₙ—$C_2$-$C_6$-alkynyl, —(CH₂)ₘ—$C_3$-$C_6$-cycloalkyl, —(CH₂)ₘ-(3- to 7-membered heterocycloalkyl), aryl-$C_1$-$C_6$-alkyl-, heteroaryl-$C_1$-$C_6$-alkyl-, halo-$C_1$-$C_6$-alkyl-, R'(R")N—$C_1$-$C_6$-alkyl-, HO—$C_1$-$C_6$-alkyl-, H₂N—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl- group;

said $C_1$-$C_6$-alkyl-, —(CH₂)ₘ—$C_2$-$C_6$-alkenyl, —(CH₂)ₙ—$C_2$-$C_6$-alkynyl, —(CH₂)ₘ—$C_3$-$C_6$-cycloalkyl, —(CH₂)ₘ-(3- to 7-membered heterocycloalkyl), aryl-$C_1$-$C_6$-alkyl-, heteroaryl-$C_1$-$C_6$-alkyl-, halo-$C_1$-$C_6$-alkyl-, R'(R")N—$C_1$-$C_6$-alkyl-, HO—$C_1$-$C_6$-alkyl-, H₂N—$C_1$-$C_6$-alkyl-, —$C_1$-$C_6$-alkyl-CN, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, a 3- to 7-membered heterocycloalkyl-, $C_2$-$C_6$-alkenyl-, $C_4$-$C_8$-cycloalkenyl-, $C_2$-$C_6$-alkynyl-, aryl- or heteroaryl- group, is optionally substituted, identically or differently, with 1, 2, 3, or 4 R⁷ groups;

R² represents a group, in which * indicates the point of attachment with the rest of the molecule, and in which $R^{6a}$, $R^{6b}$, $R^{6c}$, and $R^{6d}$ represent, independently from each other, a hydrogen or halogen atom; and $R^{6e}$ represents a cyclopropyl-group;

R³ represents a —N(H)C(=O)R or a group, wherein

* indicates the point of attachment with the rest of the molecule;

said —N(H)C(=O)R or group, being optionally substituted, identically or differently, with 1, 2, 3, or 4 R⁸ groups;

R⁴ represents a hydrogen atom;

R⁵ represents a hydrogen atom;

R⁷ represents a hydrogen or halogen atom, or a —CN, HO—, $C_1$-$C_6$-alkoxy-, $C_1$-$C_6$-alkyl-, halo-$C_1$-$C_6$-alkyl-, halo-$C_1$-$C_6$-alkoxy- R(R')N—$C_1$-$C_6$-alkyl-, HO—$C_1$-$C_6$-alkyl, HO—$C_1$-$C_6$-alkoxy, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl, 3- to 7-membered heterocycloalkyl, aryl-, heteroaryl-, —C(=O)R, —C(=O)N(H)R, —C(=O)N(R)R', —C(=O)O—R, —N(R)R', —NO₂, —N(H)C(=O)R, —N(R)C(=O)R', —N(H)C(=O)N(R)R', —N(R)C(=O)N(R')R", —N(H)C(=O)OR, —N(R)C(=O)OR', —N(H)S(=O)R, —N(R)S(=O)R', —N(H)S(=O)₂R, —N(R)S(=O)₂R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O)₂R, —S(=O)₂N(H)R, —S(=O)₂N(R)R', —S(=O)(=NR)R', —S(=O)₂-(3- to 7-membered heterocycloalkyl) group;

R⁸ represents a hydrogen or halogen atom, or a —CN, HO—, $C_1$-$C_6$-alkoxy-, halo-$C_1$-$C_6$-alkoxy-, $C_1$-$C_6$-alkyl-, —$C_1$-$C_6$-alkyl-N(H)C(=O)R, —$C_1$-$C_6$-alkyl-C(=O)N(H)R, —$C_1$-$C_6$-alkyl-C(=O)OR, halo-$C_1$-$C_6$-alkyl-, R(R')N—$C_1$-$C_6$-alkyl-, HO—$C_1$-$C_6$-alkyl, HO—$C_1$-$C_6$-alkoxy, $C_1$-$C_6$-alkoxy-$C_1$-$C_6$-alkyl-, halo-$C_1$-$C_6$-alkoxy-$C_1$-$C_6$-alkyl-, —$C_2$-$C_6$-alkenyl, 3- to 7-membered heterocycloalkyl-, aryl-, heteroaryl-, —C(=O)R, —C(=O)N(H)R, —C(=O)N(R)R', —C(=O)O—R, —N(R)R', —NO₂, —N(H)C(=O)R, —N(R)C(=O)R', —N(H)C(=O)N(R)R', —N(R)C(=O)N(R')R", —N(H)C(=O)OR, N(R)C(=O)OR', —N(H)S(=O)R, —N(R)S(=O)R', —N(H)S(=O)₂R, —N(R)S(=O)₂R', —N=S(=O)(R)R', —OR, —O(C=O)R, —O(C=O)N(R)R', —O(C=O)OR, —SR, —S(=O)R, —S(=O)N(H)R, —S(=O)N(R)R', —S(=O₂)R, —S(=O)₂N(H)R, —S(=O)₂N(R)R', —S(=O)(=NR)R', —S(=O)₂-(3- to 7-membered heterocycloalkyl) group;

R, R' and R" are, independently from each other, a hydrogen atom or a $C_1$-$C_6$-alkyl-, —$C_3$-$C_6$-cycloalkyl, $C_3$-$C_6$-alkenyl-, aryl- or a heteroaryl- group;

m is 0, 1, 2, 3, 4, 5 or 6; and n is 1, 2, 3, 4 or 5;

or a stereoisomer, a tautomer, an N-oxide, or a pharmaceutically acceptable salt thereof, or a mixture of same.

4. The compound according to claim 1, wherein:

R¹ represents a *CH₂—Z moiety, * indicating the point of attachment with the rest of the molecule, wherein Z is a hydrogen atom, or a $C_1$-$C_6$-alkyl-, —(CH₂)ₘ—$C_2$-$C_6$-alkenyl, —(CH₂)ₙ—$C_2$-$C_6$-alkynyl, —(CH₂)ₘ-(3- to 7-membered heterocycloalkyl), halo-$C_1$-$C_6$-alkyl-, HO—$C_1$-$C_6$-alkyl-, $C_2$-$C_6$-alkenyl-, $C_2$-$C_6$-alkynyl-, or heteroaryl- group;

said $C_1$-$C_6$-alkyl-, —(CH₂)ₘ—$C_2$-$C_6$-alkenyl, —(CH₂)ₙ—$C_2$-$C_6$-alkynyl, —(CH₂)ₘ-(3- to 7-membered heterocycloalkyl), halo-$C_1$-$C_6$-alkyl-, HO—$C_1$-$C_6$-alkyl-, $C_2$-$C_6$-alkenyl-, $C_2$-$C_6$-alkynyl-, or heteroaryl- group, is optionally substituted, identically or differently, with 1, 2, 3, or 4 R⁷ groups;

R² represents a group

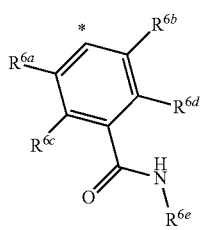

in which * indicates the point of attachment with the rest of the molecule, and in which $R^{6a}$, $R^{6b}$, $R^{6c}$, and $R^{6d}$ represent, independently from each other, a hydrogen or halogen atom; and $R^{6e}$ represents a cyclopropyl- group;

R³ represents a —N(H)C(=O)R or a

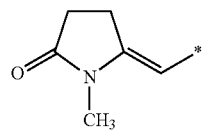

group, wherein

* indicates the point of attachment with the rest of the molecule;

said —N(H)C(=O)R or a

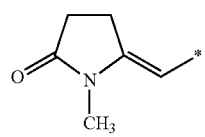

group, being optionally substituted, identically or differently, with 1, 2, 3, or 4 R⁸ groups;

R⁴ represents a hydrogen atom;

R⁵ represents a hydrogen atom;

R⁷ represents a hydrogen atom or a —N(H)C(=O)OR, —N(R)C(=O)OR'-group;

R⁸ represents a hydrogen atom or a $C_1$-$C_6$-alkoxy-$C_1$-$C_6$-alkyl-, —$C_2$-$C_6$-alkenyl, —S(=O)R group;

R, R' and R" are, independently from each other, a hydrogen atom or a —$C_3$-$C_6$-cycloalkyl or heteroaryl- group;

m is 0 or 1; and n is 1;

or a stereoisomer, a tautomer, an N-oxide, or a pharmaceutically acceptable salt thereof, or a mixture of same.

5. The compound according to claim 1, which is selected from the group consisting of:

N-cyclopropyl-4-{6-[(E)-(1-methyl-5-oxopyrrolidin-2-ylidene)methyl]-8-[(2-methylpropyl)amino]imidazo[1,2-a]pyrazin-3-yl}benzamide; and N-{3-[4-(cyclopropylcarbamoyl)phenyl]-8-[(2-methylpropyl)amino]imidazo[1,2-a]pyrazin-6-yl}pyridine-2-carboxamide.

6. A pharmaceutical composition comprising a compound of formula (I), or a stereoisomer, a tautomer, an N-oxide, or a pharmaceutically acceptable salt thereof, or a mixture of same, according to claim 1, and a pharmaceutically acceptable diluent or carrier.

7. A method for inhibiting monopolar spindle 1 kinase in a patient, comprising administering to the patient in need thereof a compound of formula (I), or a stereoisomer, a tautomer, an N-oxide, or a pharmaceutically acceptable salt thereof, or a mixture of same, according to claim 1.

8. A method of preparing a compound of formula (I) according to claim 1, said method comprising the step of reacting an intermediate compound of formula (13):

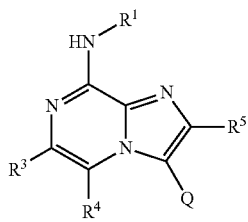

in which Q is a chlorine, bromine, or iodine atom,
with a compound of formula (13a):

R²—Y in which R² is as defined in claim 1, and Y is —B(OH)₂ or —B(OC₁-C₆-alkyl)₂,
thereby giving a compound of formula (I):

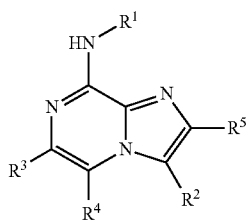
(I)

9. A method of preparing a compound of formula (I) according to claim 1, said method comprising the step of reacting an intermediate compound of formula (9):

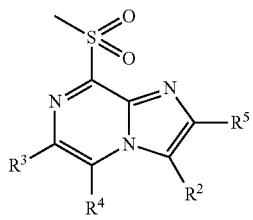
(9)

with a compound of formula (9a):

H₂N—R¹ in which R¹ is as defined in claim 1,
thereby giving a compound of formula (I):

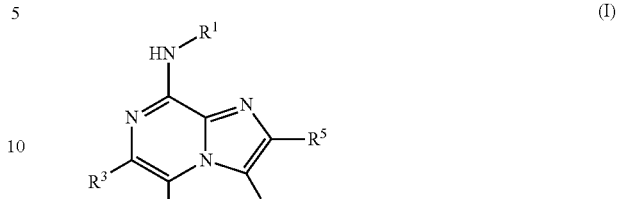
(I)

10. A method of preparing a compound of formula (I) according to claim 1, said method comprising the step of reacting an intermediate compound of formula (6):

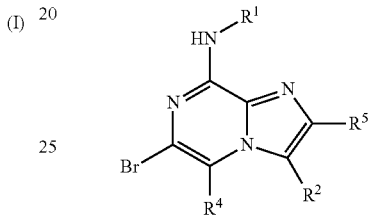

with a compound of formula (6a):

R³—Y in which R³ is as defined in claim 1, and Y is —B(OH)₂ or —B(OC₁-C₆-alkyl)₂,
thereby giving a compound of formula (I):

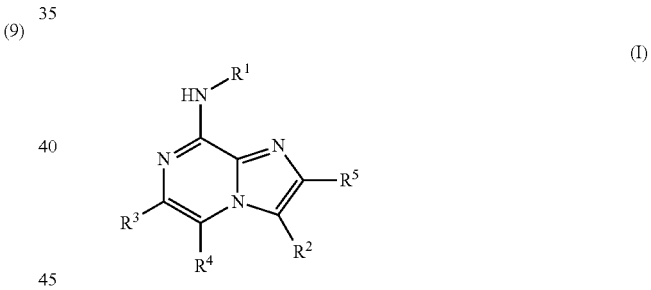
(I)

\* \* \* \* \*